(12) United States Patent
Lahoud et al.

(10) Patent No.: US 11,744,963 B2
(45) Date of Patent: *Sep. 5, 2023

(54) MIST INHALER DEVICES

(71) Applicant: SHAHEEN INNOVATIONS HOLDING LIMITED, Abu Dhabi (AE)

(72) Inventors: Imad Lahoud, Abu Dhabi (AE); Mohammed Alshaiba Saleh Ghannam Almazrouei, Abu Dhabi (AE); Sajid Bhatti, Abu Dhabi (AE); Jeff Machovec, Abu Dhabi (AE); Clement Lamoureux, Abu Dhabi (AE)

(73) Assignee: Shaheen Innovations Holding Limited, Abu Dhabi (AE)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,995

(22) Filed: Jun. 10, 2022

(65) Prior Publication Data

US 2022/0362494 A1 Nov. 17, 2022

Related U.S. Application Data

(63) Continuation of application No. 17/122,025, filed on Dec. 15, 2020, which is a continuation-in-part of
(Continued)

(30) Foreign Application Priority Data

Apr. 6, 2020 (EP) .................................. 20168231
Apr. 6, 2020 (EP) .................................. 20168245
Apr. 9, 2020 (EP) .................................. 20168938

(51) Int. Cl.
*A61M 15/00* (2006.01)
*A61M 15/06* (2006.01)
(Continued)

(52) U.S. Cl.
CPC ....... *A61M 15/0085* (2013.01); *A24B 15/167* (2016.11); *A24F 40/05* (2020.01);
(Continued)

(58) Field of Classification Search
CPC .............. A61M 15/001; A61M 15/002; A61M 2205/3368; A61M 2205/3375;
(Continued)

(56) References Cited

U.S. PATENT DOCUMENTS 4,119,096 A 10/1978 Drews
4,334,531 A 6/1982 Reichl
(Continued)

FOREIGN PATENT DOCUMENTS

CN 101648041 A 2/2010
CN 104055225 A 9/2014
(Continued)

OTHER PUBLICATIONS

English translation for CN 105795526, machine translated by Search Clarivate Analytics, translated on Mar. 24, 2023.*
(Continued)

*Primary Examiner* — Tu A Vo
(74) *Attorney, Agent, or Firm* — Amedeo F. Ferraro, Esq.

(57) ABSTRACT

A mist inhaler device (200) for generating a mist for inhalation by a user. The device includes a mist generator device (201) and a driver device (202). The driver device (202) is configured to drive the mist generator device (201) at an optimum frequency to maximise the efficiency of mist generation by the mist generator device (201).

11 Claims, 33 Drawing Sheets

Related U.S. Application Data application No. PCT/IB2019/060808, filed on Dec. 15, 2019, and a continuation-in-part of application No. PCT/IB2019/060810, filed on Dec. 15, 2019, and a continuation-in-part of application No. PCT/IB2019/060812, filed on Dec. 15, 2019, and a continuation-in-part of application No. PCT/IB2019/060811, filed on Dec. 15, 2019.

(51) Int. Cl.

| | |
|---|---|
| *A24F 40/53* | (2020.01) |
| *A24F 40/65* | (2020.01) |
| *A24F 40/48* | (2020.01) |
| *A24F 40/10* | (2020.01) |
| *A24F 40/44* | (2020.01) |
| *A24F 40/05* | (2020.01) |
| *A24F 40/51* | (2020.01) |
| *A24F 40/50* | (2020.01) |
| *A61M 11/00* | (2006.01) |
| *B05B 17/06* | (2006.01) |
| *A24B 15/167* | (2020.01) |
| *B05B 17/00* | (2006.01) |

(52) U.S. Cl.
CPC ............. *A24F 40/10* (2020.01); *A24F 40/44* (2020.01); *A24F 40/48* (2020.01); *A24F 40/50* (2020.01); *A24F 40/51* (2020.01); *A24F 40/53* (2020.01); *A24F 40/65* (2020.01); *A61M 11/005* (2013.01); *A61M 15/06* (2013.01); *B05B 17/063* (2013.01); *B05B 17/0661* (2013.01); *B05B 17/0669* (2013.01); *B05B 17/0684* (2013.01); *A61M 15/0021* (2014.02); *A61M 15/0081* (2014.02); *A61M 2205/0294* (2013.01); *A61M 2205/276* (2013.01); *A61M 2205/3331* (2013.01); *A61M 2205/3592* (2013.01); *A61M 2205/50* (2013.01); *A61M 2205/52* (2013.01); *A61M 2205/60* (2013.01); *A61M 2205/8206* (2013.01); *A61M 2205/8212* (2013.01); *A61M 2205/8237* (2013.01); *A61M 2230/40* (2013.01); *B05B 17/0646* (2013.01); *B06B 2201/77* (2013.01)

(58) Field of Classification Search
CPC .......... A61M 2205/8206; A61M 15/06; A61M 15/0085; A24F 40/05; A24F 40/10; A24F 40/44; A24F 40/51; A24F 40/53; A24B 15/167; B05B 17/0653; B05B 12/08; B05B 17/0646; B05B 17/0661; B05B 17/0669; B05B 17/0684
See application file for complete search history.

(56) References Cited

U.S. PATENT DOCUMENTS

| | | |
|---|---|---|
| 5,355,873 A | 10/1994 | Del Bon |
| 5,518,179 A | 5/1996 | Humberstone et al. |
| 5,551,416 A | 9/1996 | Stimpson |
| 5,894,841 A | 4/1999 | Voges |
| 6,011,345 A | 1/2000 | Murray |
| 6,040,560 A | 3/2000 | Fleischhauer |
| 6,402,046 B1 | 6/2002 | Loeser |
| 6,601,581 B1 | 8/2003 | Babaev |
| 6,679,436 B1 | 1/2004 | Onishi |
| 7,129,619 B2 | 10/2006 | Yang |
| 8,991,722 B2 | 3/2015 | Friend |
| 9,242,263 B1 | 1/2016 | Copeman |
| 9,278,365 B2 | 3/2016 | Banco |
| 9,415,412 B2 | 8/2016 | Kawashima |
| 9,687,029 B2 | 6/2017 | Liu |
| 9,687,627 B2 | 6/2017 | Gallem |
| 9,718,078 B1 | 8/2017 | Chau |
| 9,867,398 B2 | 1/2018 | Guo |
| 9,980,140 B1 | 5/2018 | Spencer |
| 10,034,495 B2 | 7/2018 | Alarcon |
| 10,071,391 B2 | 9/2018 | Yu |
| 10,195,368 B2 | 2/2019 | Wang |
| 10,300,225 B2 | 5/2019 | Terry |
| 10,327,479 B2 | 6/2019 | Popplewell |
| 10,328,218 B2 | 6/2019 | Reed |
| 10,561,803 B2 | 2/2020 | Liu |
| 2002/0129813 A1 | 9/2002 | Litherland |
| 2003/0192532 A1 | 10/2003 | Hopkins |
| 2003/0209005 A1 | 11/2003 | Fenn |
| 2006/0243277 A1 | 11/2006 | Denyer |
| 2007/0125370 A1 | 6/2007 | Denyer |
| 2008/0088202 A1 | 4/2008 | Duru |
| 2008/0156320 A1 | 7/2008 | Low |
| 2008/0164339 A1 | 7/2008 | Duru |
| 2009/0022669 A1 | 1/2009 | Waters |
| 2010/0084488 A1 | 4/2010 | Mahoney, III |
| 2010/0139652 A1 | 6/2010 | Lipp |
| 2012/0126041 A1 | 5/2012 | Mahito et al. |
| 2013/0220315 A1 | 8/2013 | Conley |
| 2014/0007864 A1 | 1/2014 | Gordon |
| 2014/0151457 A1 | 6/2014 | Wilkerson |
| 2014/0261414 A1 | 9/2014 | Weitzel |
| 2014/0270727 A1 | 9/2014 | Ampolini |
| 2015/0202387 A1 | 7/2015 | Yu |
| 2015/0230522 A1 | 8/2015 | Horn |
| 2015/0231347 A1 | 8/2015 | Gumaste |
| 2016/0001316 A1 | 1/2016 | Friend |
| 2016/0066619 A1 | 3/2016 | Di Carlo |
| 2016/0089508 A1 | 3/2016 | Smith |
| 2016/0199594 A1 | 7/2016 | Finger |
| 2016/0206001 A1 | 7/2016 | Eng |
| 2016/0213866 A1 | 7/2016 | Tan |
| 2016/0324212 A1 | 11/2016 | Cameron |
| 2017/0042242 A1 | 2/2017 | Hon |
| 2017/0119052 A1 | 5/2017 | Williams |
| 2017/0135411 A1 | 5/2017 | Cameron |
| 2017/0265521 A1 | 9/2017 | Do |
| 2017/0136484 A1 | 10/2017 | Wilkerson |
| 2017/0281883 A1 | 10/2017 | Li |
| 2017/0303594 A1 | 10/2017 | Cameron |
| 2017/0368273 A1 | 12/2017 | Rubin |
| 2018/0042306 A1 | 2/2018 | Atkins |
| 2018/0153217 A1 | 6/2018 | Liu |
| 2018/0160737 A1 | 6/2018 | Verleur |
| 2018/0192702 A1 | 7/2018 | Li |
| 2018/0269867 A1 | 9/2018 | Terashima |
| 2018/0286207 A1 | 10/2018 | Baker |
| 2018/0296777 A1 | 10/2018 | Terry |
| 2018/0296778 A1 | 10/2018 | Hacker |
| 2018/0310625 A1 | 11/2018 | Alarcon |
| 2018/0338532 A1 | 11/2018 | Verleur |
| 2018/0343926 A1 | 12/2018 | Wensley |
| 2019/0056131 A1 | 2/2019 | Warren |
| 2019/0098935 A1 | 4/2019 | Phan |
| 2019/0116863 A1 | 4/2019 | Dull |
| 2019/0158938 A1 | 5/2019 | Bowen |
| 2019/0166913 A1 | 6/2019 | Trzecieski |
| 2019/0216135 A1* | 7/2019 | Guo .......... A24F 40/44 |
| 2019/0255554 A1 | 8/2019 | Selby |
| 2019/0289914 A1* | 9/2019 | Liu .......... A24F 40/42 |
| 2019/0289915 A1 | 9/2019 | Heidi |
| 2019/0289918 A1 | 9/2019 | Hon |
| 2019/0321570 A1 | 10/2019 | Rubin |
| 2019/0329281 A1 | 10/2019 | Lin |
| 2019/0335580 A1 | 10/2019 | Lin |
| 2019/0336710 A1 | 11/2019 | Yamada |
| 2019/0373679 A1 | 12/2019 | Fu |
| 2019/0387795 A1 | 12/2019 | Fisher |
| 2020/0000143 A1 | 1/2020 | Anderson |
| 2020/0000146 A1 | 1/2020 | Anderson |
| 2020/0009600 A1 | 1/2020 | Tan |
| 2020/0016344 A1 | 1/2020 | Scheck |
| 2020/0022416 A1 | 1/2020 | Alarcon |
| 2020/0046030 A1 | 2/2020 | Krietzman |

(56) References Cited

U.S. PATENT DOCUMENTS

| | | |
|---|---|---|
| 2020/0068949 A1 | 3/2020 | Rasmussen |
| 2020/0085100 A1 | 3/2020 | Hoffman |
| 2020/0120989 A1 | 4/2020 | Danek |
| 2020/0120991 A1 | 4/2020 | Hatton |
| 2020/0146361 A1 | 5/2020 | Silver |
| 2020/0178598 A1 | 6/2020 | Mitchell |
| 2020/0214349 A1 | 7/2020 | Liu |
| 2020/0221771 A1 | 7/2020 | Atkins |
| 2020/0221776 A1 | 7/2020 | Liu |
| 2020/0245692 A1 | 8/2020 | Cameron |
| 2020/0345058 A1 | 11/2020 | Bowen |
| 2020/0404975 A1 | 12/2020 | Chen |
| 2021/0076733 A1 | 3/2021 | Liu |
| 2021/0112858 A1 | 4/2021 | Liu |
| 2021/0153548 A1 | 5/2021 | Twite |
| 2021/0153549 A1 | 5/2021 | Twite |
| 2021/0153564 A1 | 5/2021 | Hourmand |
| 2021/0153565 A1 | 5/2021 | Twite |
| 2021/0153566 A1 | 5/2021 | Hourmand |
| 2021/0153567 A1 | 5/2021 | Twite |
| 2021/0153568 A1 | 5/2021 | Twite |
| 2021/0153569 A1 | 5/2021 | Twite |
| 2021/0177056 A1 | 6/2021 | Yilmaz |
| 2021/0212362 A1 | 7/2021 | Liu |
| 2021/0378303 A1 | 12/2021 | Liu |
| 2021/0401061 A1 | 12/2021 | Davis |
| 2022/0273037 A1 | 9/2022 | Liu |
| 2023/0001107 A1 | 1/2023 | Connolly |

FOREIGN PATENT DOCUMENTS

| | | | | |
|---|---|---|---|---|
| CN | 204070580 U | 1/2015 | | |
| CN | 105747277 A | 7/2016 | | |
| CN | 105795526 A | * 7/2016 | ............ | A24F 40/05 |
| CN | 105795526 A | 7/2016 | | |
| CN | 105876873 A | 8/2016 | | |
| CN | 205432145 U | 8/2016 | | |
| CN | 106108118 A | 11/2016 | | |
| CN | 205831074 A | 12/2016 | | |
| CN | 106422005 | 2/2017 | | |
| CN | 205947130 U | 2/2017 | | |
| CN | 206025223 U | 3/2017 | | |
| CN | 206043451 U | 3/2017 | | |
| CN | 206079025 U | 4/2017 | | |
| CN | 206119183 U | 4/2017 | | |
| CN | 206119184 U | 4/2017 | | |
| CN | 106617319 A | 5/2017 | | |
| CN | 206303211 U | 7/2017 | | |
| CN | 206333372 U | 7/2017 | | |
| CN | 107048479 A | 8/2017 | | |
| CN | 206586397 U | 10/2017 | | |
| CN | 206949536 U | 2/2018 | | |
| CN | 108283331 A | 7/2018 | | |
| CN | 10835521 | 8/2018 | | |
| CN | 105876873 B | 12/2018 | | |
| CN | 109619655 A | 1/2019 | | |
| CN | 208434721 U | 1/2019 | | |
| CN | 106108118 B | 4/2019 | | |
| CN | 208837110 U | 5/2019 | | |
| CN | 209060228 U | 7/2019 | | |
| CN | 110150760 A | 8/2019 | | |
| CN | 209255084 U | 8/2019 | | |
| CN | 105876870 B | 11/2019 | | |
| CN | 209900345 U | 1/2020 | | |
| CN | 210076566 U | 2/2020 | | |
| CN | 110946315 A | 4/2020 | | |
| DE | 2656370 A1 | 6/1978 | | |
| DE | 2656370 B2 | 11/1978 | | |
| DE | 2656370 C3 | 7/1979 | | |
| DE | 100 51 762 A1 | 5/2002 | | |
| DE | 10122065 A1 | 12/2002 | | |
| EP | 0 258 637 A1 | 3/1988 | | |
| EP | 0 295 122 A2 | 12/1988 | | |
| EP | 0 258 637 B1 | 6/1990 | | |
| EP | 0 442 510 A1 | 8/1991 | | |
| EP | 0 442 510 B1 | 1/1995 | | |
| EP | 0 516 565 B1 | 4/1996 | | |
| EP | 0 824 927 A | 2/1998 | | |
| EP | 0 833 695 A1 | 4/1998 | | |
| EP | 0 845 220 A1 | 6/1998 | | |
| EP | 0 893 071 A1 | 1/1999 | | |
| EP | 0 970 627 A1 | 1/2000 | | |
| EP | 1083952 81 | 12/2005 | | |
| EP | 1 618 803 B1 | 12/2008 | | |
| EP | 3 088 007 A1 | 11/2016 | | |
| EP | 3 192 381 A1 | 7/2017 | | |
| EP | 3 278 678 A1 | 2/2018 | | |
| EP | 3 298 912 A1 | 3/2018 | | |
| EP | 3 088 007 B1 | 11/2018 | | |
| EP | 3 434 118 A1 | 1/2019 | | |
| EP | 3 469 927 A1 | 4/2019 | | |
| EP | 3 505 098 | 7/2019 | | |
| EP | 3 520 634 A1 | 8/2019 | | |
| EP | 3 278 678 B1 | 10/2019 | | |
| EP | 3 545 778 A1 | 10/2019 | | |
| EP | 3 574 902 A1 | 12/2019 | | |
| EP | 3 837 999 A1 | 6/2021 | | |
| FR | 3043576 A1 | 5/2017 | | |
| FR | 3064502 A1 | 5/2018 | | |
| GB | 1 528 391 A | 10/1978 | | |
| GB | 2566766 A | 3/2019 | | |
| GB | 2570439 A | 7/2019 | | |
| JP | 05093575 U | 12/1993 | | |
| JP | 2579614 Y2 | 8/1998 | | |
| JP | 2001069963 A | 3/2001 | | |
| JP | 2005288400 A | 10/2005 | | |
| JP | 2008-104966 A | 5/2008 | | |
| JP | 2019521671 A | 8/2019 | | |
| JP | 2020535846 A | 12/2020 | | |
| KR | 20120107219 A | 10/2012 | | |
| KR | 10-2013-0095024 | 8/2013 | | |
| WO | WO 92/21332 A1 | 12/1992 | | |
| WO | WO9309881 | 5/1993 | | |
| WO | WO 2000/050111 A | 8/2000 | | |
| WO | WO 2002/055131 A2 | 7/2002 | | |
| WO | WO 2002/094342 A2 | 11/2002 | | |
| WO | WO 2003/055486 A | 7/2003 | | |
| WO | WO 2003/0101454 A | 12/2003 | | |
| WO | WO 2007/083088 A1 | 7/2007 | | |
| WO | WO 2008/076717 A1 | 6/2008 | | |
| WO | WO 2009/096346 A1 | 8/2009 | | |
| WO | WO 2012/062600 A1 | 5/2012 | | |
| WO | WO 2012/138835 A2 | 10/2012 | | |
| WO | WO 2013/028934 A1 | 2/2013 | | |
| WO | WO 2014/182736 A1 | 11/2014 | | |
| WO | WO 2015/128499 A1 | 3/2015 | | |
| WO | WO2015/084544 A1 | 6/2015 | | |
| WO | WO 2015/115006 A1 | 8/2015 | | |
| WO | WO 2016/010864 A1 | 1/2016 | | |
| WO | WO 2016/116386 | 7/2016 | | |
| WO | WO 2016/118941 A1 | 7/2016 | | |
| WO | WO 2016/175720 A1 | 11/2016 | | |
| WO | WO 2016/196915 A1 | 12/2016 | | |
| WO | WO 2017/076590 A1 | 5/2017 | | |
| WO | WO 2017/108268 A1 | 6/2017 | | |
| WO | WO 2017/143515 A1 | 8/2017 | | |
| WO | WO 2017/177159 A3 | 10/2017 | | |
| WO | WO 2017/197704 A1 | 11/2017 | | |
| WO | WO 2017/206022 A1 | 12/2017 | | |
| WO | WO 2017/215221 A1 | 12/2017 | | |
| WO | WO-2017206212 A1 * | 12/2017 | ............ | A24B 15/167 |
| WO | WO-2018000761 A1 * | 1/2018 | | |
| WO | WO-2018000829 A1 * | 1/2018 | ............ | A24F 40/05 |
| WO | WO2018/027189 A2 | 2/2018 | | |
| WO | WO-2018032672 A1 * | 2/2018 | ............ | A24F 47/00 |
| WO | WO 2018/040380 A1 | 3/2018 | | |
| WO | WO 2018/041106 A1 | 3/2018 | | |
| WO | WO-2018058884 A1 * | 4/2018 | ............ | A24F 40/05 |
| WO | WO 2018/113669 A1 | 6/2018 | | |
| WO | WO 2018/115781 A1 | 6/2018 | | |
| WO | WO 2018/163366 A1 | 9/2018 | | |
| WO | WO 2018/188616 A1 | 10/2018 | | |
| WO | WO 2018/188638 A1 | 10/2018 | | |
| WO | WO 2018/211252 A1 | 11/2018 | | |

(56) References Cited

FOREIGN PATENT DOCUMENTS

| | | |
|---|---|---|
| WO | WO 2018/220586 A2 | 12/2018 |
| WO | WO2018/220599 A1 | 12/2018 |
| WO | WO 2019/048749 A1 | 3/2019 |
| WO | WO 2019/052506 A1 | 3/2019 |
| WO | WO 2019/052574 A1 | 3/2019 |
| WO | WO 2019/069160 A1 | 4/2019 |
| WO | WO 2019/138076 A1 | 7/2019 |
| WO | WO 2019/198688 | 10/2019 |
| WO | WO 2019/238064 | 12/2019 |
| WO | WO 2020/019030 A1 | 1/2020 |
| WO | WO 2020/048437 A1 | 3/2020 |
| WO | WO 2020/057636 A2 | 3/2020 |
| WO | WO2020187138 A1 | 9/2020 |
| WO | WO 2020/225534 A1 | 11/2020 |
| WO | WO 2020/254862 A1 | 12/2020 |
| WO | WO 2021/036827 A1 | 3/2021 |

OTHER PUBLICATIONS

English translation for WO 2018000829, machine translated by Search Clarivate Analytics, translated on Mar. 24, 2023.*
English translation for WO 2018000761, machine translated by Search Clarivate Analytics, translated on Mar. 24, 2023.*
English translation for WO 2018058884, machine translated by Search Clarivate Analytics, translated on Mar. 24, 2023.*
English translation for WO 2017/206212, machine translated by Search Clarivate Analytics, translated on Mar. 24, 2023.*
English translation for WO 2018/032672, machine translated by Search Clarivate Analytics, translated on Mar. 24, 2023.*
Japanese Exam Report dated Nov. 1, 2022 for co-pending Japanese application No. 2022-545772(with translation).
Intent to Grant Patent dated May 24, 2022 for EPO Application No. 20214228.7.
ISR and Written Opinion dated Mar. 10, 2022 for Intl. Appl. No. PCT/GB2021053312.
ISR and Written Opinion dated Mar. 10, 2022 for Intl. Appl. No. PCT/GB2021053311.
ISR and Written Opinion dated Mar. 22, 2022 for Intl. Appl. No. PCT/GB2021053316.
UKIPO Search Report dated Nov. 24, 2021 for Application No. GB2111261.0.
UKIPO Search Report dated Nov. 24, 2021 for Application No. GB2113658.5.
UKIPO Search Report dated Nov. 24, 2021 for Application No. GB2113623.9.
EPO Search Report dated Nov. 12, 2021 for corresponding European Application No. 19870060.1.
EPO Search Report dated Oct. 27, 2021 for corresponding European Application No. 19870058.5.
International Search Report and Written Opinion for International Appl. No. PCT/GB2021/050842 dated Jul. 5, 2021.
International Search Report and Written Opinion for International Appl. No. PCT/GB2021/050817 dated Jun. 17, 2021.
UKIPO Search Report for UK Appl. No. GB2104872.3 dated Jun. 25, 2021.
EPO Search Report and Search Opinion for International Appl. No. PCT/IB2019/060812 dated Jun. 22, 2021.
Extended European Search Report and Search Opinion for corresponding EP Application No. 20214228.7 dated May 26, 2021.
International Search Report and Written Opinion for International Appl. No. PCT/IB2019/055192 dated Apr. 29, 2020.
International Search Report for corresponding PCT Appl. No. PCT/GB2020/053219 dated Mar. 31, 2021.
Written Opinion dated Nov. 10, 2020 for corresponding International Application No. PCT/IB2019/060812.
International Search Report dated Nov. 10, 2020 for corresponding International Application No. PCT/IB2019/060812.
EPO Search Report dated Nov. 9, 2020 for corresponding EPO Application No. 19870059.3 (PCT/IB2019/060808).
Written Opinion dated Nov. 4, 2020 for corresponding International Application No. PCT/IB2019/060806.
International Search Report dated Nov. 4, 2020 for corresponding International Application No. PCT/IB2019/060806.
Written Opinion dated Nov. 4, 2020 for corresponding International Application No. PCT/IB2019/060807.
International Search Report dated Nov. 4, 2020 for corresponding International Application No. PCT/IB2019/060807.
Written Opinion dated Oct. 20, 2020 for corresponding International Application No. PCT/IB2019/060811.
International Search Report dated Oct. 20, 2020 for corresponding International Application No. PCT/IB2019/060811.
ISR and Written Opinion dated Oct. 20, 2020 for International Application No. PCT/IB2019/060809.
Written Opinion dated Oct. 19, 2020 for corresponding International Application No. PCT/IB2019/060810.
International Search Report dated Oct. 19, 2020 for corresponding International Application No. PCT/IB2019/060810.
EPO Search Report dated Sep. 16, 2020 for corresponding EPO Application No. 20/168,231.
Extended EPO Search Report dated Sep. 15, 2020 for corresponding EPO Application No. 20168938.7.
Written Opinion dated Jun. 25, 2020 for corresponding International Application No. PCT/IB2019/060808.
International Search Report dated Jun. 25, 2020 for corresponding International Application No. PCT/IB2019/060808.
Written Opinion dated Apr. 29, 2020 for corresponding International Application No. PCT/1B2019/055192.
International Search Report dated Apr. 29, 2020 for corresponding International Application No. PCT/IB2019/055192.
EPO search report dated Sep. 20, 2017 for corresponding EPO Application No. 20168245.7.
EPO Supplementary Search Report for EPO Application No. EP 3 278 678 A4 dated Oct. 4, 2018.
International Search Report for International Appl. No. WO 2017/177159 A3 dated Sep. 26, 2017.
EPO Supplementary Search Report for EPO Application No. EP 1 618 803 A4 dated Jul. 27, 2007.
European Search Report dated Nov. 15, 2022 for co-pending European application No. 22181106.0.

* cited by examiner

MIST INHALER DEVICES

CROSS REFERENCES TO RELATED APPLICATIONS

The present application is a continuation of U.S. patent application Ser. No. 17/122,025, filed Dec. 15, 2020, which claims the benefit of priority to and incorporates by reference herein the entirety of each of: International patent application no. PCT/IB2019/060808, filed on Dec. 15, 2019; International patent application no. PCT/IB2019/060810, filed on Dec. 15, 2019; International patent application no. PCT/IB2019/060811, filed on Dec. 15, 2019; International patent application no. PCT/IB2019/060812, filed on Dec. 15, 2019; European patent application no. 20168245.7, filed on Apr. 6, 2020; European patent application no. 20168231.7, filed on 6 Apr. 2020; and European patent application no. 20168938.7, filed on Apr. 9, 2020.

FIELD

The present invention relates to mist inhaler devices. The present invention more particularly relates to ultrasonic mist inhaler devices for atomising a liquid by ultrasonic vibrations.

BACKGROUND

Mist inhaler devices are used for generating a mist or vapour for inhalation by a user. The mist may contain a drug or medicine which is inhaled by a user and absorbed into the user's blood stream.

In particular, mist inhaler devices or electronic vaporising inhalers are becoming popular among smokers who want to avoid the tar and other harsh chemicals associated with so traditional cigarettes and who wish to satisfy the craving for nicotine. Electronic vaporising inhalers may contain liquid nicotine, which is typically a mixture of nicotine oil, a solvent, water, and often flavouring. When the user draws, or inhales, on the electronic vaporising inhaler, the liquid nicotine is drawn into a vaporiser where it is heated into a vapour. As the user draws on the electronic vaporising inhaler, the vapour containing the nicotine is inhaled. Such electronic vaporising inhalers may have medical purpose.

Electronic vaporising inhalers and other vapour inhalers typically have similar designs. Most electronic vaporising inhalers feature a liquid nicotine reservoir with an interior membrane, such as a capillary element, typically cotton, that holds the liquid nicotine so as to prevent leaking from the reservoir. Nevertheless, these cigarettes are still prone to leaking because there is no obstacle to prevent the liquid from flowing out of the membrane and into the mouthpiece. A leaking electronic vaporising inhaler is problematic for several reasons. As a first disadvantage, the liquid can leak into the electronic components, which can cause serious damage to the device. As a second disadvantage, the liquid can leak into the electronic vaporising inhaler mouthpiece, and the user may inhale the unvapourised liquid.

Electronic vaporising inhalers are also known for providing inconsistent doses between draws. The aforementioned leaking is one cause of inconsistent doses because the membrane may be oversaturated or undersaturated near the vaporiser. If the membrane is oversaturated, then the user may experience a stronger than desired dose of vapour, and if the membrane is undersaturated, then the user may experience a weaker than desired dose of vapour. Additionally, small changes in the strength of the user's draw may provide stronger or weaker doses. Inconsistent dosing, along with leaking, can lead to faster consumption of the vaping Additionally, conventional electronic vaporising inhalers tend to rely on inducing high temperatures of a metal heating component configured to heat a liquid in the e-cigarette, thus vaporising the liquid that can be breathed in. Problems with conventional electronic vaporising inhalers may include the possibility of burning metal and subsequent breathing in of the metal along with the burnt liquid. In addition, some may not prefer the burnt smell caused by the heated liquid.

Thus, a need exists in the art for improved mist inhaler devices which seek to address at least some of the problems described herein.

SUMMARY

According to one aspect, there is provided a mist inhaler device for generating a mist for inhalation by a user, the device comprising:
  a mist generator device which incorporates:
    a mist generator housing which is elongate and comprises an air inlet port and a mist outlet port;
    a liquid chamber provided within the mist generator housing, the liquid chamber for containing a liquid to be atomised;
    a sonication chamber provided within the mist generator housing;
    a capillary element extending between the liquid chamber and the sonication chamber such that a first portion of the capillary element is within the liquid chamber and a second portion of the capillary element is within the sonication chamber;
    an ultrasonic transducer having a generally planar atomisation surface which is provided within the sonication chamber, the ultrasonic transducer being mounted within the mist generator housing such that the plane of the atomisation surface is substantially parallel with a longitudinal length of the mist generator housing, wherein part of the second portion of the capillary element is superimposed on part of the atomisation surface, and wherein the ultrasonic transducer is configured to vibrate the atomisation surface to atomise a liquid carried by the second portion of the capillary element to generate a mist comprising the atomised liquid and air within the sonication chamber; and
    an airflow arrangement which provides an air flow path between the air inlet port, the sonication chamber and the air outlet port such that a user drawing on the mist outlet port draws air through the inlet port, through the sonication chamber and out through the mist outlet port, with the mist generated in the sonication chamber being carried by the air out through the mist outlet port for inhalation by the user,
    wherein the mist inhaler device further comprises:
  a driver device which incorporates:
    a battery;
    an AC driver for converting a voltage from the battery into an AC drive signal at a predetermined frequency to drive the ultrasonic transducer;
    an active power monitoring arrangement for monitoring the active power used by the ultrasonic transducer when the ultrasonic transducer is driven by the AC drive signal, wherein the active power monitoring arrangement provides a monitoring signal which is indicative of an active power used by the ultrasonic transducer;

a processor for controlling the AC driver and for receiving the monitoring signal drive from the active power monitoring arrangement; and a memory storing instructions which, when executed by the processor, cause the processor to:

A. control the AC driver to output an AC drive signal to the ultrasonic transducer at a predetermined sweep frequency;

B. calculate the active power being used by the ultrasonic transducer based on the monitoring signal;

C. control the AC driver to modulate the AC drive signal to maximise the active power being used by the ultrasonic transducer;

D. store a record in the memory of the maximum active power used by the ultrasonic transducer and the sweep frequency of the AC drive signal;

E. repeat steps A-D for a predetermined number of iterations with the sweep frequency incrementing with each iteration such that, after the predetermined number of iterations has occurred, the sweep frequency has been incremented from a start sweep frequency to an end sweep frequency;

F. identify from the records stored in the memory the optimum frequency for the AC drive signal which is the sweep frequency of the AC drive signal at which a maximum active power is used by the ultrasonic transducer; and G. control the AC driver to output an AC drive signal to the ultrasonic transducer at the optimum frequency to drive the ultrasonic transducer to atomise a liquid.

In some examples, the driver device is releasably attached to the mist generator device such that the driver device is separable from the mist generator device.

According to another aspect, there is provided a mist generator device which incorporates:

a mist generator housing which is elongate and comprises an air inlet port and a mist outlet port;

a liquid chamber provided within the mist generator housing, the liquid chamber for containing a liquid to be atomised;

a sonication chamber provided within the mist generator housing;

a capillary element extending between the liquid chamber and the sonication chamber such that a first portion of the capillary element is within the liquid chamber and a second portion of the capillary element is within the sonication chamber;

an ultrasonic transducer having a generally planar atomisation surface which is provided within the sonication chamber, the ultrasonic transducer being mounted within the mist generator housing such that the plane of the atomisation surface is substantially parallel with a longitudinal length of the mist generator housing, wherein part of the second portion of the capillary element is superimposed on part of the atomisation surface, and wherein the ultrasonic transducer is configured to vibrate the atomisation surface to atomise a liquid carried by the second portion of the capillary element to generate a mist comprising the atomised liquid and air within the sonication chamber; and an airflow arrangement which provides an air flow path between the air inlet port, the sonication chamber and the air outlet port such that a user drawing on the mist outlet port draws air through the inlet port, through the sonication chamber and out through the mist outlet port, with the mist generated in the sonication chamber being carried by the air out through the mist outlet port for inhalation by the user.

In some examples, the mist generator device further comprises: a transducer holder which is held within the mist generator housing, the transducer element holds the ultrasonic transducer and retains the second portion of the capillary element superimposed on part of the atomisation surface; and a divider portion which provides a barrier between the liquid chamber and the sonication chamber, wherein the divider portion comprises a capillary aperture through which part of the first portion of the capillary element extends.

In some examples, the transducer holder is of liquid silicone rubber.

In some examples, the liquid silicone rubber has a Shore A 60 hardness.

In some examples, the capillary aperture is an elongate slot having a width of 0.2 mm to 0.4 mm.

In some examples, the capillary element is generally planar with first portion having a generally rectangular shape and the second portion having a partly circular in shape.

In some examples, the capillary element has a thickness of substantially 0.28 mm.

In some examples, the capillary element comprises a first part and a second part which are superimposed on one another such that the capillary element has two layers.

In some examples, the capillary element is of at least 75% bamboo fibre.

In some examples, the capillary element is 100% bamboo fibre.

In some examples, the airflow arrangement is configured to change the direction of a flow of air along the air flow path such that the flow of air is substantially perpendicular to the atomisation surface of the ultrasonic transducer as the flow of air passes into the sonication chamber.

In some examples, the change of direction of the flow of air is substantially 90°.

In some examples, the airflow arrangement provides an air flow path having an average cross-sectional area of substantially 11.5 mm$^2$.

In some examples, the mist generator device further comprises: at least one absorbent element which is provided adjacent the mist outlet port to absorb liquid at the mist outlet port.

In some examples, each absorbent element is of bamboo fibre.

In some examples, the mist generator housing is at least partly of a heterophasic copolymer.

In some examples, the heterophasic copolymer is polypropylene.

In some examples, the ultrasonic transducer is circular and has a diameter of substantially 16 mm.

In some examples, the liquid chamber contains a liquid having a liquid viscosity between 1.05 Pa·s and 1.412 Pa·s and a liquid density between 1.1 g/ml and 1.3 g/ml.

In some examples, the liquid chamber contains a liquid comprising a nicotine levulinate salt at a 1:1 molar ratio.

In some examples, the mist generator device further comprises: an identification arrangement which is provided on the mist generator housing, the identification arrangement comprising: an integrated circuit having a memory which stores a unique identifier for the mist generator device; and an electrical connection which provides an electronic interface for communication with the integrated circuit.

In some examples, the memory of the integrated circuit stores a record of the state of the mist generator device which is indicative of at least one of the historic use of the mist generator device or the volume of a liquid within the liquid chamber.

According to one aspect, there is provided a driver device for a mist inhaler device, the device comprising:

a battery;

an AC driver for converting a voltage from the battery into an AC drive signal at a predetermined frequency to drive an ultrasonic transducer;

an active power monitoring arrangement for monitoring the active power used by the ultrasonic transducer when the ultrasonic transducer is driven by the AC drive signal, wherein the active power monitoring arrangement provides a monitoring signal which is indicative of an active power used by the ultrasonic transducer;

a processor for controlling the AC driver and for receiving the monitoring signal drive from the active power monitoring arrangement; and a memory storing instructions which, when executed by the processor, cause the processor to:

A. control the AC driver to output an AC drive signal to the ultrasonic transducer at a predetermined sweep frequency;

B. calculate the active power being used by the ultrasonic transducer based on the monitoring signal;

C. control the AC driver to modulate the AC drive signal to maximise the active power being used by the ultrasonic transducer;

D. store a record in the memory of the maximum active power used by the ultrasonic transducer and the sweep frequency of the AC drive signal;

E. repeat steps A-D for a predetermined number of iterations with the sweep frequency incrementing with each iteration such that, after the predetermined number of iterations has occurred, the sweep frequency has been incremented from a start sweep frequency to an end sweep frequency;

F. identify from the records stored in the memory the optimum frequency for the AC drive signal which is the sweep frequency of the AC drive signal at which a maximum active power is used by the ultrasonic transducer; and G. control the AC driver to output an AC drive signal to the ultrasonic transducer at the optimum frequency to drive the ultrasonic transducer to atomise a liquid.

In some examples, the active power monitoring arrangement comprises: a current sensing arrangement for sensing a drive current of the AC drive signal driving the ultrasonic transducer, wherein the active power monitoring arrangement provides a monitoring signal which is indicative of the sensed drive current.

In some examples, the current sensing arrangement comprises: an Analog-to-Digital Converter which converts the sensed drive current into a digital signal for processing by the processor.

In some examples, the memory stores instructions which, when executed by the processor, cause the processor to: repeat steps A-D with the sweep frequency being incremented from a start sweep frequency of 2900 kHz to an end sweep frequency of 2960 kHz.

In some examples, the memory stores instructions which, when executed by the processor, cause the processor to: repeat steps A-D with the sweep frequency being incremented from a start sweep frequency of 2900 kHz to an end sweep frequency of 3100 kHz.

In some examples, the memory stores instructions which, when executed by the processor, cause the processor to: in step G, control the AC driver to output an AC drive signal to the ultrasonic transducer at frequency which is shifted by a predetermined shift amount from the optimum frequency.

In some examples, the predetermined shift amount is between 1-10% of the optimum frequency.

In some examples, the battery is a 3.7V DC Li—Po battery.

In some examples, the driver device further comprises: a pressure sensor for sensing a flow of air along a driver device flow path which extends through the driver device.

In some examples, the driver device further comprises: a wireless communication system which is in communication with the processor, the wireless communication system being configured to transmit and receive data between the driver device and a computing device.

In some examples, the driver device further comprises: a driver device housing which is at least partly of metal, wherein the driver device housing houses the battery, the processor, the memory, the active power monitoring arrangement and the AC driver, and wherein the driver device housing comprises a recess for receiving and retaining part of the mist generator device.

In some examples, the AC driver modulates the AC drive signal by pulse width modulation to maximise the active power being used by the ultrasonic transducer.

It is noted that the expression "mist" used in the following disclosure means the liquid is not heated as usually in traditional inhalers known from the prior art. In fact, traditional inhalers use heating elements to heat the liquid above its boiling temperature to produce a vapour, which is different from a mist.

In fact, when sonicating liquids at high intensities, the sound waves that propagate into the liquid media result in alternating high-pressure (compression) and low-pressure (rarefaction) cycles, at different rates depending on the frequency. During the low-pressure cycle, high-intensity ultrasonic waves create small vacuum bubbles or voids in the liquid. When the bubbles attain a volume at which they can no longer absorb energy, they collapse violently during a high-pressure cycle. This phenomenon is termed cavitation. During the implosion, very high pressures are reached locally. At cavitation, broken capillary waves are generated, and tiny droplets break the surface tension of the liquid and are quickly released into the air, taking mist form.

The following will explain more precisely the cavitation phenomenon.

When the liquid is atomised by ultrasonic vibrations, micro water bubbles are produced in the liquid.

The bubble production is a process of formation of cavities created by the negative pressure generated by intense ultrasonic waves generated by the means of ultrasonic vibrations.

High intensity ultrasonic sound waves leading to rapid growth of cavities with relatively low and negligible reduction in cavity size during the positive pressure cycle.

Ultrasound waves, like all sound waves, consist of cycles of compression and expansion. When in contact with a liquid, Compression cycles exert a positive pressure on the liquid, pushing the molecules together. Expansion cycles exert a negative pressure, pulling the molecules away from another.

Intense ultrasound waves create regions of positive pressure and negative pressure. A cavity can form and grow during the episodes of negative pressure. When the cavity attains a critical size, the cavity implodes.

The amount of negative pressure needed depends on the type and purity of the liquid. For truly pure liquids, tensile strengths are so great that available ultrasound generators cannot produce enough negative pressure to make cavities. In pure water, for instance, more than 1,000 atmospheres of negative pressure would be required, yet the most powerful ultrasound generators produce only about 50 atmospheres of negative pressure. The tensile strength of liquids is reduced by the gas trapped within the crevices of the liquid particles. The effect is analogous to the reduction in strength that occurs from cracks in solid materials. When a crevice filled with gas is exposed to a negative-pressure cycle from a sound wave, the reduced pressure makes the gas in the crevice expand until a small bubble is released into solution.

However, a bubble irradiated with ultrasound continually absorbs energy from alternating compression and expansion cycles of the sound wave. These cause the bubbles to grow and contract, striking a dynamic balance between the void inside the bubble and the liquid outside. In some cases, ultrasonic waves will sustain a bubble that simply oscillates in size. In other cases, the average size of the bubble will increase.

Cavity growth depends on the intensity of sound. High-intensity ultrasound can expand the cavity so rapidly during the negative-pressure cycle that the cavity never has a chance to shrink during the positive-pressure cycle. In this process, cavities can grow rapidly in the course of a single cycle of sound.

For low-intensity ultrasound the size of the cavity oscillates in phase with the expansion and compression cycles. The surface of a cavity produced by low-intensity ultrasound is slightly greater during expansion cycles than during compression cycles. Since the amount of gas that diffuses in or out of the cavity depends on the surface area, diffusion into the cavity during expansion cycles will be slightly greater than diffusion out during compression cycles. For each cycle of sound, then, the cavity expands a lithe more than it shrinks. Over many cycles the cavities will grow slowly.

It has been noticed that the growing cavity can eventually reach a critical size where it will most efficiently absorb energy from the ultrasound. The critical size depends on the frequency of the ultrasound wave. Once a cavity has experienced a very rapid growth caused by high intensity ultrasound, it can no longer absorb energy as efficiently from the sound waves. Without this energy input the cavity can no longer sustain itself. The liquid rushes in and the cavity implodes due to a non-linear response.

The energy released from the implosion causes the liquid to be fragmented into microscopic particles which are dispersed into the air as mist.

The equation for description of the above non-linear response phenomenon may be described by the "Rayleigh-Plesset" equation. This equation can be derived from the "Navier-Stokes" equation used in fluid dynamics.

The inventors approach was to rewrite the "Rayleigh-Plesset" equation in which the bubble volume, V, is used as the dynamic parameter and where the physics describing the dissipation is identical to that used in the more classical form where the radius is the dynamic parameter.

The equation used derived as follows:

$$\frac{\left|\frac{1}{c^2}\frac{\delta^2\phi}{\delta t^2}\right|}{V^2\phi} \sim \left(\frac{R}{\lambda}\right)^2 \ll 1$$

-continued $$\frac{1}{4\pi}\left(\frac{4\pi}{3V}\right)^{\frac{1}{3}}\left(\ddot{V} - \frac{\dot{V}^2(t)}{6V}\right) =$$

$$\frac{1}{\rho_0}\left(\left(p_0 + 2\sigma\left(\frac{4\pi}{3V_0}\right)^{\frac{1}{3}} - p_V\right)\left(\frac{V_0}{V}\right)^\kappa + p_V - 2\sigma\left(\frac{4\pi}{3V}\right)^{\frac{1}{3}} - p_0 - P(t)\right)$$

wherein:
V is the bubble volume
$V_0$ is the equilibrium bubble volume
$\rho_0$ is the liquid density (assumed to be constant)
σ is the surface tension
$p_V$ is the vapour pressure
$p_0$ is the static pressure in the liquid just outside the bubble wall
κ is the polytropic index of the gas
t is the time
R(t) is the bubble radius
P(t) is the applied pressure
c is the speed sound of the liquid
φ is the velocity potential
λ is the wavelength of the insonifying field In the ultrasonic mist inhaler; the liquid has a liquid viscosity between 1.05 Pa·sec and 1.412 Pa·sec By solving the above equation with the right parameters of viscosity, density and having a desired target bubble volume of liquid spray into the air, it has been found that the frequency range of 2.8 MHz to 3.2 MHz for liquid viscosity range of 1.05 Pa·s and 1,412 Pa·s produce a bubble volume of about 0.25 to 0.5 microns.

The process of ultrasonic cavitation has a significant impact on the nicotine concentration in the produced mist.

No heating elements are involved, thereby leading to no burnt elements and reducing second-hand smoke effects.

In some examples, said liquid comprises 57-70% (w/w) vegetable glycerine and 30-43% (w/w) propylene glycol, said propylene glycol including nicotine and optionally flavourings, In the ultrasonic mist inhaler, a capillary element may extend between the sonication chamber and the liquid chamber.

In the ultrasonic mist inhaler, the capillary element is a material at east partly in bamboo fibres.

The capillary element allows a high absorption capacity, a high rate of absorption as well as a high fluid-retention ratio.

It was found that the inherent properties of the proposed material used for the capillarity have a significant impact on the efficient functioning of the ultrasonic mist inhaler.

Further, inherent properties of the proposed material include a good hygroscopicity while maintaining a good permeability. This allows the drawn liquid to efficiently permeate the capillary while the observed high absorption capacity allows the retention of a considerable amount of liquid thus allowing the ultrasonic mist inhaler to last for a longer time when compared with the other products available in the market.

Another significant advantage of using the bamboo fibres is the naturally occurring antimicrobial bio-agent namely "Kun" inherently present within the bamboo fibre making it antibacterial, anti-fungal and odour resistant, making it suitable for medical applications.

The inherent properties have been verified using numerical analysis regarding the benefits of the bamboo fibre for sonication.

The following formulae have been tested with bamboo fibres material and others material such cotton, paper, or other fibre strands for the use as capillary element and demonstrates that bamboo fibres have much better properties for the use in sonication:

$$C = A + \frac{T}{W_f} - \frac{1}{P_f} + (1 - \alpha)\frac{V_d}{W_f}$$

wherein:

C (cc/gm of fluid/gm) is the volume per mass of the liquid absorbed divided by the dry mass of the capillary element, A ($cm^2$) is the total surface area of the capillary element T (cm) is the thickness of the capillary element, $W_f$ (gm) is the mass of the dry capillary element, $P_f$ (cc/g·sec) is the density of the dry capillary element, $\alpha$ is the ratio of increase in volume of capillary element upon wetting to the volume of liquid diffused in the capillary element, $V_d$ (cc) is the amount of liquid diffused in the capillary element, $$\text{Absorbent Rate, } Q = \frac{\pi r \gamma 1 \cos\theta}{2\eta} \cdot \left(\frac{T}{W_f} - \frac{1}{AP_f}\right)$$

Q (cc/sec) is the amount of liquid absorbed per unit time, r (cm) is the radius of the pores within the capillary element, $\gamma$ (N/m) is the surface tension of the liquid, $\theta$ (degrees) is the angle of contact of the fibre, $\eta$ ($m^2$/sec) is the viscosity of the fluid.

In the ultrasonic mist inhaler, the capillary element may be a material at least partly in bamboo fibres.

In the ultrasonic mist inhaler, the capillary element material may be 100% bamboo fibre.

Extensive testing has concluded that a 100% pure bamboo fibre is the most optimal choice for sonication.

In the ultrasonic mist inhaler, the capillary element material may be at least 75% bamboo fibre and, optionally, 25% cotton.

Capillary element from 100% pure bamboo fibre or with a high percentage of bamboo fibres demonstrates a high absorption capacity as well as improved fluid transmission making it an optimal choice for the application of the ultrasonic mist inhaler.

In the ultrasonic mist inhaler, the capillary element may have a flat shape.

In the ultrasonic mist inhaler, the capillary element may comprise a central portion and a peripheral portion.

In the ultrasonic mist inhaler, the peripheral portion may have an L-shape cross section extending down to the liquid chamber. In the ultrasonic mist inhaler, the central portion may have a U-shape cross section extending down to the sonication chamber.

The ultrasonic mist inhaler according to one example, wherein said liquid to be received in the liquid chamber comprises 57-70% (w/w) vegetable glycerin and 30-43% (w/w) propylene glycol, said propylene glycol including nicotine and flavourings.

An ultrasonic mist inhaler or a personal ultrasonic atomiser device, comprising:

a liquid reservoir structure comprising a liquid chamber or cartridge adapted to receive liquid to be atomised, a sonication chamber in fluid communication with the liquid chamber or cartridge, wherein said liquid to be received in the liquid chamber comprises 57-70% (w/w) vegetable glycerin and 30-43% (w/w) propylene glycol, said propylene glycol including nicotine and flavourings.

BRIEF DESCRIPTION OF THE DRAWINGS

So that the present invention may be more readily understood, embodiments of the present invention will now be described, by way of example, with reference to the accompanying drawings, in which:

FIG. 1 is an exploded view of components of an ultrasonic mist inhaler.

FIG. 2 is an exploded view of components of an inhaler liquid reservoir structure.

FIG. 3 is a cross section view of components of an inhaler liquid reservoir structure.

FIG. 4A is an isometric view of an airflow member of the inhaler liquid reservoir structure according to FIGS. 2 and 3.

FIG. 4B is a cross section view of the airflow member shown in FIG. 4A.

FIG. 5 is schematic diagram showing a piezoelectric transducer modelled as an RLC circuit.

FIG. 6 is graph of frequency versus log impedance of an RLC circuit.

FIG. 7 is graph of frequency versus log impedance showing inductive and capacitive regions of operation of a piezoelectric transducer.

FIG. 8 is flow diagram showing the operation of a frequency controller.

FIG. 9 is a diagrammatic perspective view of a mist inhaler device of this disclosure.

FIG. 10 is a diagrammatic perspective view of a mist inhaler device of this disclosure.

FIG. 11 is a diagrammatic perspective view of a mist generator device of this disclosure.

FIG. 12 is a diagrammatic perspective view of a mist generator device of this disclosure.

FIG. 13 is a diagrammatic exploded perspective view of a mist generator device of this disclosure.

FIG. 14 is a diagrammatic perspective view of a transducer holder of this disclosure.

FIG. 15 is a diagrammatic perspective view of a transducer holder of this disclosure.

FIG. 16 is a diagrammatic perspective view of a capillary element of this disclosure.

FIG. 17 is a diagrammatic perspective view of a capillary element of this disclosure.

FIG. 18 is a diagrammatic perspective view of a transducer holder of this disclosure.

FIG. 19 is a diagrammatic perspective view of a transducer holder of this disclosure.

FIG. 20 is a diagrammatic perspective view of a part of a housing of this disclosure.

FIG. 21 is a diagrammatic perspective view of an absorbent element of this disclosure.

FIG. 22 is a diagrammatic perspective view of a part of a housing of this disclosure.

FIG. 23 is a diagrammatic perspective view of a part of a housing of this disclosure.

FIG. 24 is a diagrammatic perspective view of an absorbent element of this disclosure.

FIG. 25 is a diagrammatic perspective view of a part of a housing of this disclosure.

DETAILED DESCRIPTION

Figure 1:
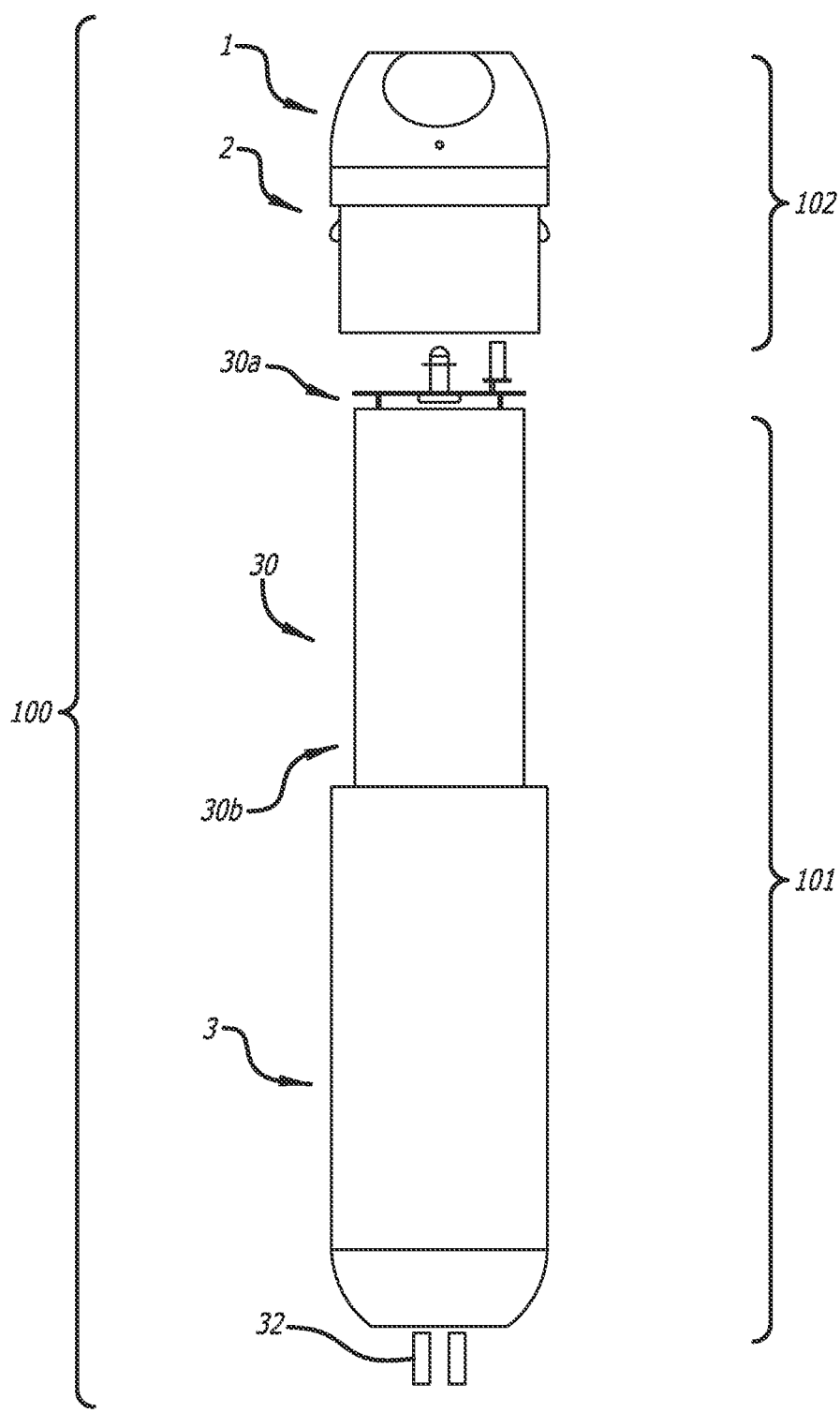

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

The following disclosure provides many different embodiments, or examples, for implementing different features of the provided subject matter. Specific examples of components, concentrations, applications and arrangements are described below to simplify the present disclosure. These are, of course, merely examples and are not intended to be limiting. For example, the attachment of a first feature and a second feature in the description that follows may include embodiments in which the first feature and the second feature are attached in direct contact, and may also include embodiments in which additional features may be positioned between the first feature and the second feature, such that the first feature and the second feature may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The following disclosure describes representative examples. Each example may be considered to be an embodiment and any reference to an "example" may be changed to "embodiment" in the present disclosure.

Some parts of the present disclosure are directed to an electronic vaporising inhaler.

However, other examples are envisioned, such as an inhaler for hookah, flavoured liquids, medicine, and herbal supplements. Additionally, the device can be packaged to look like an object other than a cigarette. For instance, the device could resemble another smoking instrument, such as a pipe, water pipe, or slide, or the device could resemble another non-smoking related object.

Ultrasonic mist inhalers are either disposable or reusable. The term "reusable" as used herein implies that the energy storage device is rechargeable or replaceable or that the liquid is able to be replenished either through refilling or through replacement of the liquid reservoir structure. Alternatively, in some examples reusable electronic device is both rechargeable and the liquid can be replenished.

Conventional electronic vaporising inhaler tend to rely on inducing high temperatures of a metal component configured to heat a liquid in the inhaler, thus vaporising the liquid that can be breathed in. The liquid typically contains nicotine and flavourings blended into a solution of propylene glycol (PG) and vegetable glycerin (VG), which is vaporised via a heating component at high temperatures. Problems with conventional inhaler may include the possibility of burning metal and subsequent breathing in of the metal along with the burnt liquid. In addition, some may not prefer the burnt smell or taste caused by the heated liquid.

FIG. 1 to FIG. 4 illustrates an example of an ultrasonic inhaler comprising a sonication chamber.

FIG. 1 depicts a disposable ultrasonic mist inhaler 100. As can be seen in FIG. 1, the ultrasonic mist inhaler 100 has a cylindrical body with a relatively long length as compared to the diameter. In terms of shape and appearance, the ultrasonic mist inhaler 100 is designed to mimic the look of a typical cigarette. For instance, the inhaler can feature a first portion 101 that primarily simulates the tobacco rod portion of a cigarette and a second portion 102 that primarily simulates a filter. In the disposable example, the first portion and second portion are regions of a single, but-separable device. The designation of a first portion 101 and a second portion 102 is used to conveniently differentiate the components that are primarily contained in each portion.

As can be seen in FIG. 1, the ultrasonic mist inhaler comprises a mouthpiece 1, a liquid reservoir structure 2 and a casing 3. The first portion 101 comprises the casing 3 and the second portion 102 comprises the mouthpiece 1 and the reservoir structure 2. The first portion 101 contains the power supply energy.

An electrical storage device 30 powers the ultrasonic mist inhaler 100. The electrical storage device 30 can be a battery, including but not limited to a lithium-ion, alkaline, zinc-carbon, nickel-metal hydride, or nickel-cadmium battery; a super capacitor; or a combination thereof. In the disposable example, the electrical storage device 30 is not rechargeable, but, in the reusable example, the electrical storage device 30 would be selected for its ability to recharge. In the disposable example, the electrical storage device 30 is primarily selected to deliver a constant voltage over the life of the inhaler 100. Otherwise, the performance of the inhaler would degrade over time. Preferred electrical storage devices that are able to provide a consistent voltage output over the life of the device include lithium-ion and lithium polymer batteries.

The electrical storage device 30 has a first end 30a that generally corresponds to a positive terminal and a second end 30b that generally corresponds to a negative terminal. The negative terminal is extending to the first end 30a.

Because the electrical storage device 30 is located in the first portion 101 and the liquid reservoir structure 2 is located in the second portion 102, the joint needs to provide electrical communication between those components. In the present invention, electrical communication is established using at least an electrode or probe that is compressed together when the first portion 101 is tightened into the second portion 102.

In order for this example to be reusable, the electrical storage device 30 is rechargeable. The casing 3 contains a charging port 32.

The integrated circuit 4 has a proximal end 4a and a distal end 4b. The positive terminal at the first end 30a of the electrical storage device 30 is in electrical communication with a positive lead of the flexible integrated circuit 4. The negative terminal at the second end 30b of the electrical storage device 30 is in electrical communication with a negative lead of the integrated circuit 4. The distal end 4b of the integrated circuit 4 comprises a microprocessor. The microprocessor is configured to process data from a sensor, to control a light, to direct current flow to means of ultrasonic vibrations 5 in the second portion 102, and to terminate current flow after a pre-programmed amount of time.

The sensor detects when the ultrasonic mist inhaler 100 is in use (when the user draws on the inhaler) and activates the microprocessor. The sensor can be selected to detect changes in pressure, air flow, or vibration. In one example, the sensor is a pressure sensor. In the digital device, the sensor takes continuous readings which in turn requires the digital sensor to continuously draw current, but the amount is small and overall battery life would be negligibly affected.

Figure 2:
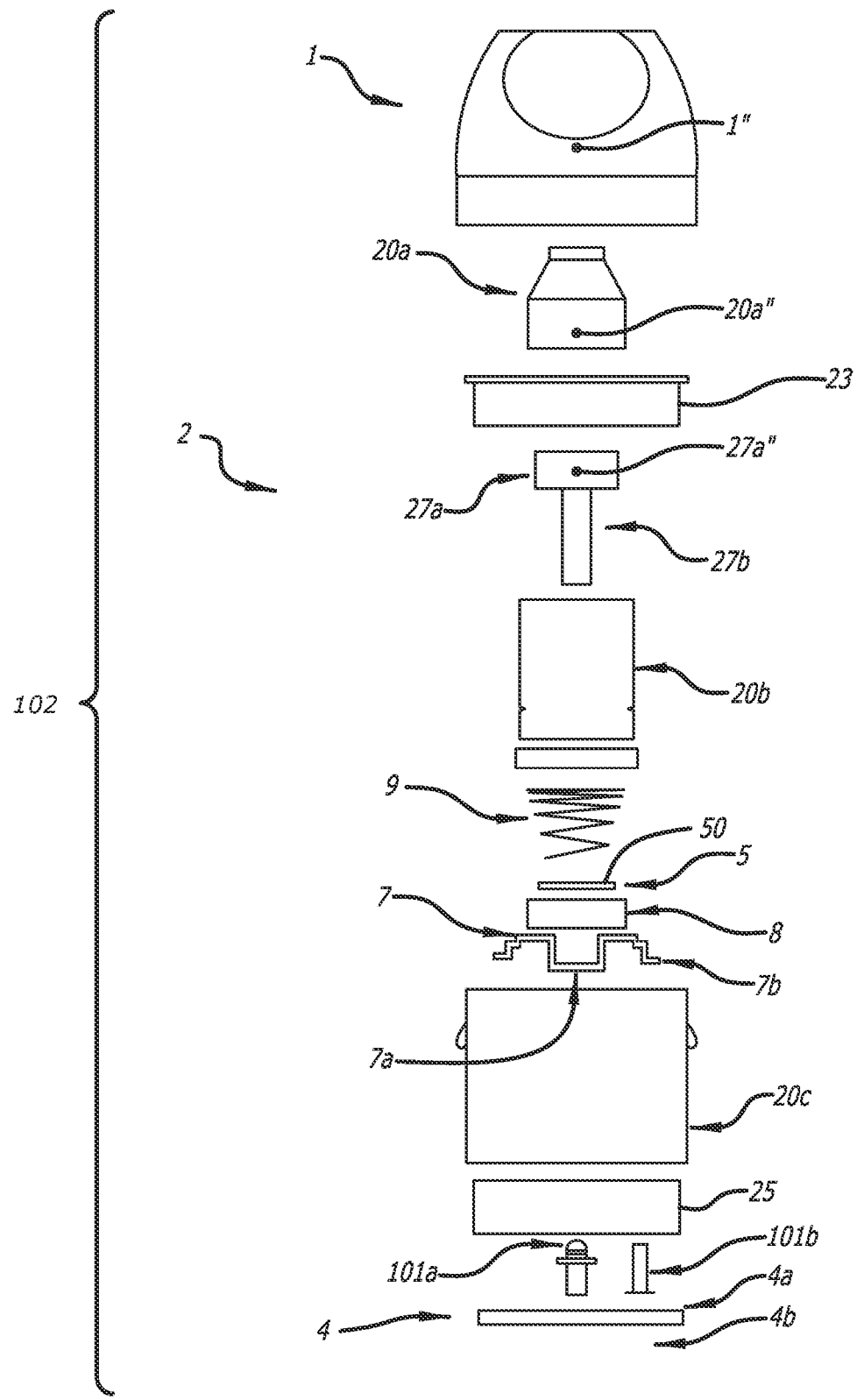
Figure 3:
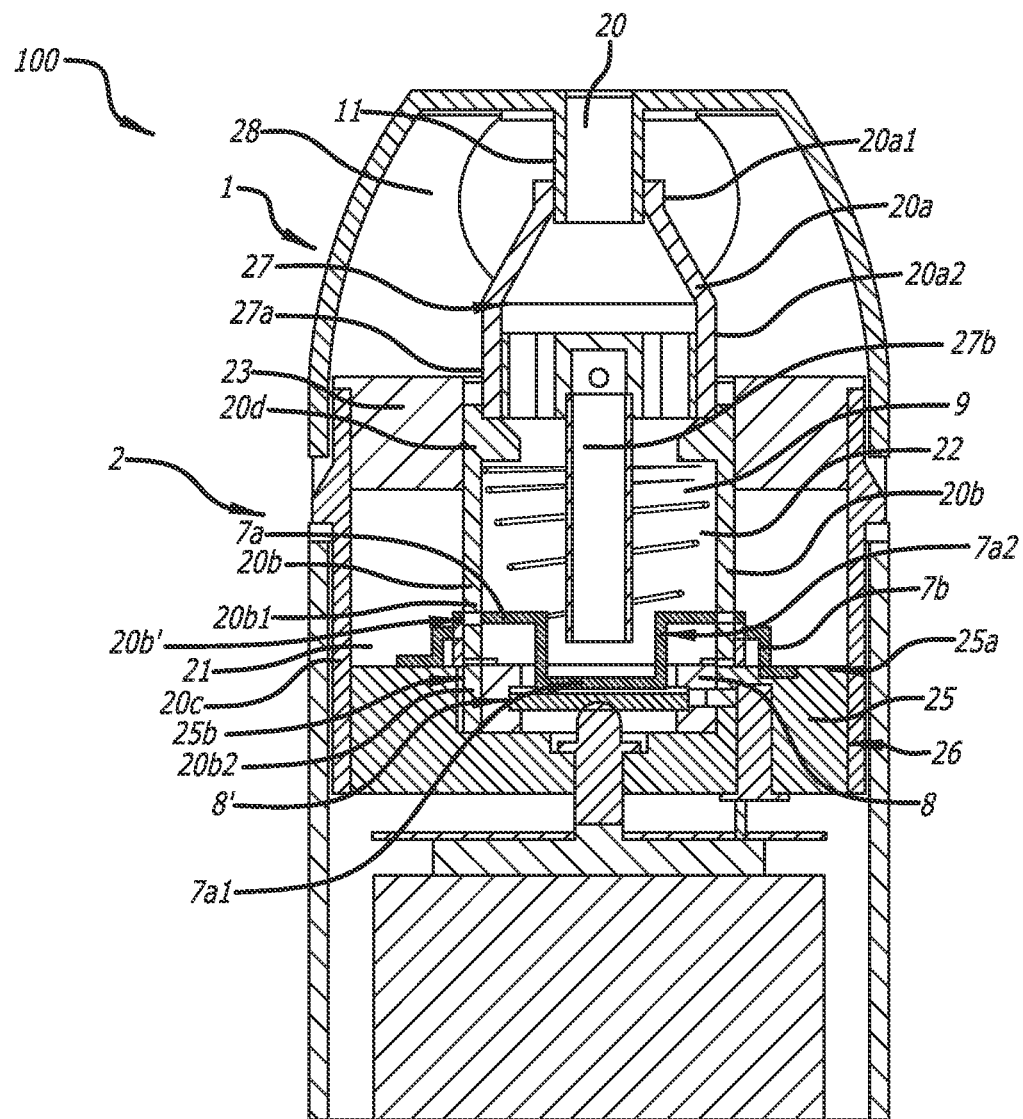

In some examples, the integrated circuit 4 comprises a H bridge, which may be formed by 4 MOSFETs to convert a direct current into an alternate current at high frequency. Referring to FIG. 2 and FIG. 3, illustrations of a liquid reservoir structure 2 according to an example are shown. The liquid reservoir structure 2 comprises a liquid chamber 21 adapted to receive liquid to be atomised and a sonication chamber 22 in fluid communication with the liquid chamber 21.

In the example shown, the liquid reservoir structure 2 comprises an inhalation channel 20 providing an air passage from the sonication chamber 22 toward the surroundings.

As an example of sensor position, the sensor may be located in the sonication chamber 22.

The inhalation channel 20 has a frustoconical element 20a and an inner container 20b.

Figure 4B:
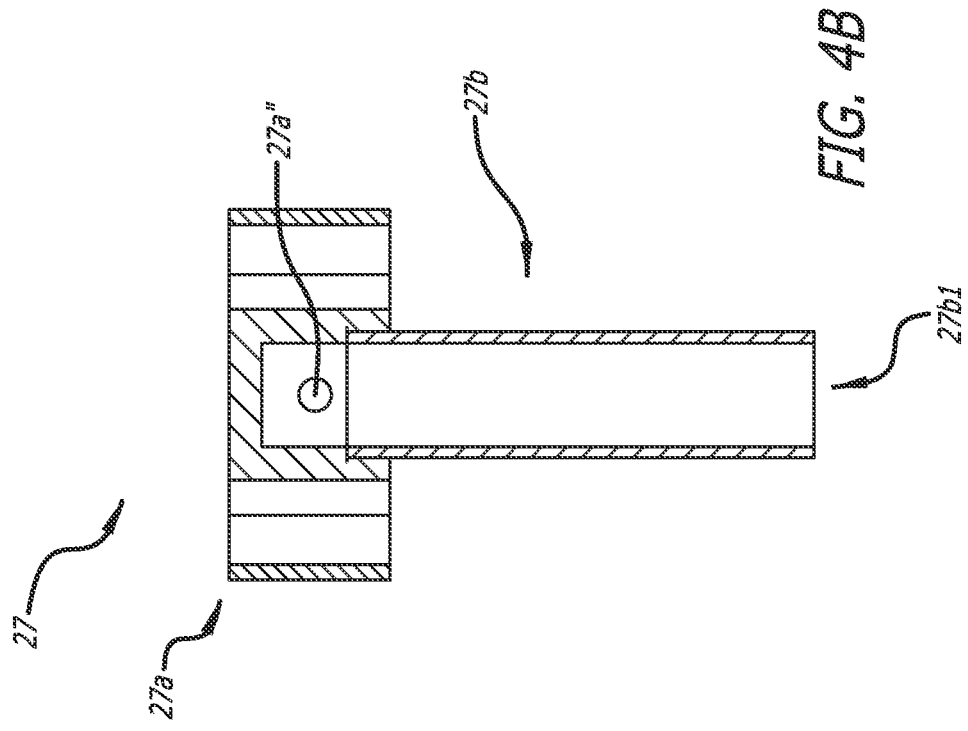
Figure 4A:
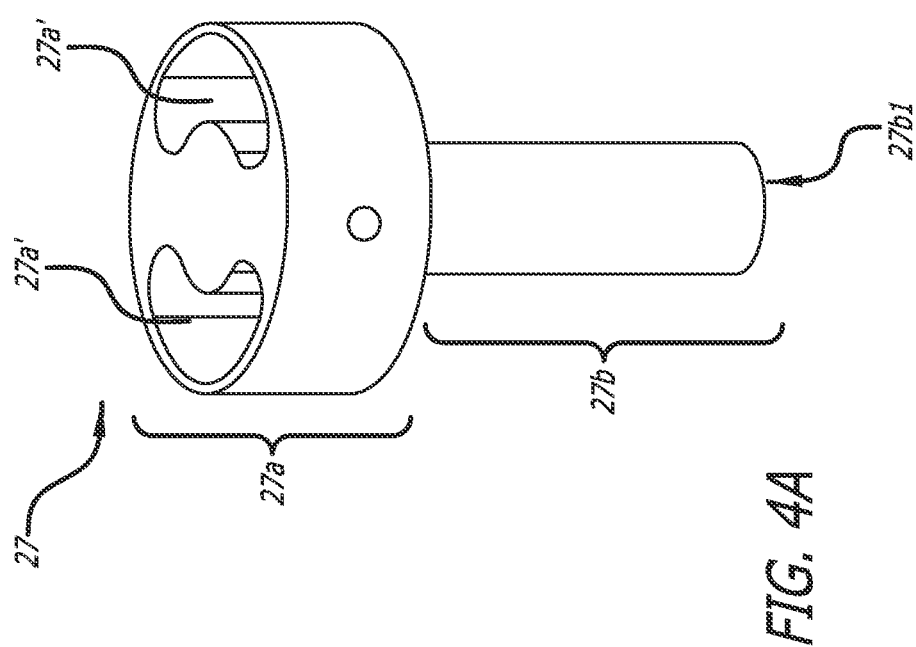
Figure 5:
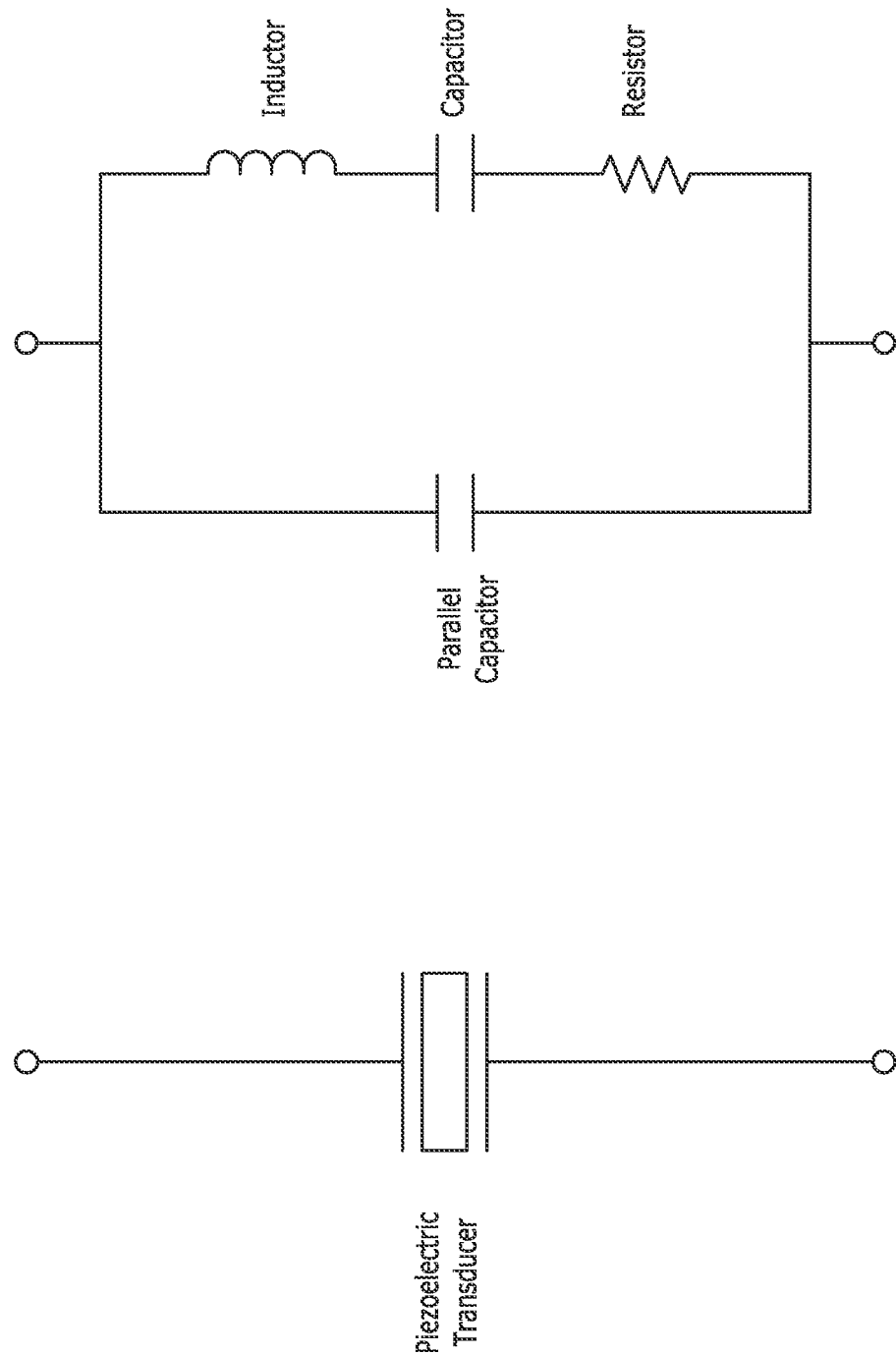
Figure 6:
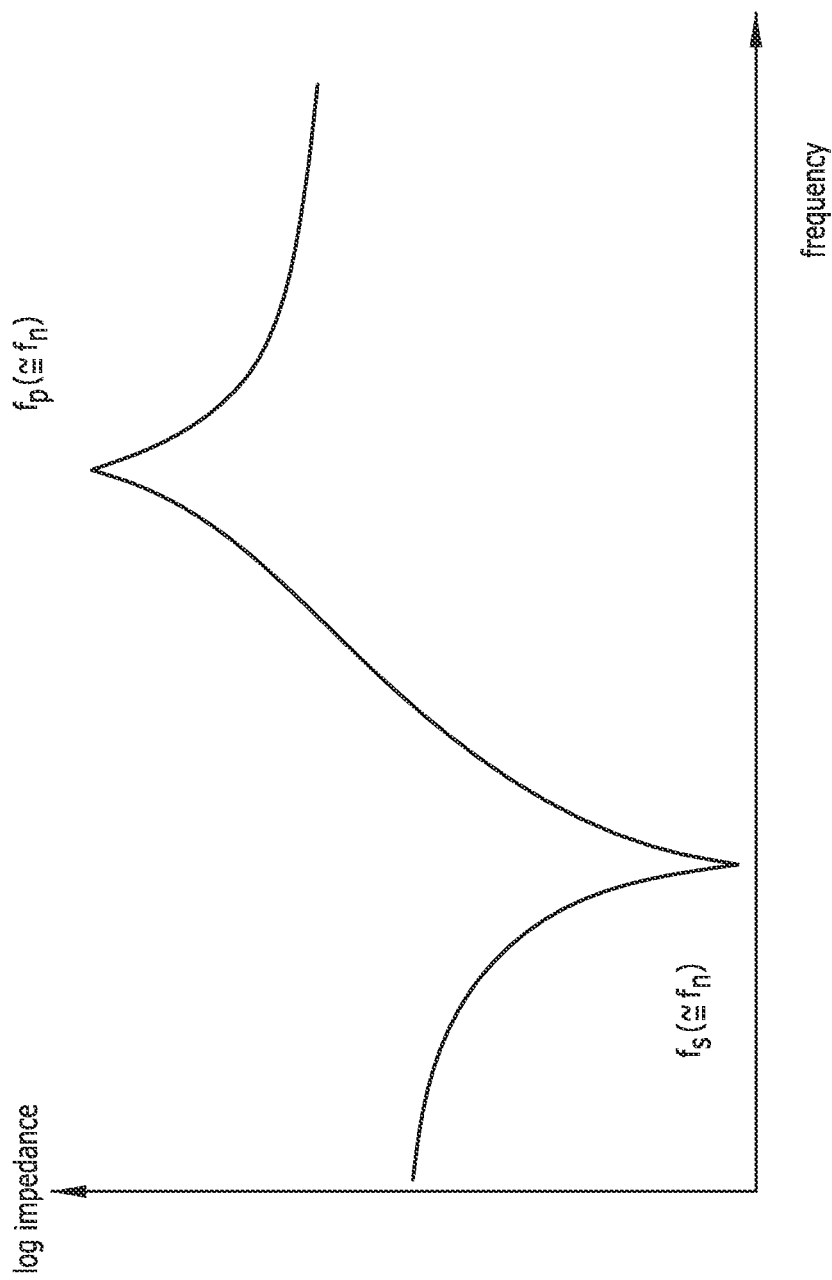
Figure 7:
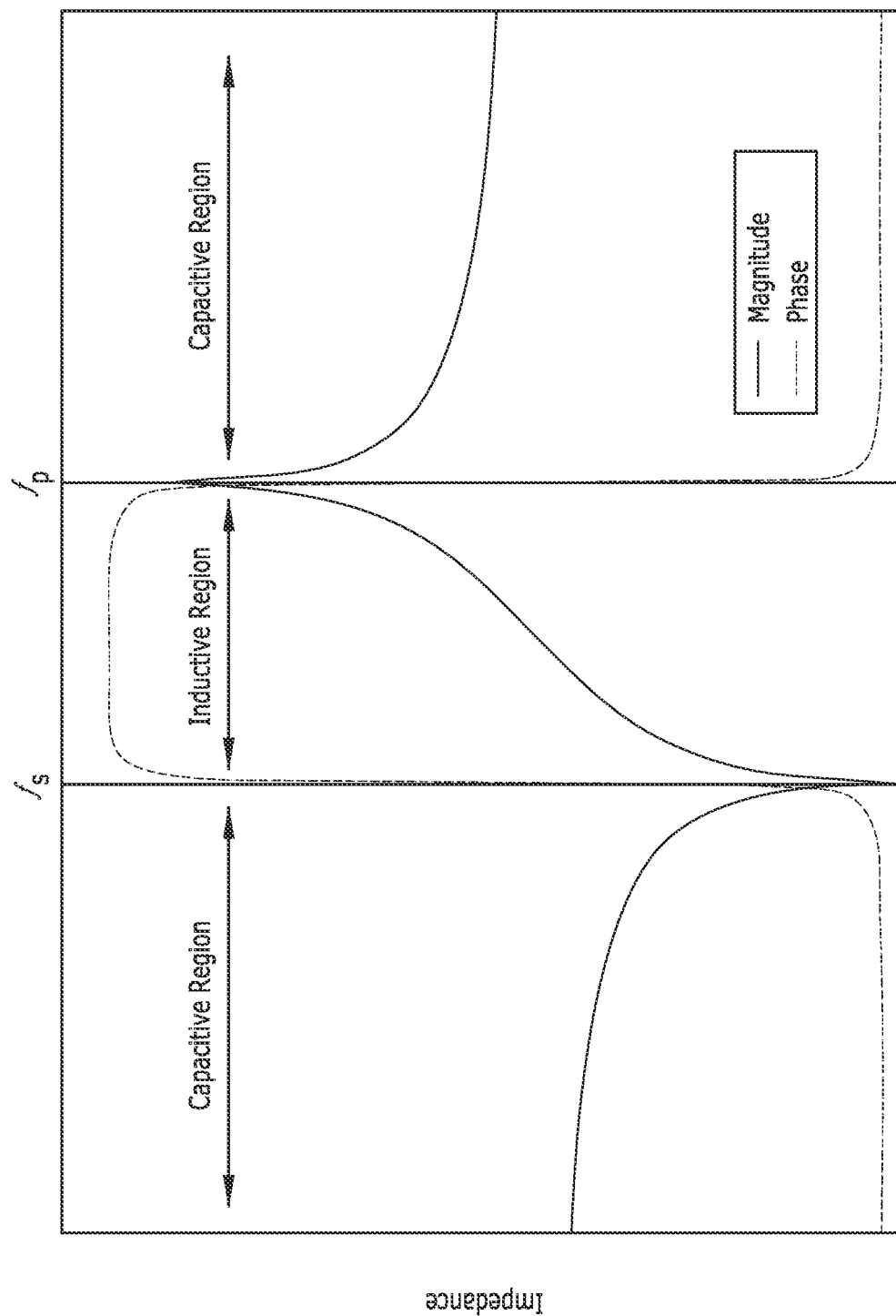
Figure 8:
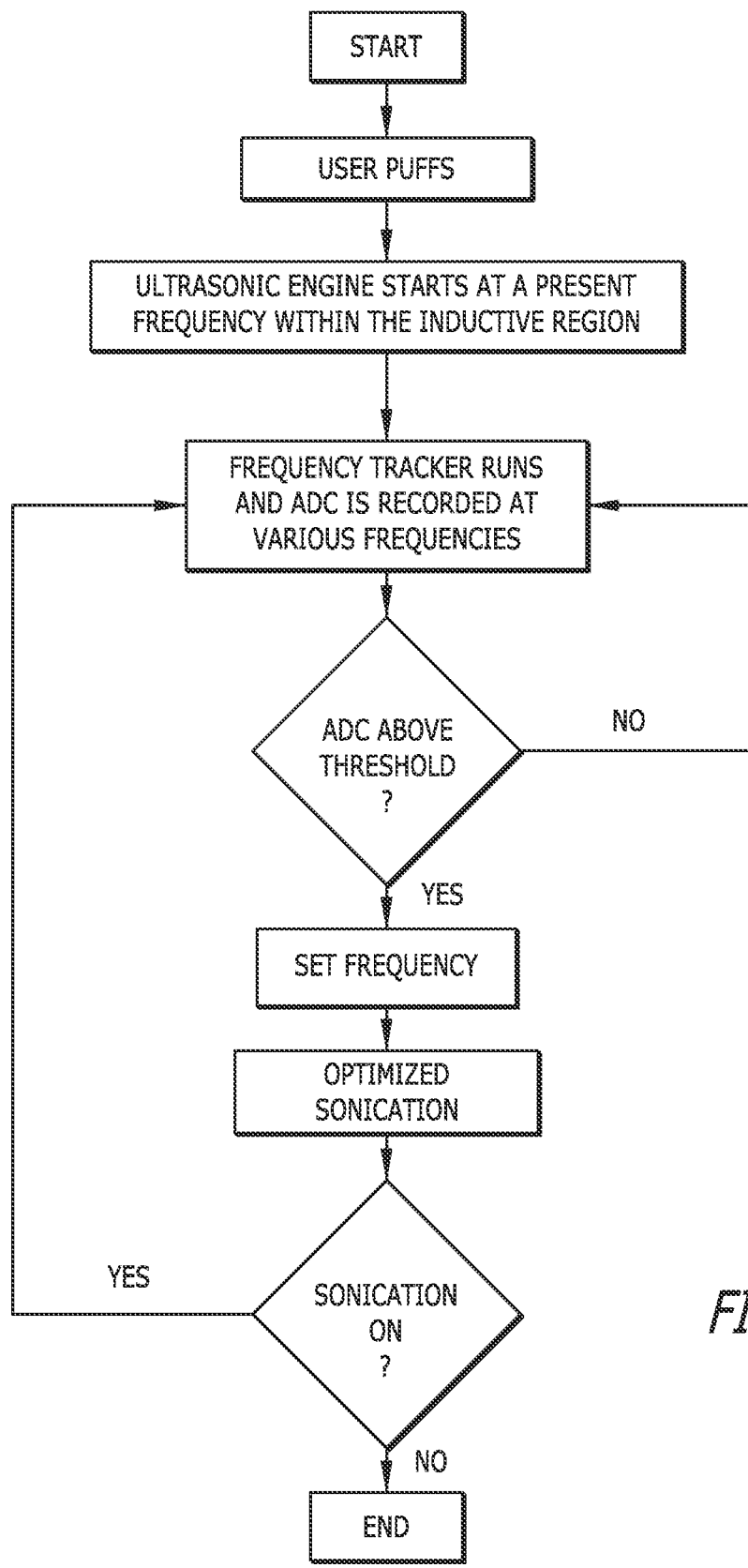
Figure 9:
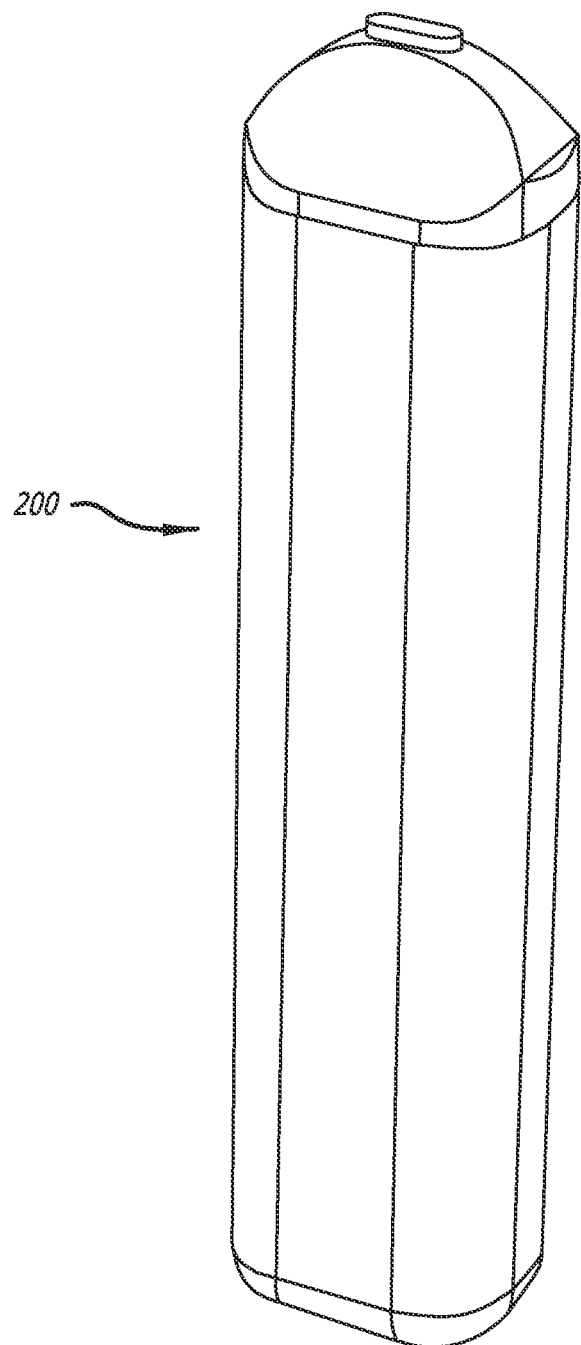
Figure 10:
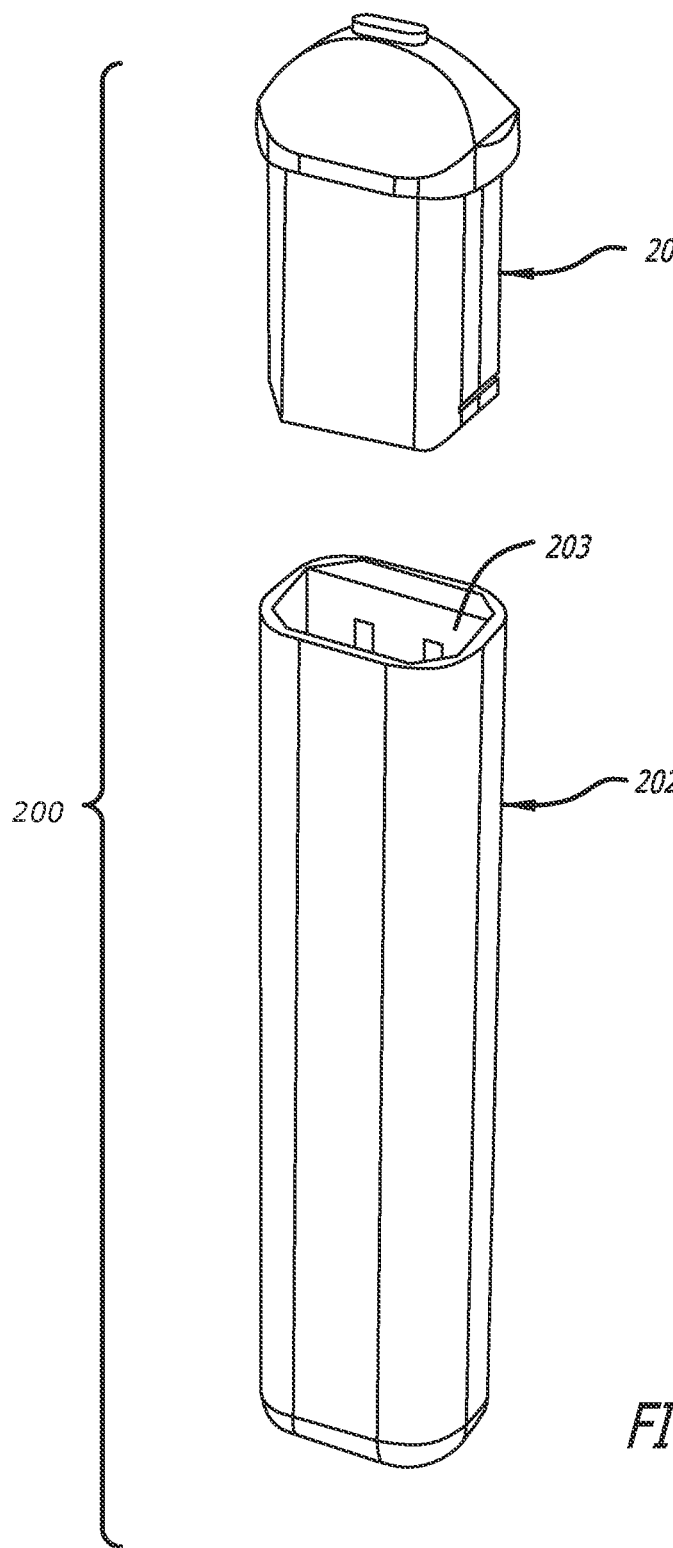
Figure 11:
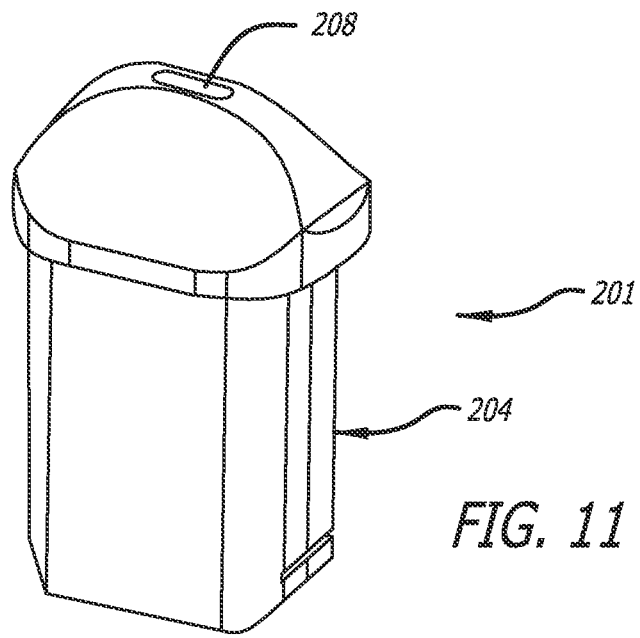
Figure 12:
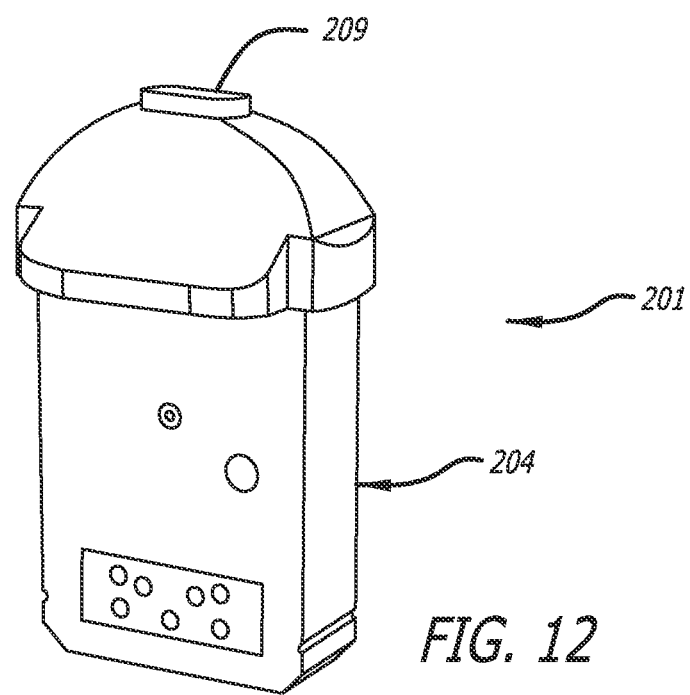
Figure 13:
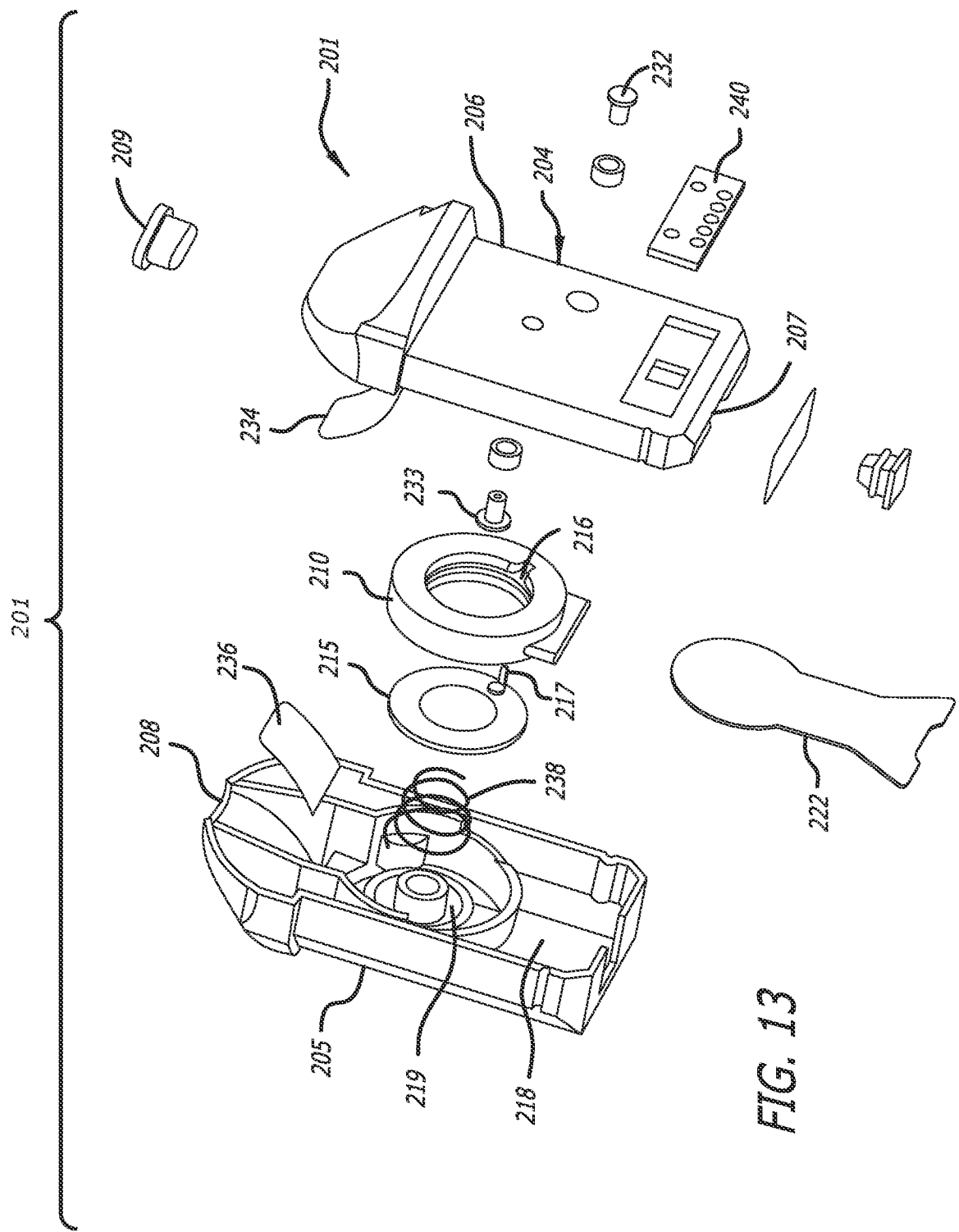

As depicted in FIGS. 4A and 4B. further the inhalation channel 20 has an airflow member 27 for providing air flow from the surroundings to the sonication chamber 22.

The airflow member 27 has an airflow bridge 27a and an airflow duct 27b made in one piece, the airflow bridge 27a having two airway openings 27a' forming a portion of the inhalation channel 20 and the airflow duct 27b extending in the sonication chamber 22 from the airflow bridge 27a for providing the air flow from the surroundings to the sonication chamber.

The airflow bridge 27a cooperates with the frustoconical element 20a at the second diameter 20a2.

The airflow bridge 27a has two opposite peripheral openings 27a" providing air flow to the airflow duct 27b.

The cooperation with the airflow bridge 27a and the frustoconical element 20a is arranged so that the two opposite peripheral openings 27a" cooperate with complementary openings 20a" in the frusoconical element 20a.

The mouthpiece 1 and the frustoconical element 20a are radially spaced and an airflow chamber 28 is arranged between them.

As depicted in FIGS. 1 and 2, the mouthpiece 1 has two opposite peripheral openings 1".

The peripheral openings 27a", 20a", 1" of the airflow bridge 27a, the frustoconical element 20a and the mouthpiece 1 directly supply maximum air flow to the sonication chamber 22.

The frustoconical element 20a includes an internal passage, aligned in the similar direction as the inhalation channel 20, having a first diameter 20a1 less than that of a second diameter 20a2, such that the internal passage reduces in diameter over the frustoconical element 20a.

The frustoconical element 20a is positioned in alignment with the means of ultrasonic vibrations 5 and a capillary element 7, wherein the first diameter 20a1 is linked to an inner duct 11 of the mouthpiece 1 and the second diameter 20a2 is linked to the inner container 20b.

The inner container 20b has an inner wall delimiting the sonication chamber 22 and the liquid chamber 21.

The liquid reservoir structure 2 has an outer container 20c delimiting the outer wall of the liquid chamber 21.

The inner container 20b and the outer container 20c are respectively the inner wall and the outer wall of the liquid chamber 21.

The liquid reservoir structure 2 is arranged between the mouthpiece 1 and the casing 3 and is detachable from the mouthpiece 1 and the casing 3. The liquid reservoir structure 2 and the mouthpiece 1 or the casing 3 may include complimentary arrangements for engaging with one another; further such complimentary arrangements may include one of the following: a bayonet type arrangement; a threaded engaged type arrangement; a magnetic arrangement; or a friction fit arrangement; wherein the liquid reservoir structure 2 includes a portion of the arrangement and the mouthpiece 1 or the casing 3 includes the complimentary portion of the arrangement.

In the reusable example, the components are substantially the same. The differences in the reusable example vis-a-vis the disposable example are the accommodations made to replace the liquid reservoir structure 2.

As shown in FIG. 3, the liquid chamber 21 has a top wall 23 and a bottom wall 25 dosing the inner container 20b and the outer container 20c of the liquid chamber 21.

The capillary element 7 is arranged between a first section 20b1 and a second section 20b2 of the inner container 20b.

The capillary element 7 has a flat shape extending from the sonication chamber to the liquid chamber.

As depicted in FIG. 2 or 3, the capillary element 7 comprises a central portion 7a in U-shape and a peripheral portion 7b in L-shape.

The L-shape portion 7b extends into the liquid chamber 21 on the inner container 20b and along the bottom wall 25.

The U-shape portion 7a is contained into the sonication chamber 21. The U-shape portion 7a on the inner container 20b and along the bottom wall 25.

In the ultrasonic mist inhaler, the U-shape portion 7a has an inner portion 7a1 and an outer portion 7a2, the inner portion 7a1 being in surface contact with an atomisation surface 50 of the means of ultrasonic vibrations 5 and the outer portion 7*a*2 being not in surface contact with the means of ultrasonic vibrations 5.

The bottom wall 25 of the liquid chamber 21 is a bottom plate 25 closing the liquid chamber 21 and the sonication chamber 22. The bottom plate 25 is sealed, thus preventing leakage of liquid from the sonication chamber 22 to the casing The bottom plate 25 has an upper surface 25*a* having a recess 25*b* on which is inserted an elastic member 8. The means of ultrasonic vibrations 5 are supported by the elastic member 8. The elastic member 8 is formed from an annular plate-shaped rubber having an inner hole 8' wherein a groove is designed for maintaining the means of ultrasonic vibrations 5.

The top wall 23 of the liquid chamber 21 is a cap 23 dosing the liquid chamber 23.

The top wall 23 has a top surface 23 representing the maximum level of the liquid that the liquid chamber 21 may contain and the bottom surface 25 representing the minimum level of the liquid in the liquid chamber 21.

The top wall 23 is sealed, thus preventing leakage of liquid from the liquid chamber 21 to the mouthpiece 1.

The top wall 23 and the bottom wall 25 are fixed to the liquid reservoir structure 2 by means of fixation such as screws, glue or friction.

As depicted in FIG. 3, the elastic member is in line contact with the means of ultrasonic vibrations 5 and prevents contact between the means of ultrasonic vibrations 5 and the inhaler wads, suppression of vibrations of the liquid reservoir structure are more effectively prevented. Thus, fine particles of the liquid atomised by the atomising member can be sprayed farther.

As depicted in FIG. 3, the inner container 20*b* has openings 20*b*' between the first section 20*b*1 and the second section 20*b*2 from which the capillary element 7 is extending from the sonication chamber 21. The capillary element 7 absorbs liquid from the liquid chamber 21 through the apertures 20*b*'. The capillary element 7 is a wick. The capillary element 7 transports liquid to the sonication chamber 22 via capillary action. In some examples, the capillary element 7 is made of bamboo fibres. In some examples, the capillary element 7 may be of a thickness between 0.27 mm and 0.32 mm and have a density between 38 $g/m^2$ and 48 $g/m^2$.

As can be seen in FIG. 3, the means of ultrasonic vibrations 5 are disposed directly below the capillary element 7.

The means of ultrasonic vibrations 5 may be a transducer. For example, the means of ultrasonic vibrations 5 may be a piezoelectric transducer, which may be designed in a circular plate-shape. The material of the piezoelectric transducer may be ceramic.

A variety of transducer materials can also be used for the means of ultrasonic vibrations 5.

The end of the airflow duct 27*b*1 faces the means of ultrasonic vibrations 5. The means of ultrasonic vibrations 5 are in electrical communication with electrical contactors 101*a*, 101*b*. It is noted that, the distal end 4*b* of the integrated circuit 4 has an inner electrode and an outer electrode. The inner electrode contacts the first electrical contact 101*a* which is a spring contact probe, and the outer electrode contacts the second electrical contact 101*b* which is a side pin. Via the integrated circuit 4, the first electrical contact 101*a* is in electrical communication with the positive terminal of the electrical storage device 30 by way of the microprocessor, while the second electrical contact 101*b* is in electrical communication with the negative terminal of the electrical storage device 30.

The electrical contacts 101*a*, 101*b* crossed the bottom plate 25. The bottom plate 25 is designed to be received inside the perimeter wall 26 of the liquid reservoir structure 2. The bottom plate 25 rests on complementary ridges, thereby creating the liquid chamber 21 and sonication chamber 22.

The inner container 20*b* comprises a circular inner slot 20*d* on which a mechanical spring is applied.

By pushing the central portion 7*a*1 onto the means of ultrasonic vibrations 5, the mechanical spring 9 ensures a contact surface between them.

The liquid reservoir structure 2 and the bottom plate 25 can be made using a variety of thermoplastic materials. When the user draws on the ultrasonic mist inhaler 100, an air flow is drawn from the peripheral openings 1" and penetrates the airflow chamber 28, passes the peripheral openings 27*a*" of the airflow bridge 27*a* and the frustoconical element 20*a* and flows down into the sonication chamber 22 via the airflow duct 27*b* directly onto the capillary element 7. At the same time, the liquid is drawn from the reservoir chamber 21 by capillarity, through the plurality of apertures 20*b*', and into the capillary element 7. The capillary element 7 brings the liquid into contact with the means of ultrasonic vibrations 5 of the inhaler 100. The user's draw also causes the pressure sensor to activate the integrated circuit 4, which directs current to the means of ultrasonic vibrations 5. Thus, when the user draws on the mouthpiece 1 of the inhaler 100, two actions happen at the same time. Firstly, the sensor activates the integrated circuit 4, which triggers the means of ultrasonic vibrations 5 to begin vibrating. Secondly, the draw reduces the pressure outside the reservoir chamber 21 such that flow of the liquid through the apertures 20*b*' begins, which saturates the capillary element 7. The capillary element 7 transports the liquid to the means of ultrasonic vibrations 5, which causes bubbles to form in a capillary channel by the means of ultrasonic vibrations 5 and mist the liquid. Then, the mist liquid is drawn by the user.

In some examples, the integrated circuit 4 comprises a frequency controller which is configured to control the frequency at which the means of ultrasonic vibrations 5 operates. The frequency controller comprises a processor and a memory, the memory storing executable instructions which, when executed by the processor, cause the processor to perform at least one function of the frequency controller.

As described above, in some examples the ultrasonic mist inhaler 100 drives the means of ultrasonic vibrations 5 with a signal having a frequency of 2.8 MHz to 3.2 MHz in order to vaporise a liquid having a liquid viscosity of 1.05 Pa·s to 1.412 Pa·s in order to produce a bubble volume of about 0.25 to 0.5 microns. However, for liquids with a different viscosity or for other applications it the means of ultrasonic vibrations 5 may be driven at a different frequency. For each different application for a mist generation system, there is an optimum frequency or frequency range for driving the means of ultrasonic vibrations 5 in order to optimize the generation of mist. In examples where the means of ultrasonic vibrations 5 is a piezoelectric transducer, the optimum frequency or frequency range will depend on at least the following four parameters:

1. Transducer Manufacturing Processes

In some examples, the means of ultrasonic vibrations 5 comprises a piezoelectric ceramic. The piezoelectric ceramic is manufactured by mixing compounds to make a ceramic dough and this mixing process may not be consistent throughout production. This inconsistency can give rise to a range of different resonant frequencies of the cured piezoelectric ceramic.

If the resonant frequency of the piezoelectric ceramic does not correspond to the required frequency of operation of the device then no mist is produced during the operation of the device. In the case of a nicotine mist inhaler, even a slight offset in the resonant frequency of the piezoelectric ceramic is enough to impact the production of mist, meaning that the device will not deliver adequate nicotine levels to the user.

2. Load on Transducer

During operation, any changes in the load on the piezoelectric transducer will inhibit the overall displacement of the oscillation of the piezoelectric transducer. To achieve optimal displacement of the oscillation of the piezoelectric transducer, the drive frequency must be adjusted to enable the circuit to provide adequate power for maximum displacement.

The types of loads that can affect the oscillator's efficiency can include the amount of liquid on the transducer (dampness of the wicking material), and the spring force applied to the wicking material to keep permanent contact with the transducer. It may also include the means of electrical connection.

3. Temperature

Ultrasonic oscillations of the piezoelectric transducer are partially damped by its assembly in a device. This may include the transducer being placed in a silicone/rubber ring, and the spring exerting pressure onto the wicking material that is above the transducer. This dampening of the oscillations causes rise in local temperatures on and around the transducer.

An increase in temperature affects the oscillation due to changes in the molecular behaviour of the transducer. An increase in the temperature means more energy to the molecules of the ceramic, which temporarily affects its crystalline structure. Although the effect is reversed as the temperature reduces, a modulation in supplied frequency is required to maintain optimal oscillation. This modulation of frequency cannot be achieved with a conventional fixed frequency device.

An increase in temperature also reduces the viscosity of the solution (e-liquid) which is being vaporized, which may require an alteration to the drive frequency to induce cavitation and maintain continuous mist production. In the case of a conventional fixed frequency device, a reduction in the viscosity of the liquid without any change in the drive frequency will reduce or completely stop mist production, rendering the device inoperable.

4. Distance to Power Source

The oscillation frequency of the electronic circuit can change depending on the wire-lengths between the transducer and the oscillator-driver. The frequency of the electronic circuit is inversely proportional to the distance between the transducer and the remaining circuit.

Although the distance parameter is primarily fixed in a device, it can vary during the manufacturing process of the device, reducing the overall efficiency of the device. Therefore, it is desirable to modify the drive frequency of the device to compensate for the variations and optimise the efficiency of the device.

A piezoelectric transducer can be modelled as an RLC circuit in an electronic circuit, as shown in FIG. 5. The four parameters described above may be modelled as alterations to the overall inductance, capacitance, and/or resistance of the RLC circuit, changing the resonance frequency range supplied to the transducer. As the frequency of the circuit increases to around the resonance point of the transducer, the log Impedance of the overall circuit dips to a minimum and then rises to a maximum before settling to a median range.

FIG. 6 shows a generic graph explaining the change in overall impedance with increase in frequency in an RLC circuit. FIG. 7 shows how a piezoelectric transducer acts as a capacitor in a first capacitive region at frequencies below a first predetermined frequency $f_s$ and in a second capacitive region at frequencies above a second predetermined frequency $f_p$. The piezoelectric transducer acts as an inductor in an inductive region at frequencies between the first and second predetermined frequencies $f_s$, $f_p$. In order to maintain optimal oscillation of the transducer and hence maximum efficiency, the current flowing through the transducer must be maintained at a frequency within the inductive region.

The frequency controller of the device of some examples is configured to maintain the frequency of oscillation of the piezoelectric transducer (the means of ultrasonic vibrations 5) within the inductive region, in order to maximise the efficiency of the device.

The frequency controller is configured to perform a sweep operation in which the frequency controller drives the transducer at frequencies which track progressively across a predetermined sweep frequency range. As the frequency controller performs the sweep, the frequency controller monitors an Analog-to-Digital Conversion (ADC) value of an Analog-to-Digital converter which is coupled to the transducer. In some examples the ADC value is a parameter of the ADC which is proportional to the voltage across the transducer. In other examples, the ADC value is a parameter of the ADC which is proportional to the current flowing through the transducer.

As will be described in more detail below, the frequency controller of some examples determines the active power being used by the ultrasonic transducer by monitoring the current flowing through the transducer.

During the sweep operation, the frequency controller locates the inductive region of the frequency for the transducer. Once the frequency controller has identified the inductive region, the frequency controller records the ADC value and locks the drive frequency of the transducer at a frequency within the inductive region (i.e. between the first and second predetermined frequencies $f_s$, $f_p$) in order to optimise the ultrasonic cavitation by the transducer. When the drive frequency is locked within the inductive region, the electro-mechanical coupling factor of the transducer is maximised, thereby maximising the efficiency of the device.

In some examples, the frequency controller is configured to perform the sweep operation to locate the inductive region each time the oscillation is started or re-started. In the examples, the frequency controller is configured to lock the drive frequency at a new frequency within the inductive region each time the oscillation is started and thereby compensate for any changes in the parameters that affect the efficiency of operation of the device.

In some examples, the frequency controller ensures optimal mist production and maximises efficiency of medication delivery to the user. In some examples, the frequency controller optimises the device and improves the efficiency and maximises nicotine delivery to the user.

In other examples, the frequency controller optimises the device and improves the efficiency of any other device which uses ultrasound. In some examples, the frequency controller is configured for use with ultrasound technology for therapeutic applications in order to extend the enhancement of drug release from an ultrasound-responsive drug delivery system. Having precise, optimal frequency during operation, ensures that the microbubbles, nanobubbles, nanodroplets, liposome, emulsions, micelles or any other delivery systems are highly effective.

In some examples, in order to ensure optimal mist generation and optimal delivery of compounds as described above, the frequency controller is configured to operate in a recursive mode. When the frequency controller operates in the recursive mode, the frequency controller runs the sweep of frequencies periodically during the operation of the device and monitors the ADC value to determine if the ADC value is above a predetermined threshold which is indicative of optimal oscillation of the transducer.

In some examples, the frequency controller runs the sweep operation while the device is in the process of aerosolising liquid in case the frequency controller is able to identify a possible better frequency for the transducer. If the frequency controller identifies a better frequency, the frequency controller locks the drive frequency at the newly identified better frequency in order to maintain optimal operation of the device.

In some examples, the frequency controller runs the sweep of frequencies for a predetermined duration periodically during the operation of the device. In the case of the device of the examples described above, the predetermined duration of the sweep and the time period between sweeps are selected to optimise the functionality of the device. When implemented in an ultrasonic mist inhaler device, this will ensure an optimum delivery to a user throughout the user's inhalation.

FIG. 8 shows a flow diagram of the operation of the frequency controller of some examples.

The following disclosure discloses further examples of mist inhaler devices which comprise many of the same elements as the examples described above. Elements of the examples described above may be interchanged with any of the elements of the examples described in the remaining part of this disclosure.

To ensure adequate aerosol production, in this example the mist inhaler device comprises an ultrasonic/piezoelectric transducer of exactly or substantially 16 mm diameter. This transducer is manufactured to specific capacitance and impedance values to control the frequency and power required for desired aerosol volume production.

A horizontally placed disc-shaped 16 mm diameter ultrasonic transducer would result in a large device that may not be ergonomic as handheld. To mitigate this concern, the ultrasonic transducer of this example is held vertically in the sonication chamber (the planar surface of the ultrasonic transducer is generally parallel with the flow of aerosol mist to the mouthpiece and/or generally parallel to the longitudinal length of the mist inhaler device). Put another way, the ultrasonic transducer is generally perpendicular to a base of the mist inhaler device.

Referring now to FIGS. 9 and 10 of the accompanying drawings, a mist inhaler device 200 of some examples comprises a mist generator device 201 and a driver device 202. The driver device 202 is, in this example, provided with a recess 203 which receives and retains part of the mist generator device 201. The mist generator 201 can therefore be coupled with the driver device 202 to form a compact and portable mist inhaler device 200, as shown in FIG. 9. Referring now to FIGS. 11 to 13 of the accompanying drawings, the mist generator device 201 comprises a mist generator housing 204 which is elongate and optionally formed from two housing portions 205, 206 which are attached to one another. The mist generator housing 204 comprises an air inlet port 207 and a mist outlet port 208.

In this example, the mist generator housing 204 is of injection moulded plastic, specifically polypropylene that is typically used for medical applications. In this example, the mist generator housing 204 is of a heterophasic copolymer. More particularly a BF970MO heterophasic copolymer, which has an optimum combination of very high stiffness and high impact strength. The mist generator housing parts moulded with this material exhibit good anti-static performance.

A heterophasic copolymer such as polypropylene is particularly suitable for the mist generator housing 204 since this material does not cause condensation of the aerosol as it flows from the sonication chamber 219 through the mouthpiece to the user. This plastic material can also be directly recycled easily using industrial shredding and cleaning processes.

In FIGS. 9, 10 and 12, the mist outlet port 208 is closed by a closure element 209. However, it is to be appreciated that when the mist inhaler device 200 is in use, the closure element 209 is removed from the mist outlet port 208, as shown in FIG. 11.

Referring now to FIGS. 14 and 15, the mist generator device 200 comprises a transducer holder 210 which is held within the mist generator housing 204. The transducer holder 210 comprises a body portion 211 which, in this example, is cylindrical or generally cylindrical in shape with circular upper and lower openings 212, 213. The transducer holder 210 is provided with an internal recess 214 for receiving an edge of an ultrasonic transducer 215, as shown in FIG. 15.

The transducer holder 210 incorporates a cutaway section 216 through which an electrode 217 extends from the ultrasonic transducer 215 so that the electrode 217 may be connected electrically to an AC driver of the drive device, as described in more detail below.

Referring again to FIG. 13, the mist generator device 201 comprises a liquid chamber 218 which is provided within the mist generator housing 204. The liquid chamber 218 is for containing a liquid to be atomised. In some examples, a liquid is contained in the liquid chamber 218. In other examples, the liquid chamber 218 is empty initially and the liquid chamber is filled with a liquid subsequently.

A liquid (also referred to herein as an e-liquid) composition suitable for use in an ultrasonic device that is powered at a frequency of 3.0 MHz (±0.2 MHz) by a 3.7V lithium polymer (LiPo) battery consisting of a nicotine salt consisting of nicotine levulinate wherein:

The relative amount of vegetable glycerin in the composition is: from 55 to 80% (w/w), or from 60 to 80% (w/w), or from 65 to 75% (w/w), or 70% (w/w); and/or, The relative amount of propylene glycol in the composition is: from 5 to 30% (w/w), or from 10 to 30% (w/w), or from 15 to 25% (w/w), or 20% (w/w); and/or, The relative amount of water in the composition is: from 5 to 15% (w/w), or from 7 to 12% (w/w), or 10% (w/w); and/or, The amount of nicotine and/or nicotine salt in the composition is: from 0.1 to 80 mg/ml, or from 0.1 to 50 mg/ml, or from 1 to 25 mg/ml, or from 10 to 20 mg/m or 17 mg/nil.

In some examples, the mist generator device 201 contains an e-liquid having a liquid viscosity between 1.05 Pa·s and 1.412 Pa·s.

In some examples, the liquid chamber 218 contains a liquid comprising a nicotine levulinate salt at a 1:1 molar ratio.

In some examples, the liquid chamber 218 contains a liquid having a liquid viscosity between 1.05 Pa·s and 1.412 Pa·s and a liquid density between 1.1 g/ml and 1.3 g/ml.

By using an e-liquid with the correct parameters of viscosity, density and having a desired target bubble volume of liquid spray into the air, it has been found that the frequency range of 2.8 MHz to 3.2 MHz for liquid viscosity range of 1.05 Pa·s and 1.412 Pa·s and density of approximately 1.1-1.3 (get density ranges from Hertz) produce a droplet volume where 90% of droplets are below 1 micron and 50% of those are less than 0.5 microns.

The mist generator device 201 comprises a sonication chamber 219 which is provided within the mist generator housing 204.

Figure 14:
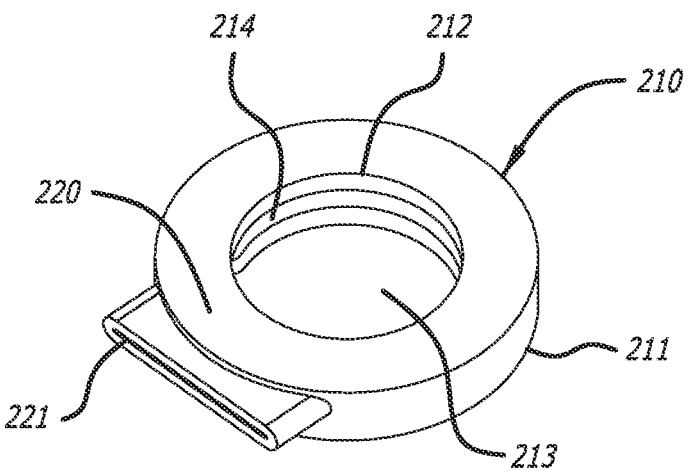
Figure 15:
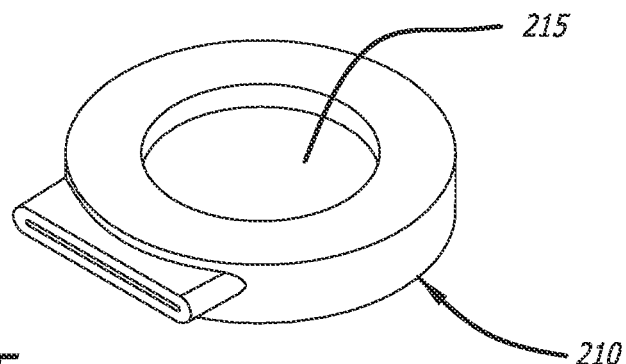

Returning to FIGS. 14 and 15, the transducer holder 210 comprises a divider portion 220 which provides a barrier between the liquid chamber 218 and the sonication chamber 219. The barrier provided by the divider portion 220 minimises the risk of the sonication chamber 219 being is flooded with liquid from the liquid chamber 218 or for a capillary element over the ultrasonic transducer 215 becoming oversaturated, either of which would overload and reduce the efficiency of the ultrasonic transducer 215. Moreover, flooding the sonication chamber 219 or over saturating the capillary element could also cause an unpleasant experience with the liquid being sucked in by the user during inhalation. To mitigate this risk, the divider portion 220 of the transducer holder 210 sits as a wall between the sonication chamber 219 and the liquid chamber 218.

The divider portion 220 comprises a capillary aperture 221 which is the only means by which liquid can flow from the liquid chamber 218 to the sonication chamber 219, via a capillary element. In this example, the capillary aperture 221 is an elongate slot having a width of 0.2 mm to 0.4 mm. The dimensions of the capillary aperture 221 are such that the edges of the capillary aperture 221 provide a biasing force which acts on a capillary element extending through the capillary aperture 221 for added control of liquid flow to the sonication chamber 219.

In this example, the transducer holder 210 is of liquid silicone rubber (LSR). In this example, the liquid silicone rubber has a Shore A 60 hardness. This LSR material ensures that the ultrasonic transducer 215 vibrates without the transducer holder 210 dampening the vibrations. In this example, the vibratory displacement of the ultrasonic transducer 215 is 2-5 nanometres and any dampening effect may reduce the efficiency of the ultrasonic transducer 215. Hence, this LSR material and hardness is selected for optimal performance with minimal compromise.

Figure 16:
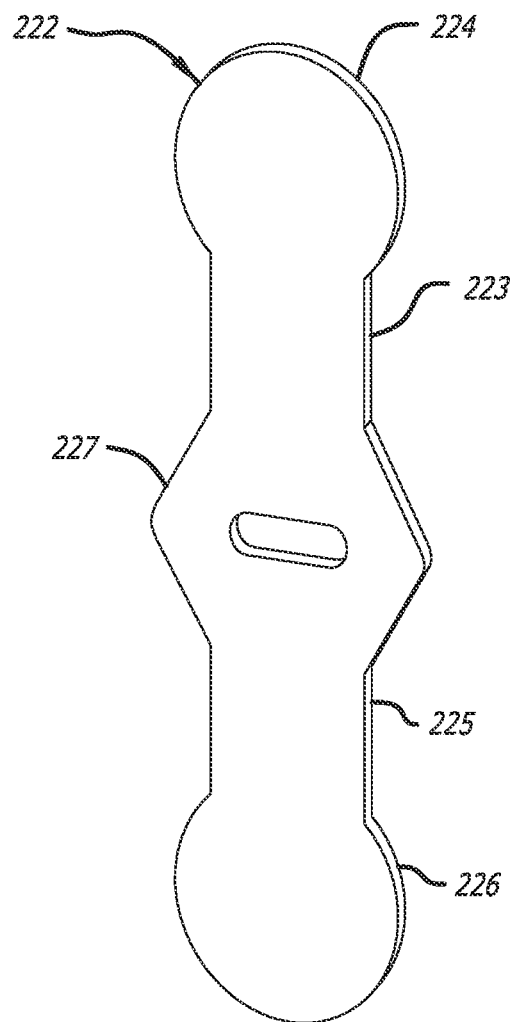
Figure 17:
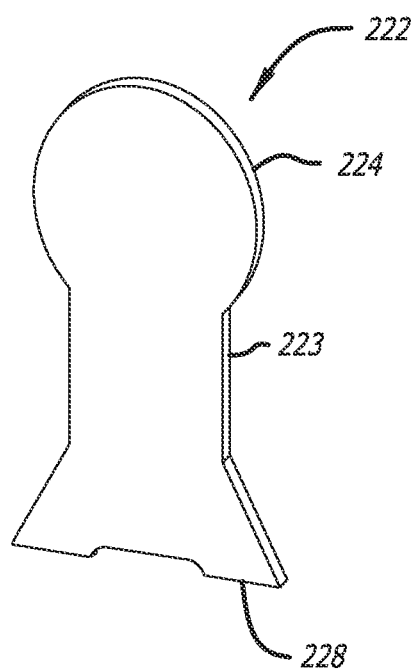

Referring now to FIGS. 16 and 17, the mist generator device 201 comprises a capillary or capillary element 222 for transferring a liquid (containing a drug or other substance) from the liquid chamber 218 to the sonication chamber 219. The capillary element 222 is planar or generally planar with a first portion 223 and a second portion 224. In this example, the first portion 223 has a rectangular or generally rectangular shape and the second portion 224 has a partly circular shape.

In this example, the capillary element 222 comprises a third portion 225 and a fourth portion 226 which are respectively identical in shape to the first and second portions 223, 224. The capillary element 222 of this example is folded about a fold fine 227 such that the first and second portions 223, 224 and the third and fourth portions 225, 226 are superimposed on one another, as shown in FIG. 17.

In this example, the capillary element has a thickness of approximately 0.28 mm. When the capillary element 222 is folded to have two layers, as shown in FIG. 17, the overall thickness of the capillary element is approximately 0.56 mm. This double layer also ensures that there is always sufficient liquid on the ultrasonic transducer 215 for optimal aerosol production.

In this example, when the capillary element 222 is folded, the lower end of the first and third parts 223, 225 defines an enlarged lower end 228 which increases the surface area of the capillary element 222 in the portion of the capillary element 222 which sits in liquid within the liquid chamber 218 to maximise the rate at which the capillary element 222 absorbs liquid.

In this example, the capillary element 222 is 100% bamboo fibre. In other examples, the capillary element is of at least 75% bamboo fibre. The benefits of using bamboo fibre as the capillary element are as described above.

Figure 18:
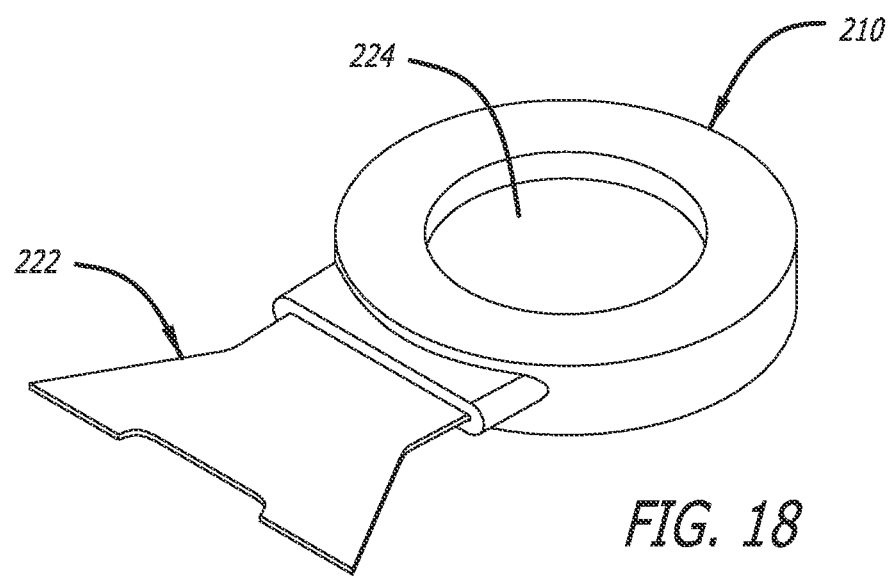
Figure 19:
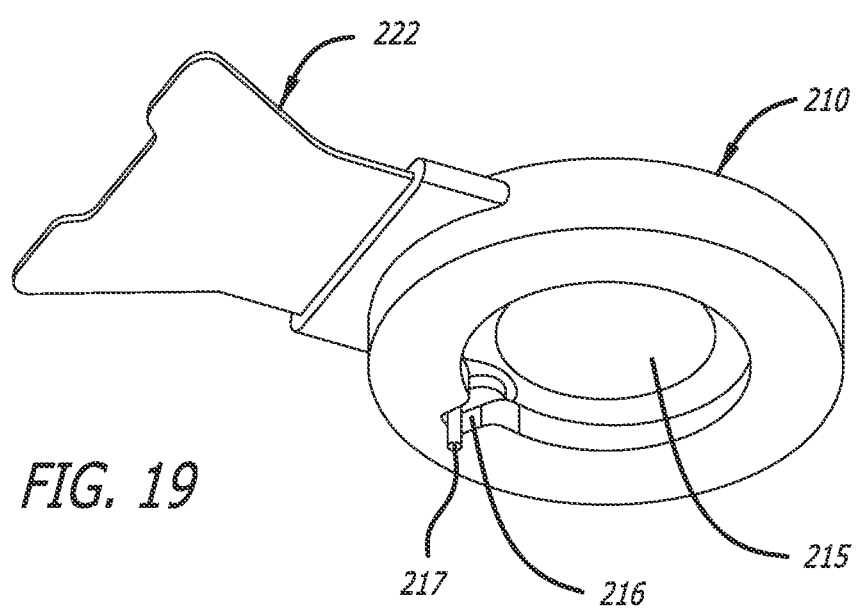

Referring now to FIGS. 18 and 19, the capillary element 222 is retained by the transducer holder 210 such that the transducer holder 210 retains the second portion 224 of the capillary element 222 superimposed on part of an atomisation surface of the ultrasonic transducer 215. In this example; the circular second portion 224 sits within the internal recess 214 of the transducer holder 210.

The first portion 223 of the capillary element 222 extends through the capillary aperture 221 in the transducer holder 210.

Figure 20:
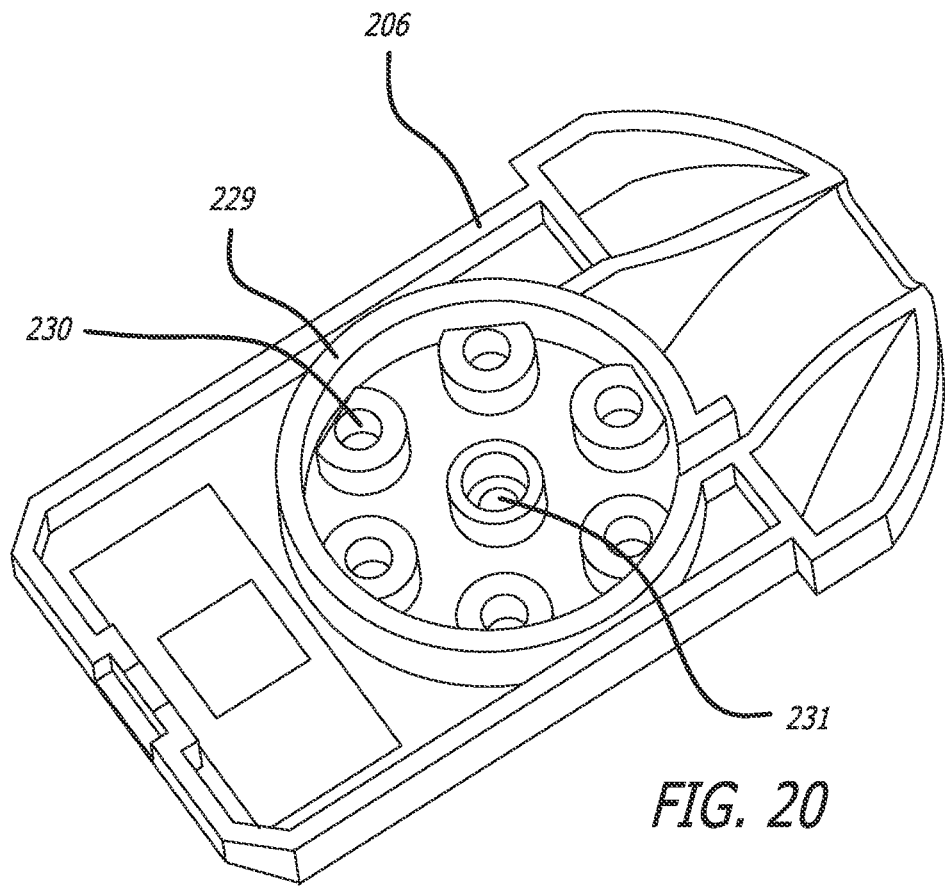
Figure 21:
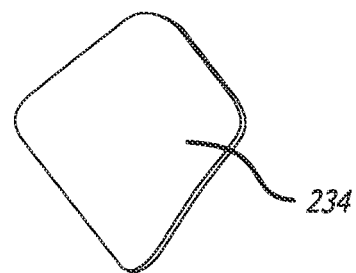
Figure 22:
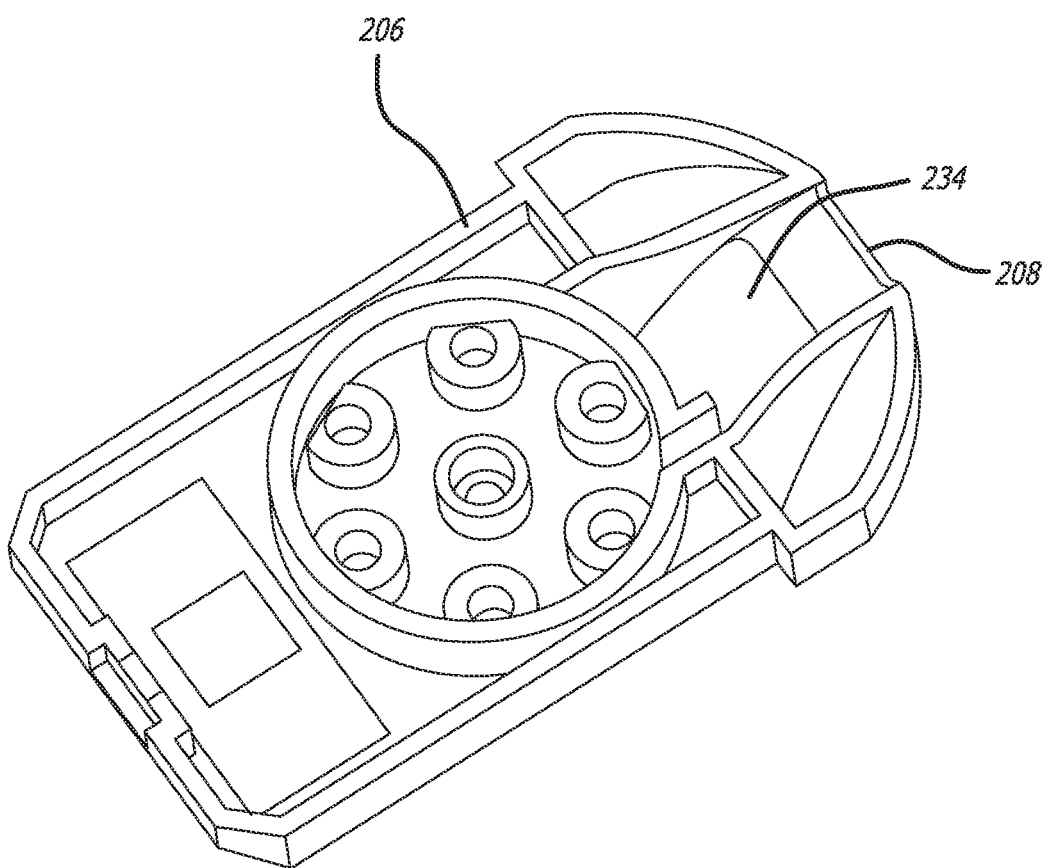

Referring now to FIGS. 20 to 22, the second portion 206 of the mist generator housing 204 comprises a generally circular wall 229 which receives the transducer holder 210 and forms part of the wall of the sonication chamber 219.

Contact apertures 230 and 231 are provided in a side wall of the second portion 206 for receiving electrical contacts 232 and 233 which form electrical connections with the electrodes of the ultrasonic transducer 215.

In this example, an absorbent tip or absorbent element 234 is provided adjacent the mist outlet port 208 to absorb liquid at the mist outlet port 208. In this example, the absorbent element 234 is of bamboo fibre.

Figure 23:
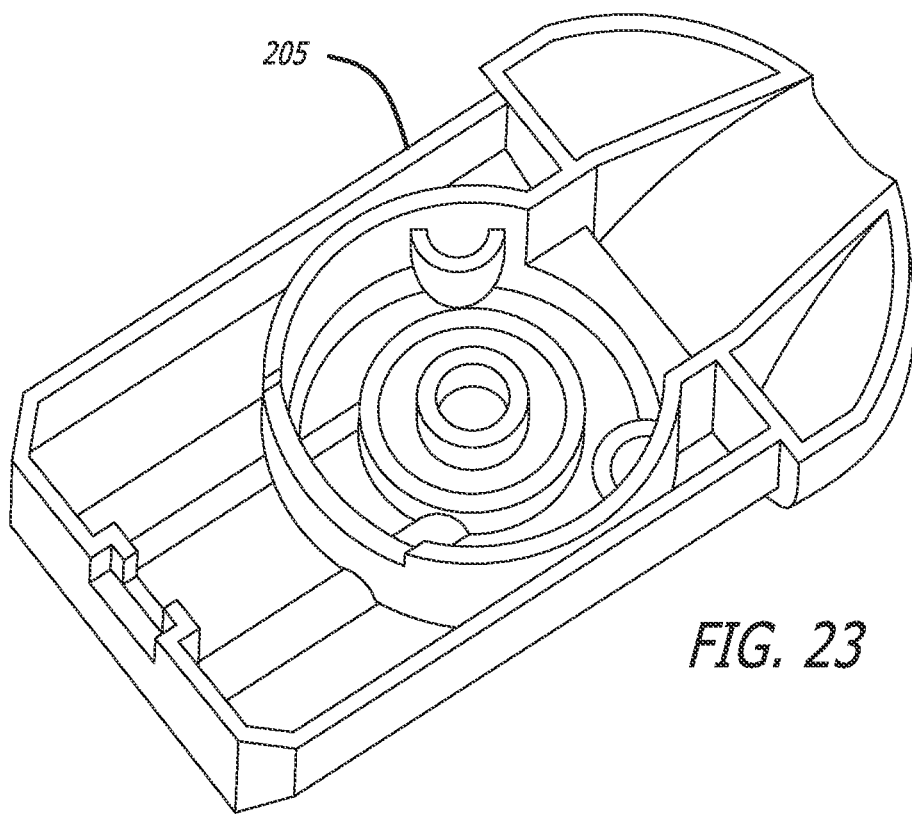
Figure 24:
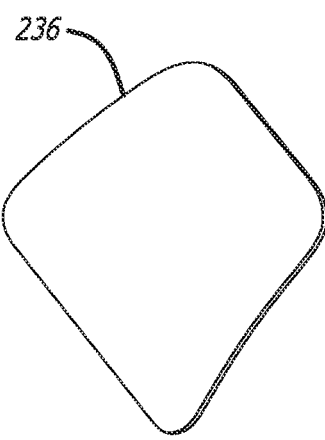
Figure 25:
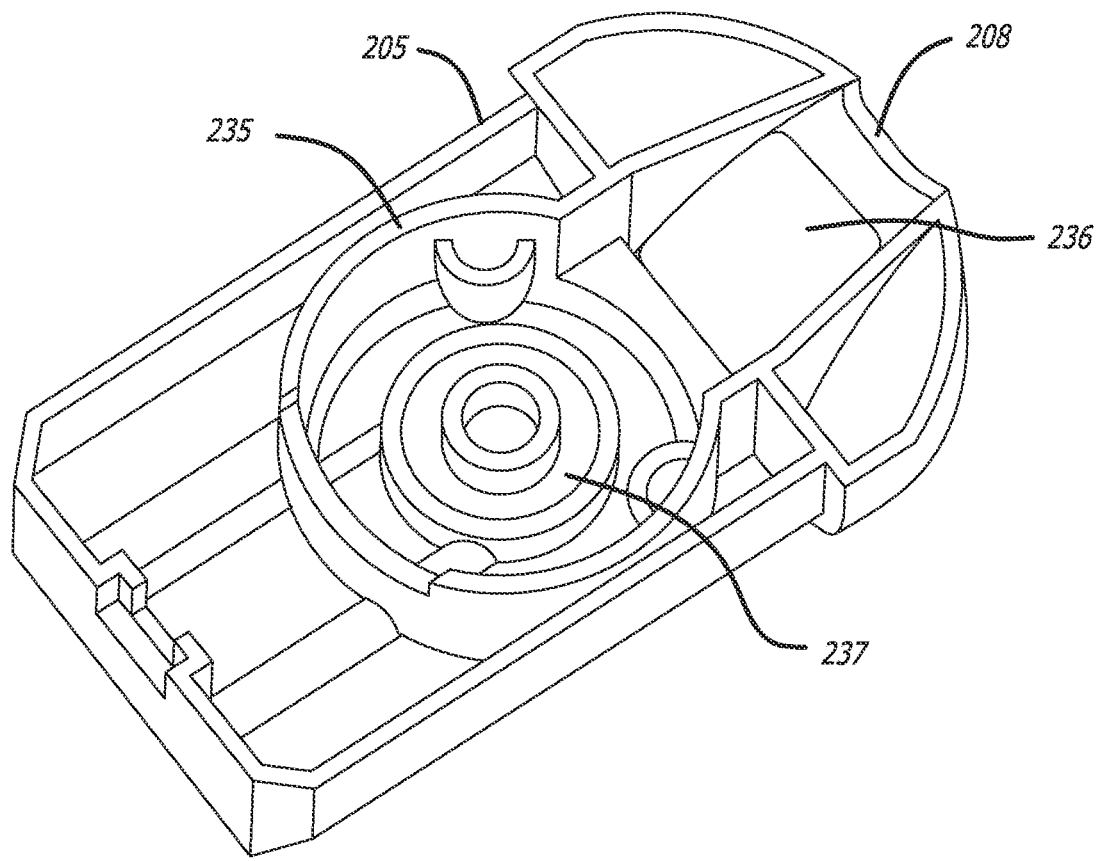

Referring now to FIGS. 23 to 25, the first portion 205 of the mist generator housing 204 is of a similar shape to the second portion 206 and comprises a further generally circular wall portion 235 which forms a further portion of the wall of the sonication chamber 219 and retains the transducer holder 210.

In this example, a further absorbent element 236 is provided adjacent the mist outlet port 208 to absorb liquid at the mist outlet port 208.

Figure 26:
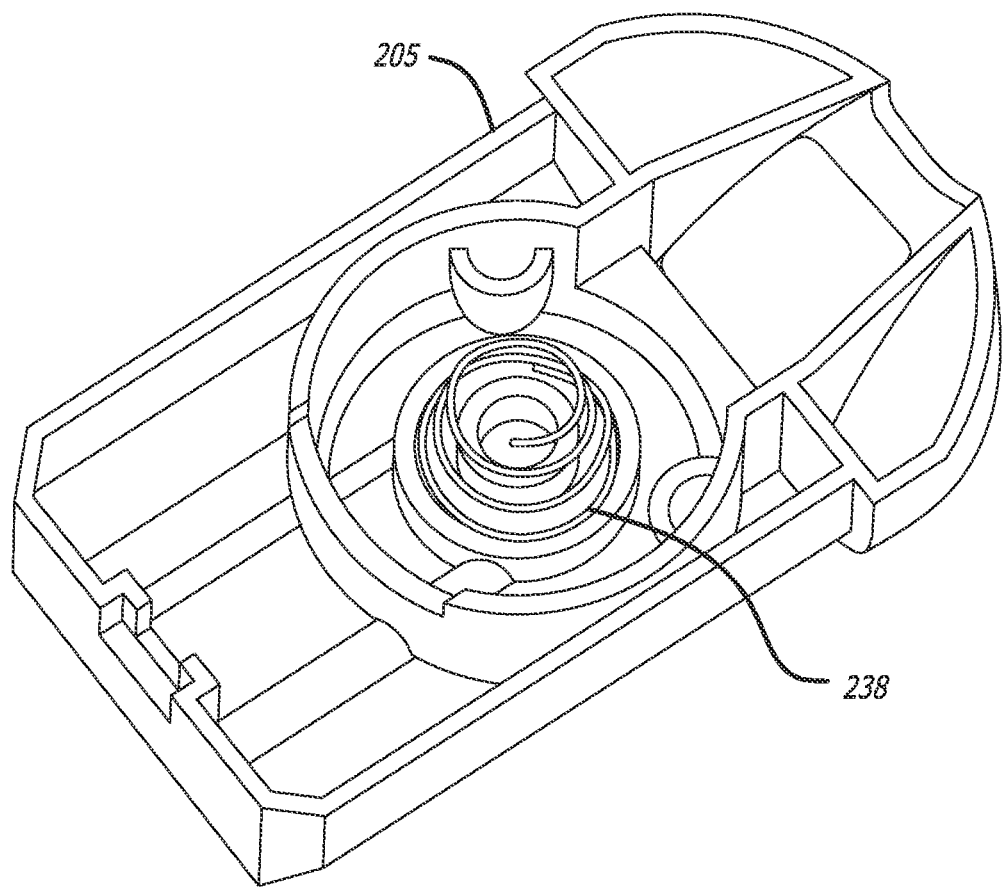
FIG. 26 is a diagrammatic perspective view of a part of a housing of this disclosure.

In this example, the first portion 205 of the mist generator housing 204 comprises a spring support arrangement 237 which supports the lower end of a retainer spring 238, as shown in FIG. 26.

An upper end of the retainer spring 238 contacts the second portion 224 of the capillary element 222 such that the retainer spring 238 provides a biasing force which biases the capillary element 222 against the atomisation surface of the ultrasonic transducer 215.

Figure 27:
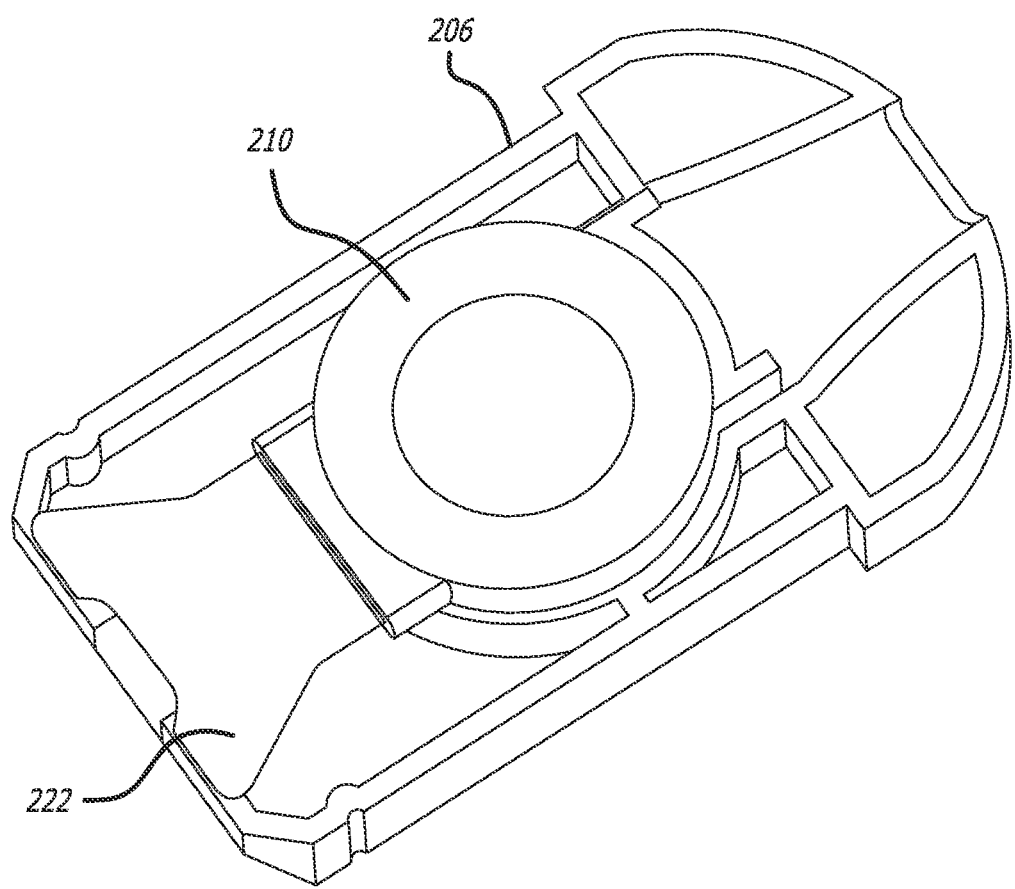
FIG. 27 is a diagrammatic perspective view of a part of a housing of this disclosure.
Figure 28:
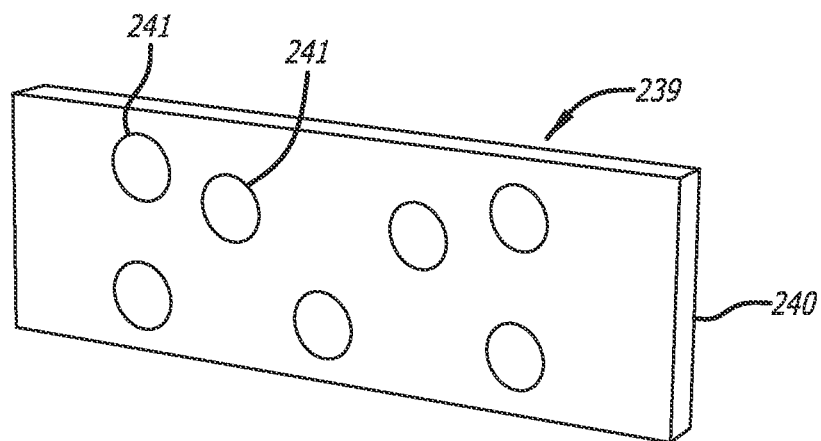
FIG. 28 is a diagrammatic perspective view of a circuit board of this disclosure.
Figure 29:
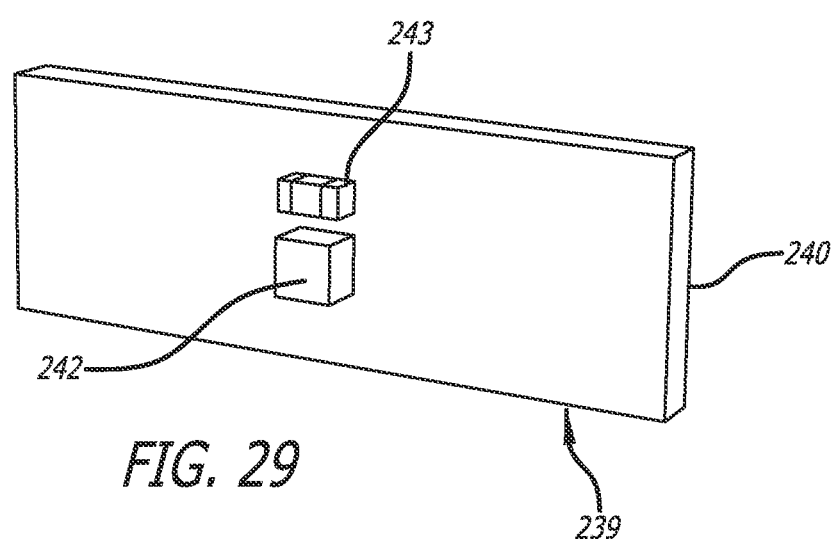
FIG. 29 is a diagrammatic perspective view of a circuit board of this disclosure.
Figure 30:
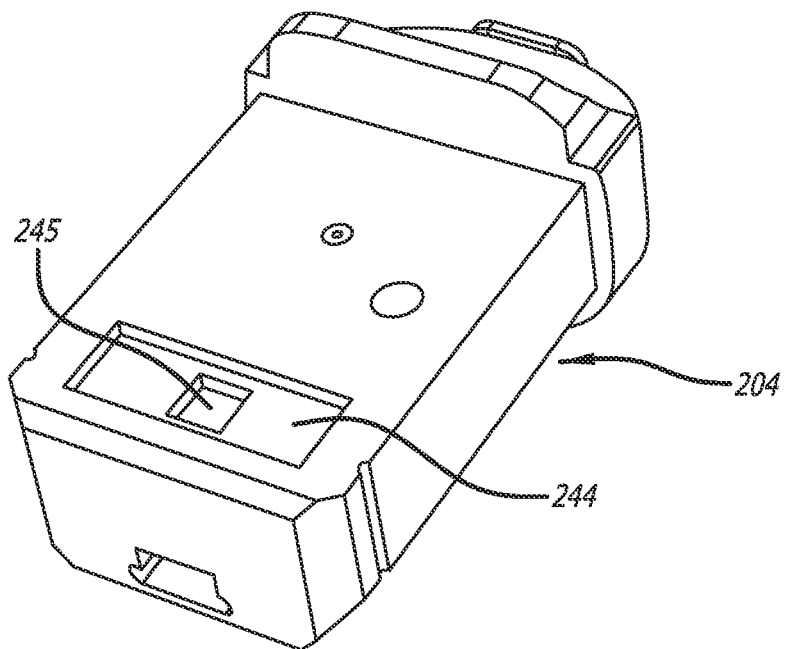
FIG. 30 is a diagrammatic exploded perspective view of a mist generator device of this disclosure.
Figure 31:
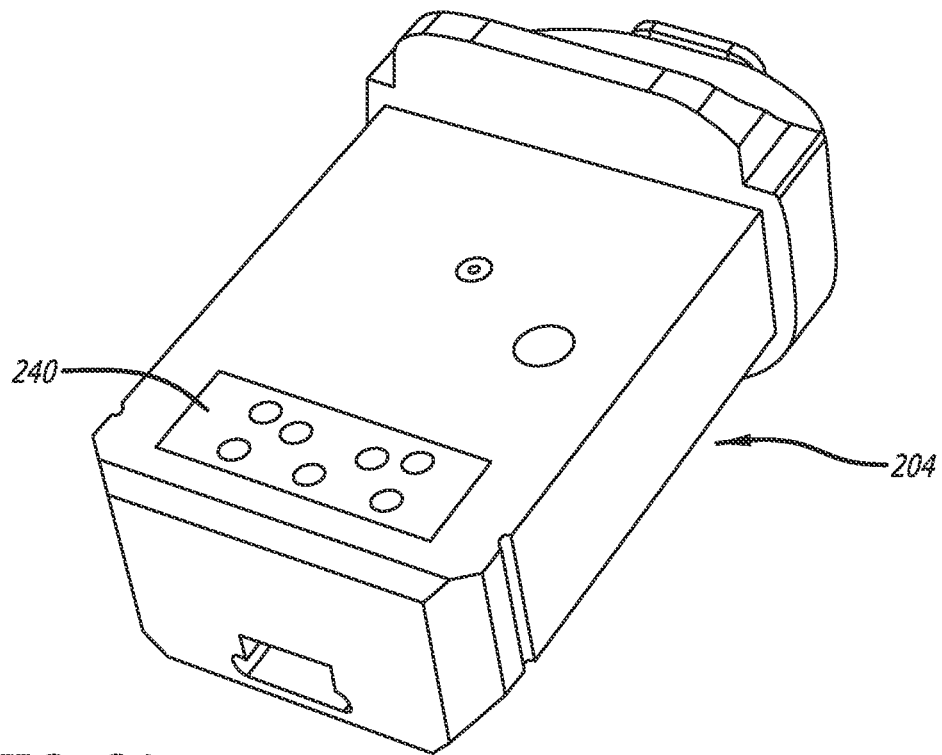
FIG. 31 is a diagrammatic exploded perspective view of a mist generator device of this disclosure.

Referring to FIG. 27, the transducer holder 210 is shown in position and being retained by the second portion 206 of the mist generator housing 204, prior to the two portions 205, 206 of the mist generator housing 204 being attached to one another.

Referring to FIGS. 28 to 31, in this example, the mist generator device 201 comprises an identification arrangement 239. The identification arrangement 239 comprises a printed circuit board 240 having electrical contacts 241 provided on one side and an integrated circuit 242 and another optional component 243 provided on the other side.

The integrated circuit 242 has a memory which stores a unique identifier for the mist generator device 201. The electrical contacts 241 provide an electronic interface for communication with the integrated circuit 242.

The printed circuit board 240 is, in this example, mounted within a recess 244 on one side of the mist generator housing 204. The integrated circuit 242 and optional other electronic components 243 sit within a further recess 245 so that the printed circuit board 240 is generally flush with the side of the mist generator housing 204.

In this example, the integrated circuit 242 is a one-time-programmable (OTP) device which provides an anti-counterfeiting feature that allows only genuine mist generator devices from the manufacturer to be used with the device. This anti-counterfeiting feature is implemented in the mist generator device 201 as a specific custom integrated circuit (IC) that is bonded (with the printed circuit board 240) to the mist generator device 201. The OTP as IC contains a truly unique information that allows a complete traceability of the mist generator device 201 (and its content) over its lifetime as well as a precise monitoring of the consumption by the user. The OTP IC allows the mist generator device 201 to function to generate mist only when authorised.

The OTP, as a feature, dictates the authorised status of a specific mist generator device 201. Indeed, in order to prevent emissions of carbonyls and keep the aerosol at safe standards, experiments have shown that the mist generator device 201 is considered empty of liquid in the liquid chamber 218 after approximately 1,000 seconds of aerosolisation. In that way a mist generator device 201 that is not genuine or empty will not be able to be activated after this predetermined duration of use.

The OTP, as a feature, may be part of a complete chain with the conjunction of the digital sale point, the mobile companion application and the mist generator device 201. Only a genuine mist generator device 201 manufactured by a trusted party and sold on the digital sale point can be used in the device. A mobile companion digital app, being a link between the user account on a manufacturers digital platform and the mist generator device 201, ensures safe usage of a known safe content for a safe amount of puff duration.

The OTP, as a feature, also enables high access control and monitoring required as per medical drug administration in the case of business to business (B2B) use with trusted health establishments. The OTP IC is read by the driver device 202 which can recognise the mist generator device 201 inserted and the prescription associated with it. The driver device 202 cannot be used with this mist generator device 201 more than nor outside of the time frame specified by the prescription. In addition a reminder on the mobile companion app can be provided to minimise a user missing a dose.

In some examples, the OTP IC is disposable in the same way as the mist generator device 201. Whenever the mist generator device 201 is considered empty, it will not be activated if inserted into a driver device 202. Similarly, a counterfeit generator device 201 would not be functional in the driver device 202.

Figure 32:
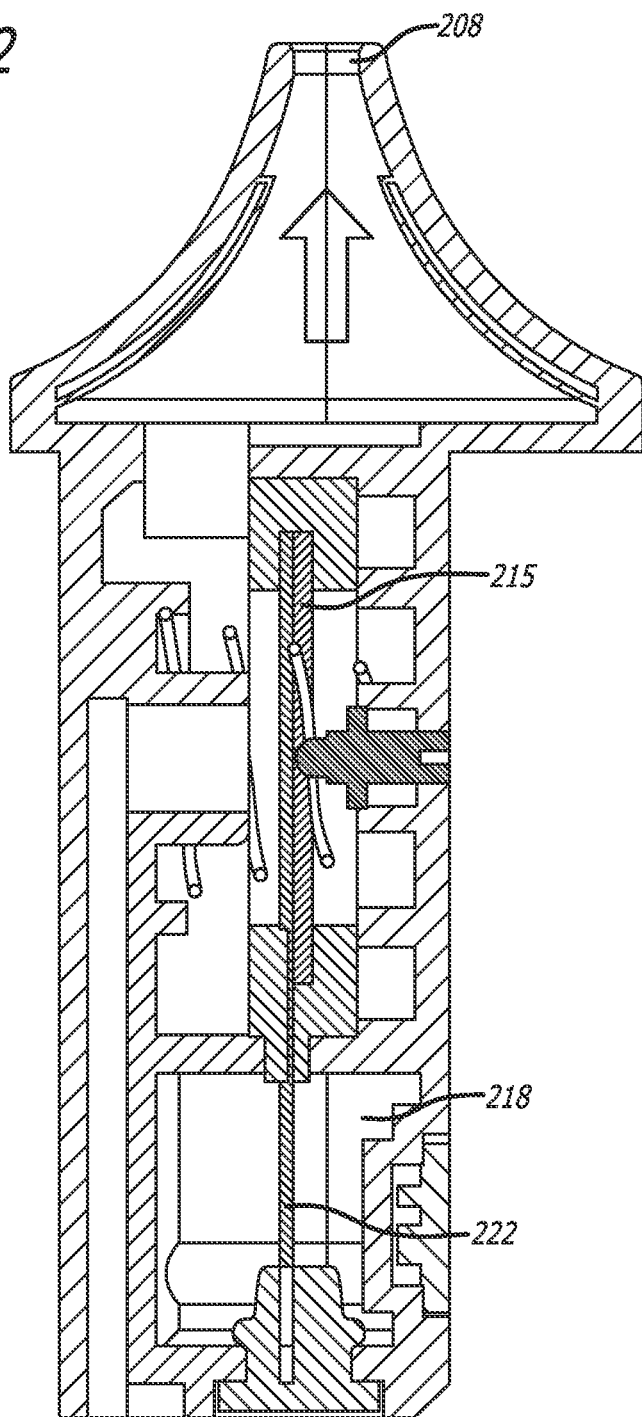
FIG. 32 is a cross sectional view of a mist generator device of this disclosure.
Figure 33:
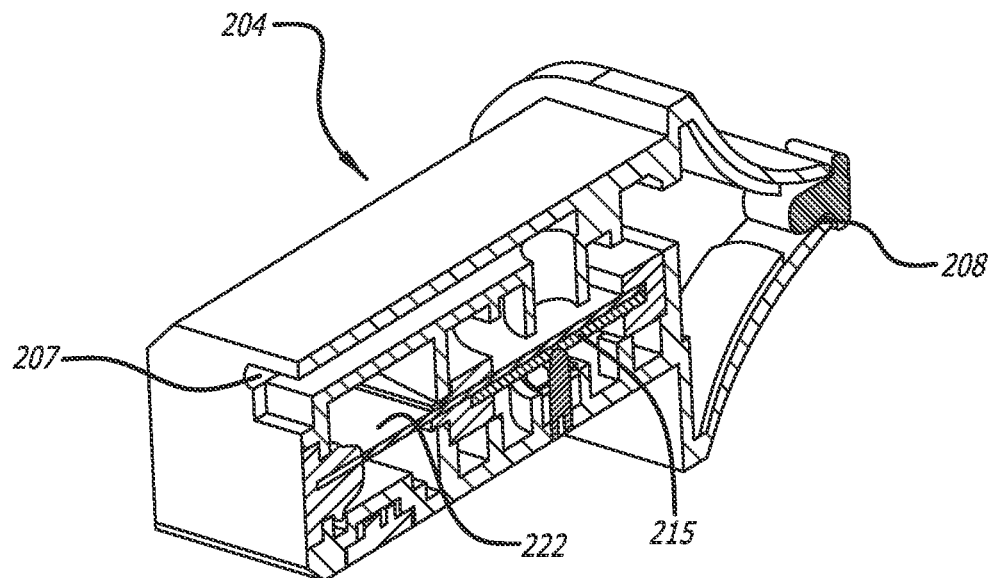
FIG. 33 is a cross sectional view of a mist generator device of this disclosure.
Figure 34:
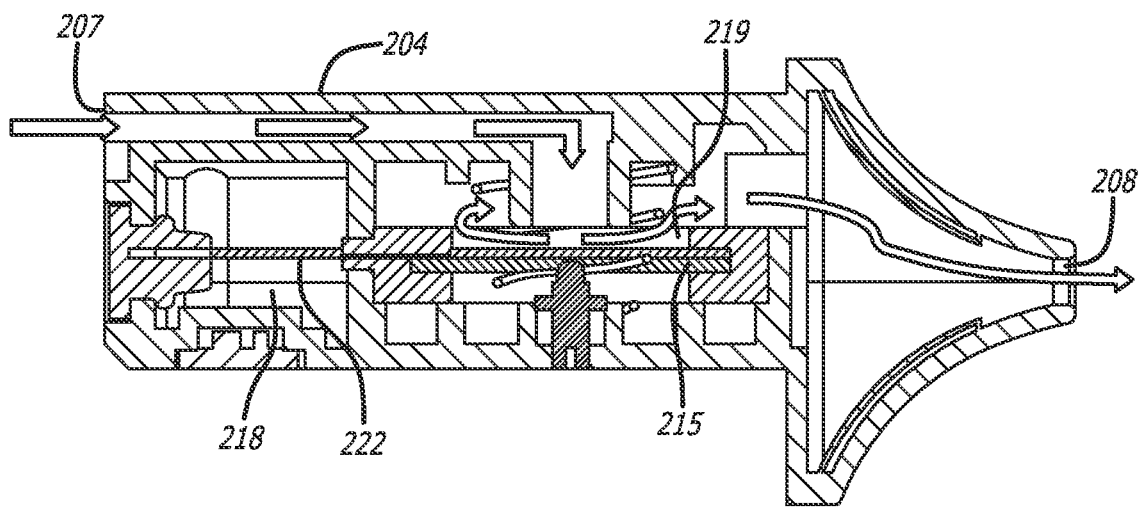
FIG. 34 is a cross sectional view of a mist generator device of this disclosure.

FIGS. 32 to 34 illustrate how air flows through the mist generator device 201 during operation.

The sonication of the liquid drug (Nicotine, medical solutions, medical suspensions, protein solutions, supplements, etc.) transforms it into mist (aerosolisation). However, this mist would settle over the ultrasonic transducer 215 unless enough ambient air is available to replace the rising aerosol. In the sonication chamber 219, there is a requirement for a continuous supply of air as mist (aerosol) is generated and pulled out through the mouthpiece to the user. To cater to this requirement, an airflow channel is provided. In this example the airflow channel has an average cross-sectional area of 11.5 mm$^2$, which is calculated and designed into the sonication chamber 219 based on the negative air pressure from an average user. This also controls the mist-to-air ratio of the inhaled aerosol, controlling the amount of drug delivered to the user.

Based on design requirements, the air flow channel is routed such that it initiates from the bottom of the sonication chamber 219. The opening at the bottom of the aerosol chamber aligns with and is tightly adjacent to the opening to an airflow bridge in the device. The air flow channel runs vertically upwards along the reservoir and continues until the centre of the sonication chamber (concentric with the ultrasonic transducer 215). Here, it turns 90° inwards. The flow path then continues on until approximately 1.5 mm from the ultrasonic transducer 215. This routing ensures maximised ambient air supplied directly in the direction of the atomisation surface of the ultrasonic transducer 215. The air flows through the channel, towards the transducer, collects the generated mist as it travels out through the mouthpiece and to the user.

Figure 35:
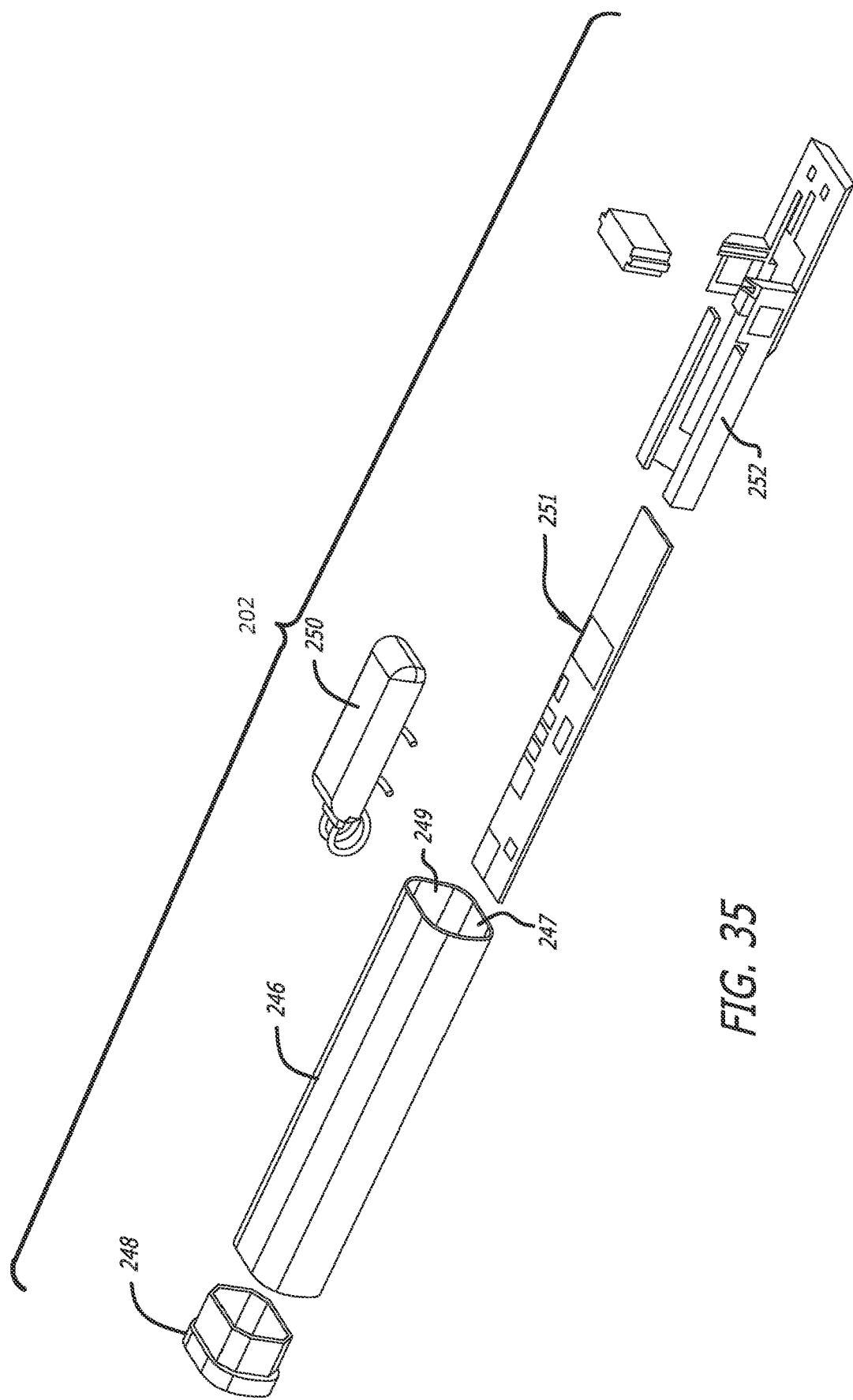
FIG. 35 is a diagrammatic exploded perspective view of a driver device of this disclosure.
Figure 36:
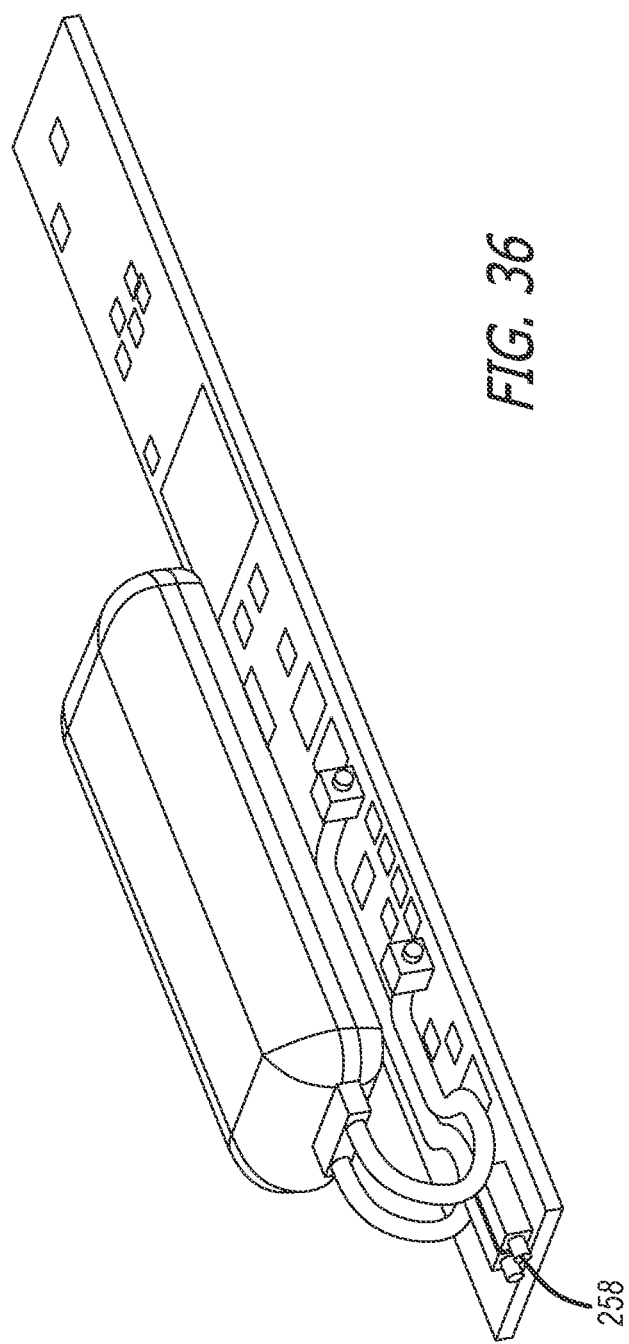
FIG. 36 is a diagrammatic perspective view of part of a driver device of this disclosure.
Figure 37:
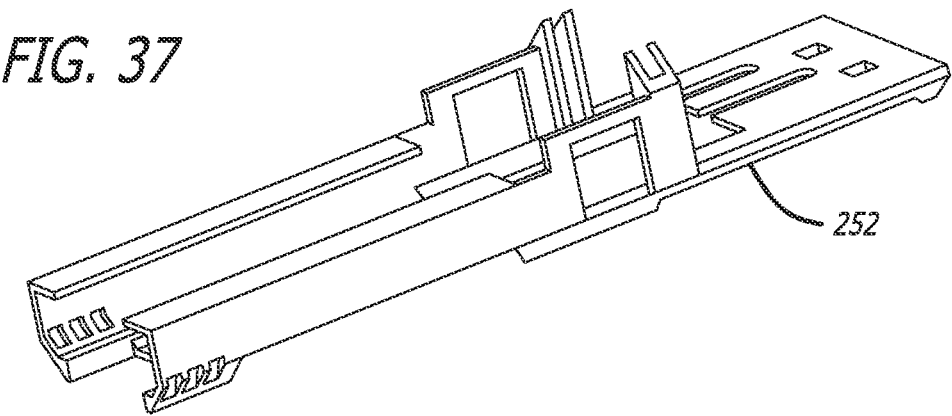
FIG. 37 is a diagrammatic perspective view of part of a driver device of this disclosure.
Figure 38:
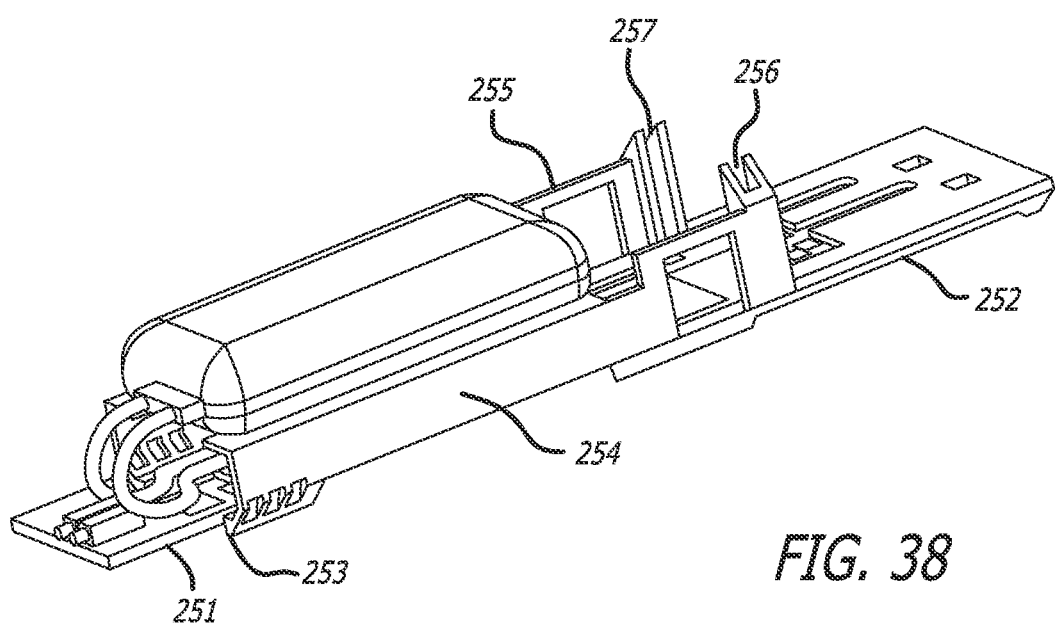
FIG. 38 is a diagrammatic perspective view of part of a driver device of this disclosure.

The driver device 202 will now be described with reference to FIGS. 35 and 36 initially. Air flows into the mist generator device 201 via the air inlet port 207 which, as described below, is in fluid communication with an airflow bridge within the driver device 202. The air flows along a flow path which changes the direction of the air flow by approximately 90° to direct the flow of air towards the ultrasonic transducer 215.

In some examples, the airflow arrangement is configured to change the direction of a flow of air along the air flow path such that the flow of air is substantially perpendicular to the atomisation surface of the ultrasonic transducer as the flow of air passes into the sonication chamber.

The driver device 202 comprises a driver device housing 246 which is at least partly of metal. In some examples, the driver device housing 246 is entirely of aluminium (AL6063 T6) which protects the internal components from the environment (dust, water splashes, etc.) and also protects from damage from shocks (accidental drops, etc.).

In some examples, the driver device housing 246 is provided with vents on its sides that allow ambient air to enter the device for two purposes; one to have ventilation around the electronic components and keep them within operating temperatures, and these vents also act as air inlets with air entering through these vents into the device, and then through the airflow bridge into the mist generator device 201.

The driver device housing 246 is elongate with an internal chamber 247 which houses the components of the driver device 202. One end of the driver device housing 246 is closed by an end cap 248. The other end of the driver device housing 247 has an opening 249 which provides an opening for the recess 203 of the driver device 202.

The driver device 202 comprises a battery 250 which is connected to a printed circuit board 251. In some examples, the battery 250 is a 3.7V DC Li—Po battery with 1140 mAh capacity and 10 C discharge rate. The high discharge rate is required for voltage amplification of up to 15V that is required by the ultrasonic transducer 215 for desirable operation. The shape and size of the battery is designed, within physical constraints, as per the shape and size of the device and space allocated for the power source.

The printed circuit board 251 incorporates a processor and a memory and other electronic components for implementing the electrical functions of the driver device 202. Charging pins 252 are provided on one end of the printed circuit board 251 and which extend through the end cap 248 to provide charging connections to charge the battery 250.

The printed circuit board 251 is retained within the driver device housing 246 by a skeleton 252. The skeleton 252 has a channel 253 which receives the printed circuit board 251. The skeleton 252 incorporates raised side portions 254, 255 which support the battery 250.

In some examples, the skeleton 252 is manufactured using industrial injection moulding processes. The moulded plastic skeleton ensures all parts are fixed and not loosely fitting inside the case. It also forms a cover over the front part of the PCB (Printed Circuit Board) which received the mist generator device 201 when it is inserted into the driver device 202.

Figure 39:
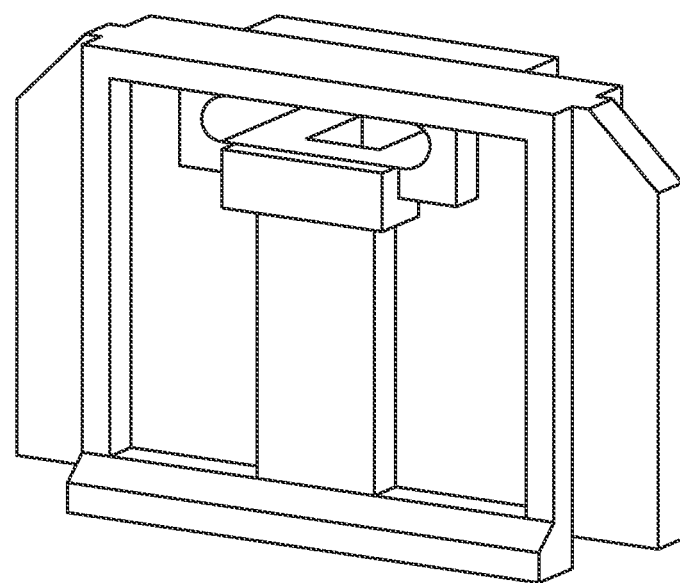
FIG. 39 is a diagrammatic perspective view of part of a driver device of this disclosure.
Figure 40:
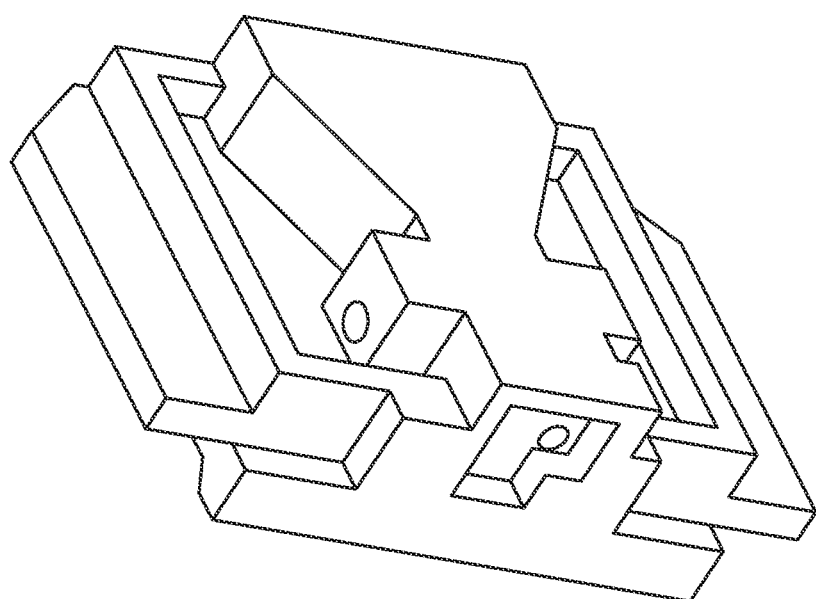
FIG. 40 is a diagrammatic perspective view of part of a driver device of this disclosure.
Figure 41:
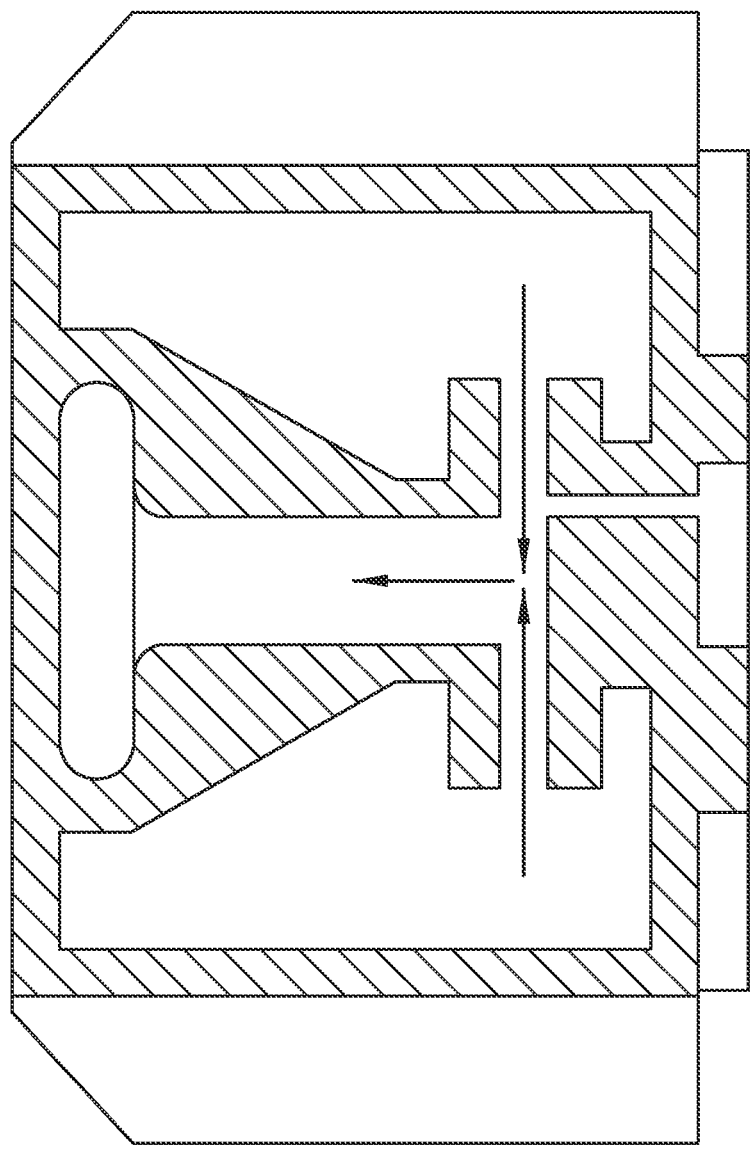
FIG. 41 is a diagrammatic perspective view of part of a driver device of this disclosure.
Figure 42:
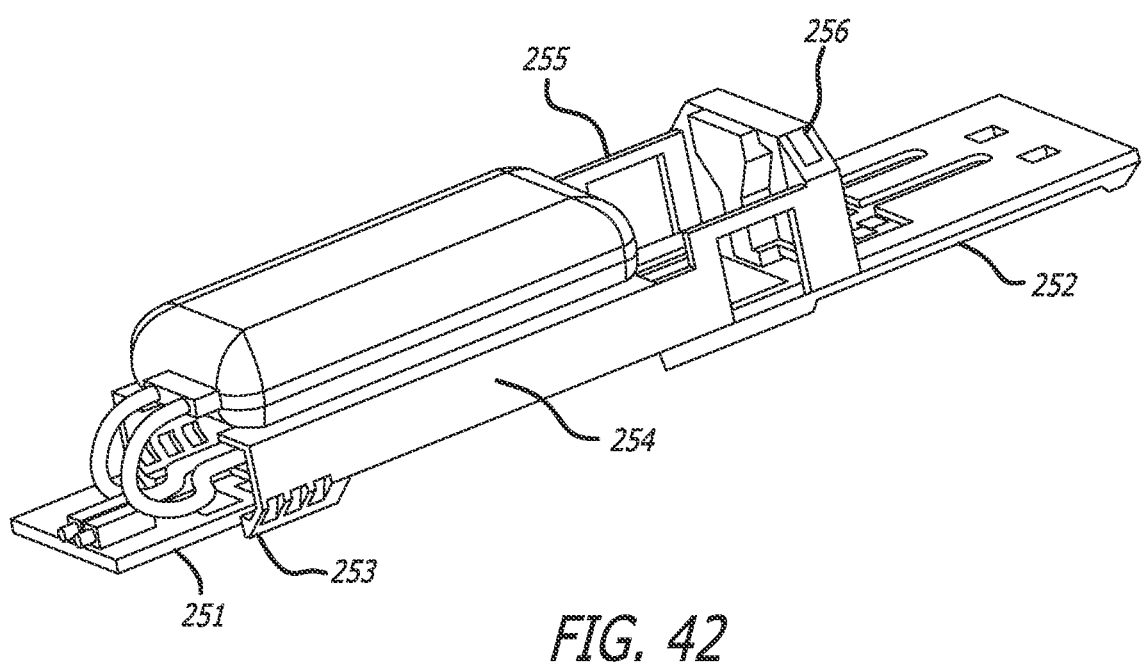
FIG. 42 is a diagrammatic perspective view of part of a driver device of this disclosure.

The driver device 202 comprises an airflow sensor which acts as a switch for activating and supplying power to the transducer for sonication and aerosol production. The airflow sensor is mounted onto the PCB in the device and requires a certain atmospheric pressure drop around it to activate the driver device 202. For this, an airflow bridge as shown in FIGS. 39 to 41 is designed with internal channels that direct air from the surrounding in through the bridge into the aerosol chamber. The skeleton 252 comprises opposing channels 256, 257 for receiving portions of the airflow bridge, as shown in FIG. 42.

The internal channels in the airflow bridge have a microchannel (0.5 mm diameter) that extends down towards a chamber that completely covers the airflow sensor. As the air flows in from the side inlets and upwards to the aerosol chamber, it creates a negative pressure in the micro-channel that triggers the airflow sensor to activate the device.

The device is a compact, portable and highly advanced device that allows precise, safe and monitored aerosolisation. This is done by incorporating high-quality electronic components designed with IPC class 3—medical grade—in mind.

The electronics of the driver device 202 are divided as such:

1. Sonication Section

In order to obtain the most efficient aerosolisation to date for inhalation in a portable device, with particle size below 1 um, the sonication section has to provide the contacts pads receiving the ultrasonic transducer 215 (piezoelectrical ceramic disc (PZT)) with high adaptive frequency (approximately 3 MHz).

This section not only has to provide high frequency but also protect the ultrasonic transducer 215 against failures while providing constant optimised cavitation.

PZT mechanical deformation is linked to the AC Voltage amplitude that is applied to it, and in order to guarantee optimal functioning and delivery of the system at every sonication, the maximum deformation must be supplied to the PZT all the time.

However, in order to prevent the failure of the PZT, the active power transferred to it must be precisely controlled.

This could only be achieved by designing a custom, not existing in the market, Power Management Integrated Circuit (PMIC) chip which is provided on the printed circuit board of the driver device 202. This PMIC allows modulation of the active power given to the PZT at every instant without compromising the mechanical amplitude of vibration of the PZT.

By Pulse Width Modulation (PWM) of the AC voltage applied to the PZT, the mechanical amplitude of the vibration remains the same.

The only 'on the shelf' option available would have been to modify the output AC voltage via the use of a Digital to Analog Converter (DAC). The energy transmitted to the PZT would be reduced but so would the mechanical deformation which as a result completely degrades and prevents proper aerosolisation. Indeed, the RMS voltage applied would be the same with effective Duty Cycle modulation as with Voltage modulation, but the active power transferred to the PZT would degrade, Indeed, given the formula below:

Active Power displayed to the PZT being $$Pa = \frac{2\sqrt{2}}{\pi} Irms * Vrms * \cos \varphi,$$

Where
φ is the shift in phase between current and voltage
$I_{rms}$ is the root mean square Current
$V_{rms}$ is the root mean square Voltage.

When considering the first harmonic, Irms is a function of the real voltage amplitude applied to the transducer, as the pulse width modulation alters the duration of voltage supplied to the transducer, controlling Irms.

The specific design of the PMIC uses a state-of-the-art design, enabling ultra-precise control of the frequency range and steps to apply to the PZT including a complete set of feedback loops and monitoring path for the control section to use.

The rest of the aerosolisation section is composed of the DC/DC boost converter and transformer that carry the necessary power from a 3.7 V battery to the PZT contact pads.

The driver device comprises an AC driver for converting a voltage from the battery into an AC drive signal at a predetermined frequency to drive the ultrasonic transducer.

The driver device comprises an active power monitoring arrangement for monitoring the active power used by the ultrasonic transducer (as described above) when the ultrasonic transducer is driven by the AC drive signal. The active power monitoring arrangement provides a monitoring signal which is indicative of an active power used by the ultrasonic transducer.

The processor within the driver device controls the AC driver and receives the monitoring signal drive from the active power monitoring arrangement.

The memory of driver device stores instructions which, when executed by the processor, cause the processor to:
A. control the AC driver to output an AC drive signal to the ultrasonic transducer at a predetermined sweep frequency;
B. calculate the active power being used by the ultrasonic transducer based on the monitoring signal;
C. control the AC driver to modulate the AC drive signal to maximise the active power being used by the ultrasonic transducer;
D. store a record in the memory of the maximum active power used by the ultrasonic transducer and the sweep frequency of the AC drive signal;
E. repeat steps A-D for a predetermined number of iterations with the sweep frequency incrementing with each iteration such that, after the predetermined number of iterations has occurred, the sweep frequency has been incremented from a start sweep frequency to an end sweep frequency;
F. identify from the records stored in the memory the optimum frequency for the AC drive signal which is the sweep frequency of the AC drive signal at which a maximum active power is used by the ultrasonic transducer; and G. control the AC driver to output an AC drive signal to the ultrasonic transducer at the optimum frequency to drive the ultrasonic transducer to atomise a liquid.

In some examples, the active power monitoring arrangement comprises a current sensing arrangement for sensing a drive current of the AC drive signal driving the ultrasonic transducer, wherein the active power monitoring arrangement provides a monitoring signal which is indicative of the sensed drive current.

In some examples, the current sensing arrangement comprises an Analog-to-Digital Converter which converts the sensed drive current into a digital signal for processing by the processor.

In some examples, the memory stores instructions which, when executed by the processor, cause the processor to: repeat steps A-D above with the sweep frequency being incremented from a start sweep frequency of 2900 kHz to an end sweep frequency of 2960 kHz.

In some examples, the memory stores instructions which, when executed by the processor, cause the processor to: repeat steps A-D above with the sweep frequency being incremented from a start sweep frequency of 2900 kHz to an end sweep frequency of 3100 kHz.

In some examples, the memory stores instructions which, when executed by the processor, cause the processor to: in step G, control the AC driver to output an AC drive signal to the ultrasonic transducer at frequency which is shifted by a predetermined shift amount from the optimum frequency.

In some examples, the predetermined shift amount is between 1-10% of the optimum frequency.

2. Control and Information (CI) Section

The Control and Information section comprises an external EEPROM for data storage, LEDs for user indications, a pressure sensor for airflow detection and a Bluetooth Low Energy (BLE) capable microcontroller for constant monitoring and managing of the aerosolisation section.

The pressure sensor used in the device serves two purposes. The first purpose is to prevent unwanted and accidental start of the sonic engine (driving the ultrasonic transducer). This functionality is implemented in the processing arrangement of the device, but optimised for low power, to constantly measures environmental parameters such as temperature and ambient pressure with internal compensation and reference setting in order to accurately detect and categorise what is called a true inhalation.

Unlike all the other e-smoking devices on the market, this solution uses the strength of a micro-controller to allow the use of only one sensor.

The second purpose of the pressure sensor is to be able to monitor not only the exact duration of the inhalations by the user for precise inhalation volume measurement, but also to be able to determine the strength of the user inhalation which is a critical information in medical conditions both for proper prescription and health monitoring. AH in all, we are able to completely draw the pressure profile of every inhalation and anticipate the end of an inhalation for both aerosolisation optimisation and medical data behaviour comprehension.

This was possible with the usage of a Bluetooth™ Low Energy (BLE) microcontroller. Indeed, this enables the setting to provide extremely accurate inhalation times, optimised aerosolisation, monitor numerous parameters to guarantee safe misting and prevent the use of non-genuine e-liquids or aerosol chambers and protect both the device against over-heating risks and the user against over-misting in one shot unlike any other products on the market.

The use of the BLE microcontroller allows over-the-air update to continuously provide improved software to users based on anonymised data collection and trained AI for PZT modelling.

3. Power Management (PM) Section

The Power Management section is constituted by the 3.7V LiPo battery path to a low dropout regulator (LDO) that powers the Control and Information section and a battery management system (BMS) that provides high level of protection and charging to the internal LiPo battery.

The components in this section have been selected carefully and thoroughly to be able to provide such an integrated and compact device while providing high power to the sonication section and ensuring a steady powering of the control and information section.

Indeed, when providing high power to the aerosolisation section from a 3.7V LiPo battery, the supply voltage varies a lot during operation. Without a low dropout regulator, the Control and Information section could not be powered with a mandatory steady supply when the battery voltage drops to as low as 0.3V above the minimum ratings of the components in this section, which is why the LDO plays a crucial role here. A loss in the CI section would disturb or even stop the functioning of the entire device.

This is why the careful selection of components not only ensures high reliability of the device but also allows it to work under harsh conditions and for a longer consecutive time between recharge.

Controlled Aerosolisation

The device is a precise, reliable and a safe aerosolisation solution for both smoke cessation programs, medical prescription and daily customer usage and, as such, must provide a controlled and trusted aerosolisation.

This is performed through an internal method that can be broken apart into several sections as follows:

1. Sonication

In order to provide the most optimal aerosolisation the ultrasonic transducer (PZT) needs to vibrate in the most efficient way.

Frequency

The electromechanical properties of piezoelectrical ceramics state that the component has the most efficiency at the resonant frequency. But also, vibrating a PZT at resonance for a long duration will inevitably end with the failure and breaking of the component which renders the aerosol chamber unusable.

Another important point to consider when using piezoelectrical materials is the inherent variability during manufacturing and its variability over temperature and lifetime.

Resonating a PZT at 3 MHz in order to create droplets of a size <1 um requires an adaptive method in order to locate and target the 'sweet spot' of the particular PZT inside every aerosol chamber used with the device for every single inhalation.

Sweep

Because the device has to locate the 'sweet spot' for every single inhalation and because of over-usage, the PZT temperature varies as the device uses an in-house double sweep method.

The first sweep is used when the device has not been used with a particular aerosol chamber for a time that is considered enough for all the thermal dissipation to occur and for the PZT to cool down to 'default temperature'. This procedure is also called a cold so start. During this procedure the PZT needs a boost in order to produce the required aerosol.

This is achieved by only going over a small subset of Frequencies between 2900 kHz to 2960 kHz which, considering extensive studies and experiments, covers the resonant point.

For each frequency in this range, the sonic engine in activated and the current going through the PZT is actively monitored and stored by the microcontroller via an Analog-to-Digital Converter (ADC), and converted back to current in order to be able to precisely deduct the Power used by the PZT.

This yields the cold profile of this PZT regarding frequency and the Frequency used throughout the inhalation is the one that uses the most current, meaning the lowest impedance Frequency.

The second sweep is performed during any subsequent inhalation and cover the entire range of frequencies between 2900 kHz to 3100 kHz due to the modification of the PZT profile with regards to temperature and deformation. This hot profile is used to determine the shift to apply.

Shift

Because the aerosolisation must be optimal, the shift is not used during any cold inhalation and the PZT will hence vibrate at resonant frequency. This can only happen for a short and unrepeated duration of time otherwise the PZT would inevitably break.

The shift however is used during most of inhalations as a way to still target a low impedance frequency, thus resulting in quasi-optimal operation of the PZT while protecting it against failures.

Because the hot and cold profiles are stored during inhalation the microcontroller can then select the proper shifted frequency according to the measured values of current through the PZT during sweep and ensure a safe mechanical operation.

The selection of the direction to shift is crucial as the piezoelectrical component behaves in a different way if outside the duplet resonant/anti-resonant frequency or inside this range. The selected shift should always be in this range defined by Resonant to anti-Resonant frequencies as the PZT is inductive and not capacitive.

Finally, the percentage to shift is maintained below 10% in order to still remain close to the lowest impedance but far enough of the resonance, Adjustment Because of the intrinsic nature of PZTs, every inhalation is different. Numerous parameters other than the piezoelectrical element influence the outcome of the inhalation, like the amount of e-liquid remaining inside the aerosol chamber, the wicking state of the gauze or the battery level of the device.

As of this, the device permanently monitors the current used by the PZT inside the aerosol chamber and the microcontroller constantly adjusts the parameters such as the frequency and the Duty Cycle in order to provide the aerosol chamber with the most stable power possible within a pre-defined range that follows the studies and experimental results for most optimal safe aerosolisation.

Battery Monitoring in order to provide an AC voltage of 15V and maintain a current inside the PZT around 2.5 A, the current drawn from the battery reaches around 7 to 8 Amps, which in turn, creates a drop in the battery voltage. Any common LiPo battery would not sustain this demanding resource for the duration of an inhalation that can top 6 s, This is the reason why a custom LiPo battery is developed that can handle around 11 Amps, which is 50% more than the maximum allowed in the PZT at all time, while still being simple to use in compact and integrated portable device.

Because the battery voltage drops and varies a lot when activating the sonication section, the microcontroller constantly monitors the power used by the PZT inside the aerosol chamber to ensure a proper but also safe aerosolisation.

And because the key to aerosolisation is control, the device ensures first that the Control and Information section of the device always function and does not stop in the detriment of the sonication section.

This is why the adjustment method also takes into great account the real time battery level and, if need be, modifies the parameters like the Duty Cycle to maintain the battery at a safe level, and in the case of a low battery before starting the sonic engine, the Control and Information section will prevent the activation.

Power Control

As being said, the key to aerosolisation is control and the method used in the device is a real time multi-dimensional function that takes into account the profile of the PZT, the current inside the PZT and the battery level of the device at all time.

All this is only achievable thanks to the use of a microcontroller that can monitor and control every element of the device to produce an optimal inhalation.

1. Inhalation Control

The device is a safe device and confirmed by BNS (Broughton Nicotine Services) report, but in order to guarantee the safety of misting and the integrity of both the aerosol chamber and the device, each inhalation has to be controlled.

Inhalation Duration

In order to reduce the exposure to carbonyls and other toxic components that might result from the heating of e-liquid, the maximum duration of an inhalation is set to 6 seconds which completely ensure that the exposure to these components is contained.

Interval

Because the device relies on a piezoelectrical component, the device prevents the activation of the sonication section if an inhalation stops. The safety delay in between two inhalations is adaptive depending on the duration of the previous one. This allows the gauze to wick properly before the next activation.

With this functioning, the device can safely operate and the aerosolisation is rendered more optimal with no risk of breaking the PZT element nor exposing the user to toxic components.

Connectivity (BLE)

The device Control and Information section is composed of a wireless communication system in the form of a Bluetooth Low Energy capable microcontroller. The wireless communication system is in communication with the processor of the device and is configured to transmit and receive data between the driver device and a computing device, such as a smartphone.

The connectivity via Bluetooth Low Energy to a companion mobile application ensures that only small power for this communication is required thus allowing the device to remain functioning for a longer period of time if not used at all, compared to traditional wireless connectivity solutions like Wi-Fi, classic Bluetooth, GSM or even LTE-M and NB-IOT.

Most importantly, this connectivity is what enables the OTP as a feature and the complete control and safety of the inhalations. Every data from resonant frequency of an inhalation to the one used, or the negative pressure created by the user and the duration are stored and transferred over BLE for further analysis and improvements of the embedded software.

Moreover, all these information are crucial when the device is used in medical or smoke cessation programs because it gives doctors and users all the information regarding the process of inhalation and the ability to track in real-time the prescriptions and the usage.

Finally, this connectivity enables the update of the embedded firmware inside the device and over the air (OTA), which guarantees that the latest versions can always be deployed rapidly. This gives great scalability to the device and insurance that the device is intended to be maintained.

Data Collection for Clinical Smoke Cessation Purposes

The device can collect user data such as number of puffs and puff duration in order to determine the total amount of drug consumed by the user in a session.

This data can be interpreted by an algorithm that sets consumption limits per time period based on a physician's recommendations.

This will allow a controlled therapeutic dose of drug to be administered to the user that is controlled by a physician or pharmacist and cannot be abused by the end user.

The physician would be able to gradually lower dosages over time in a controlled method that is both safe for the user and effective in providing therapeutic smoke cessation doses.

Puff Limitations

The process of ultrasonic cavitation has a significant impact on the nicotine concentration in the produced mist.

A device limitation of <7 second puff durations will limit the user to exposure of carbonyls commonly produced by electronic nicotine delivery systems.

Based on Broughton Nicotine Services' experimental results, after a user performs 10 consecutive puffs of <7 seconds, the total amount of carbonyls is <2.67 µg/10 puffs (average: 1.43 µg/10 puffs) for formaldehyde, <0.87 µg/10 puffs (average: 0.50 µg/10 puffs) for acetaldehyde, <0.40 µg/10 puffs (average: 0.28 µg/10 puffs) for propionaldehyde, <0.16 µg/10 puffs (average: 0.16 µg/10 puffs) for crotonaldehyde, <0.19 µg/10 puffs (average; 0.17 µg/10 puffs) for butyraldehyde, <0.42 µg/10 puffs (average; 0.25 µg/10 puffs) for diacetyl, and acetylpropionyl was not detected at all in the emissions after 10 consecutive <7 second puffs.

Because the aerosolisation of the e-liquid is achieved via the mechanical action of the piezoelectric disc and not due to the direct heating of the liquid, the individual components of the e-liquid (propylene glycol, vegetable glycerine, flavouring components, etc.) remain largely in-tact and are not broken into smaller, harmful components such as acrolein, acetaldehyde, formaldehyde, etc. at the high rate seen in traditional ENDS.

In order to limit the user's exposure to carbonyls while using the ultrasonic device, puff length is limited to 6 seconds maximum so that the above results would be the absolute worst-case scenario in terms of exposure.

Figure 43:
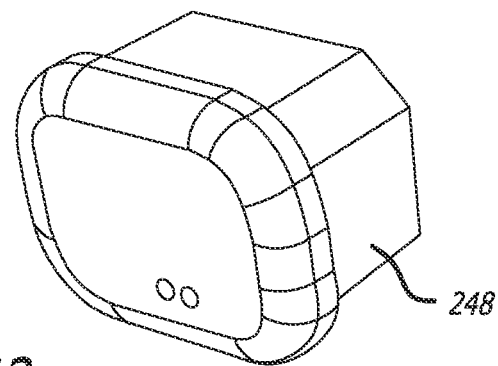
FIG. 43 is a diagrammatic perspective view of an end cap of a driver device of this disclosure.
Figure 44:
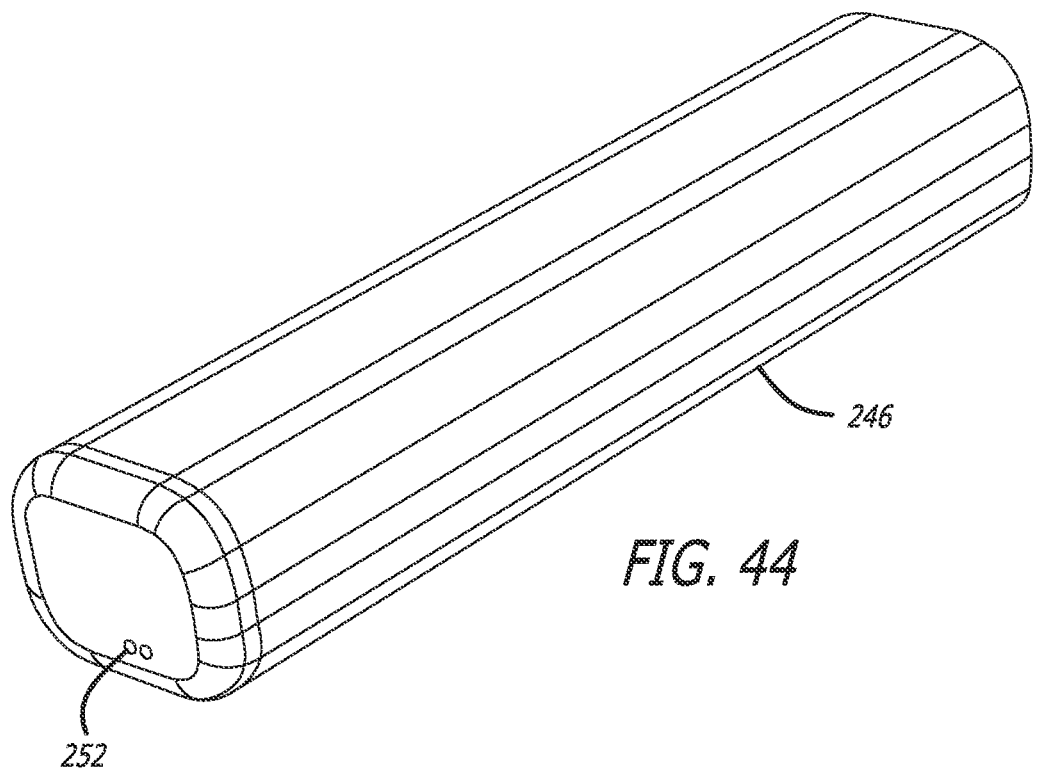
FIG. 44 is a diagrammatic perspective view of the housing of a driver device of this disclosure.
Figure 45:
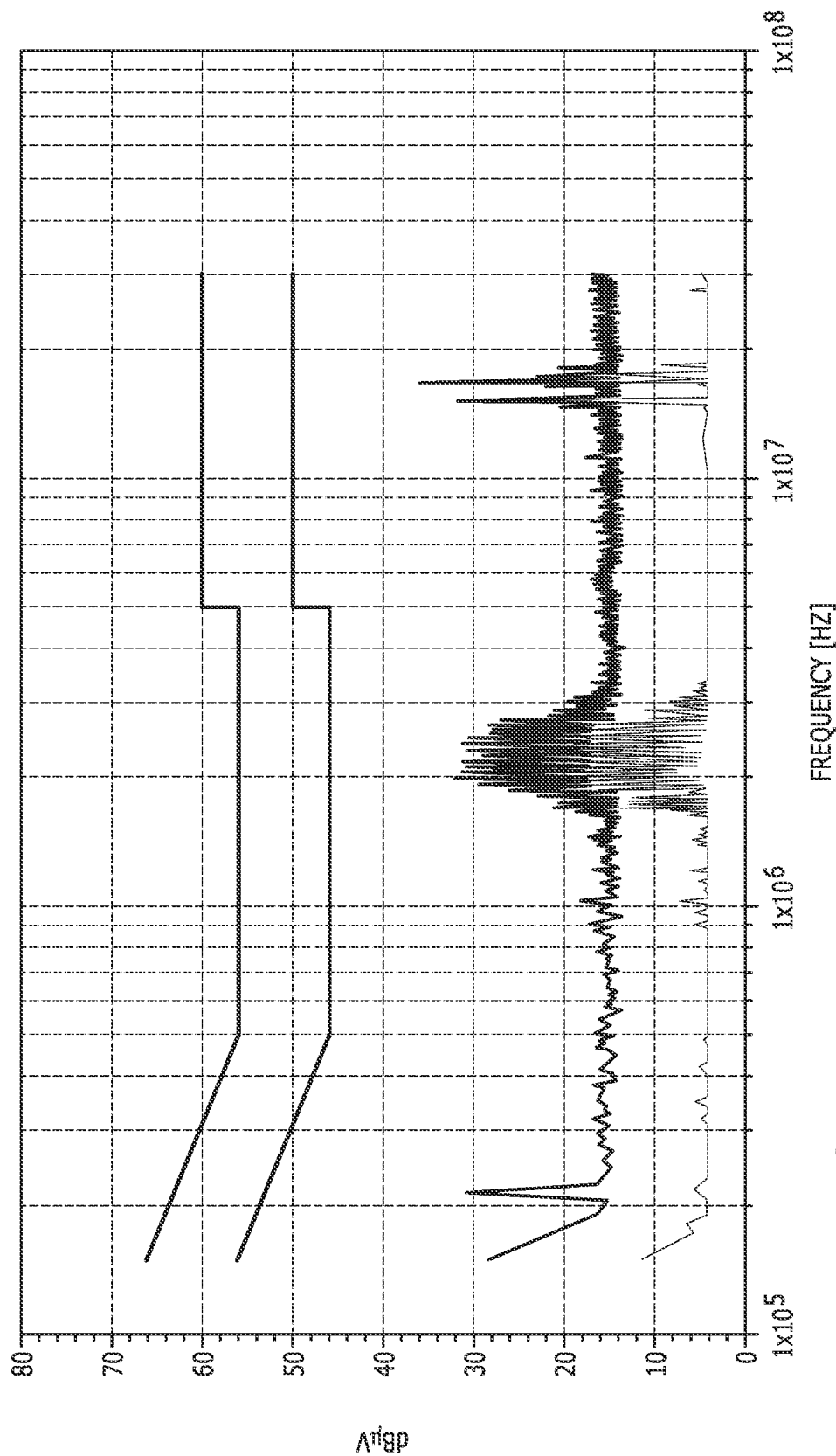
FIG. 45 is a graph showing the result of an EMC test for a mist inhaler device of this disclosure.

Referring now to FIGS. 43 and 44, when the end cap 248 is mounted to the driver device housing 246, the driver device housing 246, being aluminium, acts as a Faraday cage, preventing the device from emitting any electromagnetic waves. The device with the driver device housing 246 has been tested for Electromagnetic Compatibility (EMC) and the tests reveal that the emissions are less than half the allowed limit for devices. The EMC test results are shown in the graph of FIG. 45.

All of the above applications involving ultrasonic technology can benefit from the optimisation achieved by the frequency controller which optimises the frequency of sonication for optimal performance.

It is to be appreciated that the disclosures herein are not limited to use for nicotine delivery. Some examples are configured for use for various medical purposes (e.g. the delivery of CBD for pain relief, supplements for performance enhancement, albuterol/salbutamol for asthma patients, etc.)

The devices disclosed herein are for use with any drugs or other compounds, with the drug or compound being provided in a liquid within the liquid chamber of the device for aerosolisation by the device. In some examples, the devices disclosed herein are for use with drugs and compounds including, but not limited to, the following:

Respiratory
Brochodilators
Olodaterol
Levalbuterol
Berodual (Ipratropium bromide/Fenoterol)
Combivent (Ipratropium bromide/Salbutamol)
Anti-Inflammatory
Betamethasone
Dexamethasone
Methylprednisolone
Hydrocortisone
Mucolytics
N-Acetylcysteine
Pulmonary Hypertension
Sildenafil
Tadalafil
Epoprostenol
Treprostenil
Iloprost
Infectious Disease
Antimicrobials
Aminoglycosides (Gentamicin, Tobramycin, Amikacin, Colomycin, Neomycin, Liposomal Amikacin)
Quinolones (Ciprofloxacin, Levofloxacin, Moxifloxacin Ofloxacin)
Macrolides (Azithromycin)
Minocycline
Betalactams (Piperacillin-Tazobactam, Ceftazidime Ticarcillin)
Cephalosporins (Cefotaxime, Cefepime, Ceftriaxone, Cefotaxime)
Glycopeptides (Vancomycin)
Meropenem
Polymixin (Colistin, Polymixin B)
Antifungals
Amphotericin
Fluconazole
Caspofungen
Antivirals
Valganciclovir
Favipiravir
Remdisivir
Acyclovir
Anti TB
Isoniazid
Pyrazinamide
Rifampin
Ethambutol
Oncology
Biologics
Gilotrif Afatinib
Caplacizumab
Dupilurnab
Isarilumab
Alirucomab
Volasertib
Nintedanib
Imatinib
Sirolimus
Chemotherapy
Azacitidine
Decitabine
Docetaxel
Gemcitabine
Cisplatinum
CNS & PSYCH
Sodium valproate
Teriflunomide
Zornitriptan
METABOLIC/HORMONAL
Insulin
Estrogen
IMMUNOLOGY
Vaccine
Monoclonal Antibodies
Stem Cells
Vitamins
Zinc
Ascorbic Acid
Miscellaneous
Niclosamide
Hydroxychloroquine
Ivermectin The ultrasonic mist inhaler 100 of some examples is a more powerful version of current portable medical nebulizers, in the shape and size of current e-cigarettes and with a particular structure for effective vaporization. It is a healthier alternative to cigarettes and current e-cigarettes products.

The ultrasonic mist inhaler 100 of some examples has particular applicability for those who use electronic inhalers as a means to quit smoking and reduce their nicotine dependency. The ultrasonic mist inhaler 100 provides a way to gradually taper the dose of nicotine.

Other examples of the ultrasonic mist inhaler devices are easily envisioned, including medicinal delivery devices.

The foregoing outlines features of several examples or embodiments so that those of ordinary skill in the art may better understand various aspects of the present disclosure. Those of ordinary skill in the art should appreciate that they may readily use the present disclosure as a basis for designing or modifying other processes and structures for carrying out the same purposes and/or achieving the same advantages of various examples or embodiments introduced herein. Those of ordinary skill in the art should also realise that such equivalent constructions do not depart from the spirit and scope of the present disclosure, and that they may make various changes, substitutions, and alterations herein without departing from the spirit and scope of the present disclosure.

Although the subject matter has been described in language specific to structural features or methodological acts, it is to be understood that the subject matter of the appended claims is not necessarily limited to the specific features or acts described above. Rather, the specific features and acts described above are disclosed as example forms of implementing at least some of the claims.

Various operations of examples or embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some examples or embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "With", or variants thereof are used, such terms are intended to be inclusive in a manner similar to the term "comprising". Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Also, although the disclosure has been shown and described with respect to one or more implementations, equivalent alterations and modifications will occur to others of ordinary skill in the art based upon a reading and understanding of this specification and the annexed drawings. The disclosure comprises all such modifications and alterations and is limited only by the scope of the following claims, in particular regard to the various functions performed by the above described features (e.g., elements, resources, etc.), the terms used to describe such features are intended to correspond, unless otherwise indicated, to any features which performs the specified function of the described features (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

Examples or embodiments of the subject matter and the functional operations described herein can be implemented in digital electronic circuitry, or in computer software, firmware, or hardware, including the structures disclosed in this specification and their structural equivalents, or in combinations of one or more of them.

Some examples or embodiments are implemented using one or more modules of computer program instructions encoded on a computer-readable medium for execution by, or to control the operation of, a data processing apparatus. The computer-readable medium can be a manufactured product, such as hard drive in a computer system or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The terms "computing device" and "data processing apparatus" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

The processes and logic flows described in this specification can be performed by one or more programmable processors executing one or more computer programs to perform functions by operating on input data and generating output.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices.

In the present specification "comprise" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A mist generator device comprising:
   a mist generator housing which is elongate and terminates at a bottom end and a top end opposite bottom end, the housing having opposite sides positioned between the top end and bottom end, a central longitudinal axis passing through the top end and the bottom end, an air inlet port formed in the bottom end, and a mist outlet port formed in the top end;
   a liquid chamber provided within the mist generator housing, the liquid chamber configured to contain a liquid to be atomised;
   a sonication chamber provided within the mist generator housing;
   a capillary element extending between the liquid chamber and the sonication chamber such that a first portion of the capillary element is within the liquid chamber and a second portion of the capillary element is within the sonication chamber;
   an ultrasonic transducer having an atomisation surface which is provided within the sonication chamber, the ultrasonic transducer being mounted within the mist generator housing such that the plane of the atomisation surface is substantially parallel with the central longitudinal axis of the mist generator housing, wherein part of the second portion of the capillary element is positioned over at least part of the atomisation surface, and wherein the ultrasonic transducer is configured to vibrate the atomisation surface to atomise a liquid carried by the second portion of the capillary element to generate the mist comprising the atomised liquid and air within the sonication chamber; and
   an airflow channel which provides an air flow path between the air inlet port, the sonication chamber and the air outlet port such that a user drawing on the mist outlet port draws air through the inlet port, through the sonication chamber and out through the mist outlet port, the airflow channel is configured to change the direction of a flow of air along the air flow path as the flow of air passes into the sonication chamber, wherein the airflow channel comprises:
   a first portion initiating at the air inlet port, the first portion of the air flow channel being substantially vertical and having a longitudinal axis that is substantially parallel to the central longitudinal axis of the housing and passing through the air inlet port, the first portion continuing to a second portion of the airflow channel and the second portion being in direct communication with the sonication chamber,
   the second portion of the airflow channel being substantially horizontal and having a central longitudinal axis that is substantially perpendicular to the central longitudinal axis of the housing and is substantially perpendicular to the plane of the atomisation surface of the ultrasonic transducer, the central longitudinal axis of the second portion intersecting at least a portion of the atomization surface such that the direction of the flow of air is substantially perpendicular to the plane of the atomisation surface of the ultrasonic transducer, the substantially vertical first portion of the air flow channel extending from the bottom end to the substantially horizontal second portion of the air flow channel, when the mist generator device is in an upright position, the mist outlet port is at the top end and the air inlet port is at the bottom end, and the ultrasonic transducer is positioned above the air inlet port, and
   a third portion of the airflow channel having a longitudinal axis that is substantially parallel to the central longitudinal axis of the housing and continues from the sonication chamber toward the air outlet opening with the mist generated in the sonication chamber being carried by the air out through the mist outlet port for inhalation by the user.

2. The mist generator device of claim 1 further comprising:
   a transducer holder which is held within the mist generator housing, the transducer element holds the ultrasonic transducer and retains the second portion of the capillary element superimposed on part of the atomisation surface; and
   a divider portion which provides a barrier between the liquid chamber and the sonication chamber, wherein the divider portion comprises a capillary aperture through which part of the first portion of the capillary element extends.

3. The mist generator device of claim 2, wherein the transducer holder is of a liquid silicone rubber having a Shore A 60 hardness.

4. The mist generator device of claim 1, wherein the capillary element comprises a first part and a second part which are superimposed on one another such that the capillary element has two layers.

5. The mist generator device of claim 1, wherein the capillary element comprising at least 75% bamboo fibre.

6. The mist generator device of claim 1, wherein the airflow channel is configured to change the direction of a flow of air along the air flow path such that the flow of air is substantially perpendicular to the atomisation surface of the ultrasonic transducer as the flow of air passes into the sonication chamber.

7. The mist generator device of claim 1, further comprising:

at least one absorbent element which is provided adjacent the mist outlet port to absorb liquid at the mist outlet port.

8. The mist generator device of claim 1, wherein the mist generator housing is made from at least partly of a heterophasic copolymer.

9. The mist generator device of claim 1, wherein the liquid chamber contains a liquid having a liquid viscosity between 1.05 Pa·s and 1.412 Pa·s and a liquid density between 1.1 g/ml and 1.3 g/ml.

10. The mist generator device of claim 1, wherein the liquid chamber contains a liquid comprising a nicotine levulinate salt at a 1:1 molar ratio.

11. The mist generator device of claim 1 further comprising:

an identification arrangement which is provided on the mist generator housing, the identification arrangement comprising:

an integrated circuit having a memory which stores a unique identifier for the mist generator device; and an electrical connection which provides an electronic interface for communication with the integrated circuit.

* * * * *